US011977076B2

(12) United States Patent
Brody et al.

(10) Patent No.: US 11,977,076 B2
(45) Date of Patent: May 7, 2024

(54) DIAGNOSTIC AND PROGNOSTIC METHODS FOR LUNG DISORDERS USING GENE EXPRESSION PROFILES FROM NOSE EPITHELIAL CELLS

(71) Applicant: Trustees of Boston University, Boston, MA (US)

(72) Inventors: Jerome S. Brody, Boston, MA (US); Avrum Spira, Newton, MA (US); Jeffrey S. Berman, Cambridge, MA (US); Anthony W. O'Regan, Galway (IE)

(73) Assignee: Trustees of Boston University, Boston, MA (US)

(*) Notice: Subject to any disclaimer, the term of this patent is extended or adjusted under 35 U.S.C. 154(b) by 0 days.

(21) Appl. No.: 16/579,798

(22) Filed: Sep. 23, 2019

(65) Prior Publication Data
US 2020/0096513 A1 Mar. 26, 2020

Related U.S. Application Data

(63) Continuation of application No. 14/690,182, filed on Apr. 17, 2015, now abandoned, which is a continuation of application No. 13/323,655, filed on Dec. 12, 2011, now abandoned, which is a continuation of application No. 12/940,840, filed on Nov. 5, 2010, now abandoned, which is a continuation of application No. 12/282,320, filed as application No. PCT/US2007/006006 on Mar. 8, 2007, now abandoned.

(60) Provisional application No. 60/780,552, filed on Mar. 9, 2006.

(51) Int. Cl.
*C12Q 1/6886* (2018.01)
*G01N 33/574* (2006.01)

(52) U.S. Cl.
CPC ..... *G01N 33/57423* (2013.01); *C12Q 1/6886* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,640,268 A | 2/1972 | Davis |
| 4,641,662 A | 2/1987 | Jaicks |
| 4,800,896 A | 1/1989 | Jalowayski |
| 5,422,273 A | 6/1995 | Garrison |
| 5,440,942 A | 8/1995 | Hubbard |
| 5,477,863 A | 12/1995 | Grant |
| 5,726,060 A | 3/1998 | Bridges |
| 5,795,782 A | 8/1998 | Church et al. |
| 5,876,978 A | 3/1999 | Willey et al. |
| 6,085,907 A | 7/2000 | Hochmeister |
| 6,667,154 B1 * | 12/2003 | Wang ............... C07K 14/47 435/6.16 |
| 6,676,609 B1 | 1/2004 | Rutenberg |
| 6,746,846 B1 | 6/2004 | Wang et al. |
| 10,927,417 B2 | 2/2021 | Beane-Ebel et al. |
| 2002/0081612 A1 | 6/2002 | Katz et al. |
| 2002/0094547 A1 | 7/2002 | Burstein |
| 2002/0160388 A1 | 10/2002 | Macina et al. |
| 2003/0104499 A1 | 6/2003 | Pressman et al. |
| 2003/0186248 A1 | 10/2003 | Erlander |
| 2004/0005294 A1 | 1/2004 | Lee |
| 2004/0009489 A1 | 1/2004 | Golub et al. |
| 2004/0063120 A1 | 4/2004 | Beer et al. |
| 2004/0197785 A1 | 10/2004 | Willey et al. |
| 2004/0241725 A1 | 12/2004 | Xiao et al. |
| 2004/0241728 A1 | 12/2004 | Liew |
| 2005/0260586 A1 | 11/2005 | Demuth et al. |
| 2005/0266409 A1 | 12/2005 | Brown et al. |
| 2006/0127928 A1 | 6/2006 | Bacus et al. |
| 2006/0140960 A1 | 6/2006 | Wang et al. |
| 2006/0154278 A1 | 7/2006 | Brody et al. |
| 2006/0183144 A1 | 8/2006 | Willey et al. |
| 2006/0188909 A1 | 8/2006 | Willey et al. |
| 2006/0190192 A1 | 8/2006 | Willey et al. |
| 2006/0194216 A1 | 8/2006 | Willey et al. |
| 2007/0092891 A1 | 4/2007 | Willey et al. |
| 2007/0092892 A1 | 4/2007 | Willey et al. |

(Continued)

FOREIGN PATENT DOCUMENTS

| | | |
|---|---|---|
| CN | 1688582 A | 10/2005 |
| DE | 10219117 | 10/2003 |

(Continued)

OTHER PUBLICATIONS

Guajardo (J Allery Clin Immunol Feb. 2005 vol. 115 No. 2 pp. 243-251).*
Gebel (Carcinogenesis vol. 25 No. 2 pp. 169-178 2004 pp. 169-178).*
Sabo-Attwood (American Journal of Pathology vol. 167 No. 5 Nov. 2005 pp. 1243-1256).*
Lee (Acta Oto-Laryngologica 2001 121:7, 849-853).*
Lampe (Cancer Epidemiology, Biomarkers, and Prevention 2004; 13(3) Mar. 2004).*
Chan (G&P magazine 2006 vol. 6 No. 3 pp. 20-26).*
Whitehead (Genome Biology 2005 vol. 6 Issue 2 Article R13).*
Jones, A. M., et al. "Value and accuracy of cytology in addition to histology in the diagnosis of lung cancer at flexible bronchoscopy." Respiratory medicine 95.5 (2001): 374-378.

(Continued)

*Primary Examiner* — Amanda Haney
(74) *Attorney, Agent, or Firm* — Morse, Barnes-Brown & Pendleton, P.C.; Lisa M. Warren, Esq.; Erin E. Bryan, Esq.

(57) ABSTRACT

The present invention provides methods for diagnosis and prognosis of lung cancer using expression analysis of one or more groups of genes, and a combination of expression analysis from a nasal epithelial cell sample. The methods of the invention provide far less invasive method with a superior detection accuracy for lung cancer when compared to any other currently available method for lung cancer diagnostic or prognosis. The invention also provides methods of diagnosis and prognosis of other lung diseases, such as lung cancer.

12 Claims, 15 Drawing Sheets

(56) References Cited

U.S. PATENT DOCUMENTS

Figure 1A:
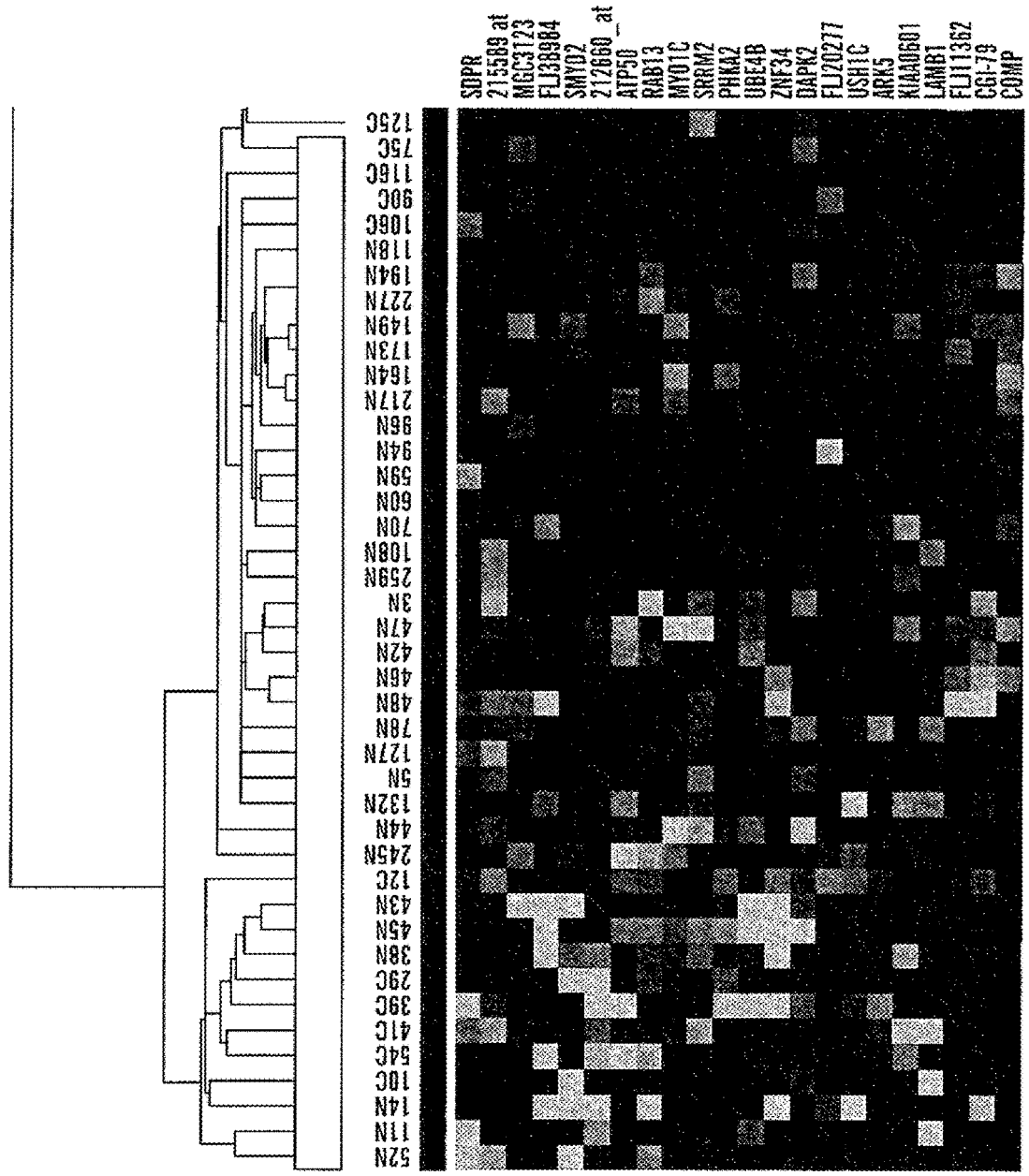
Figure 1B:
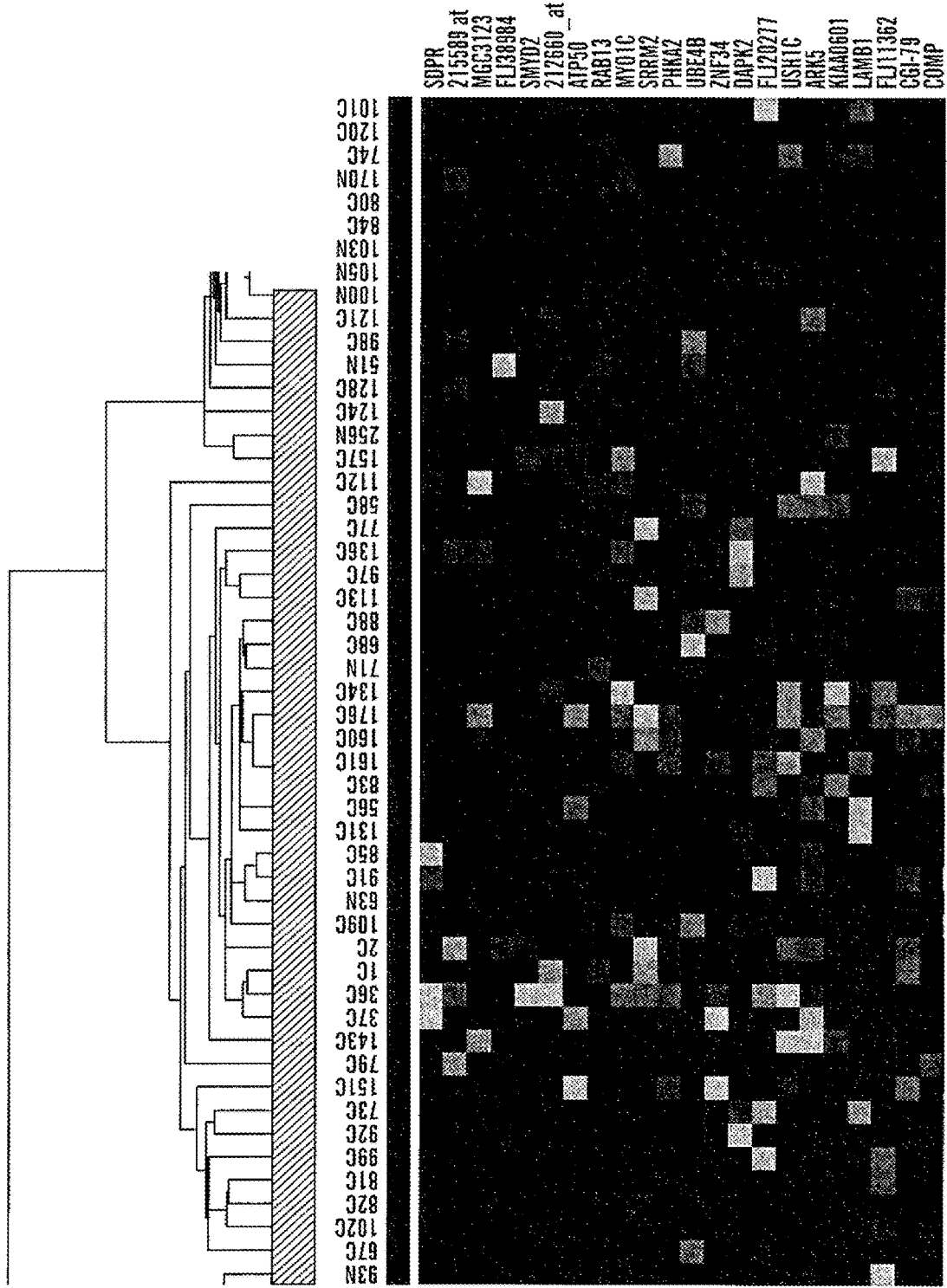
Figure 1C:
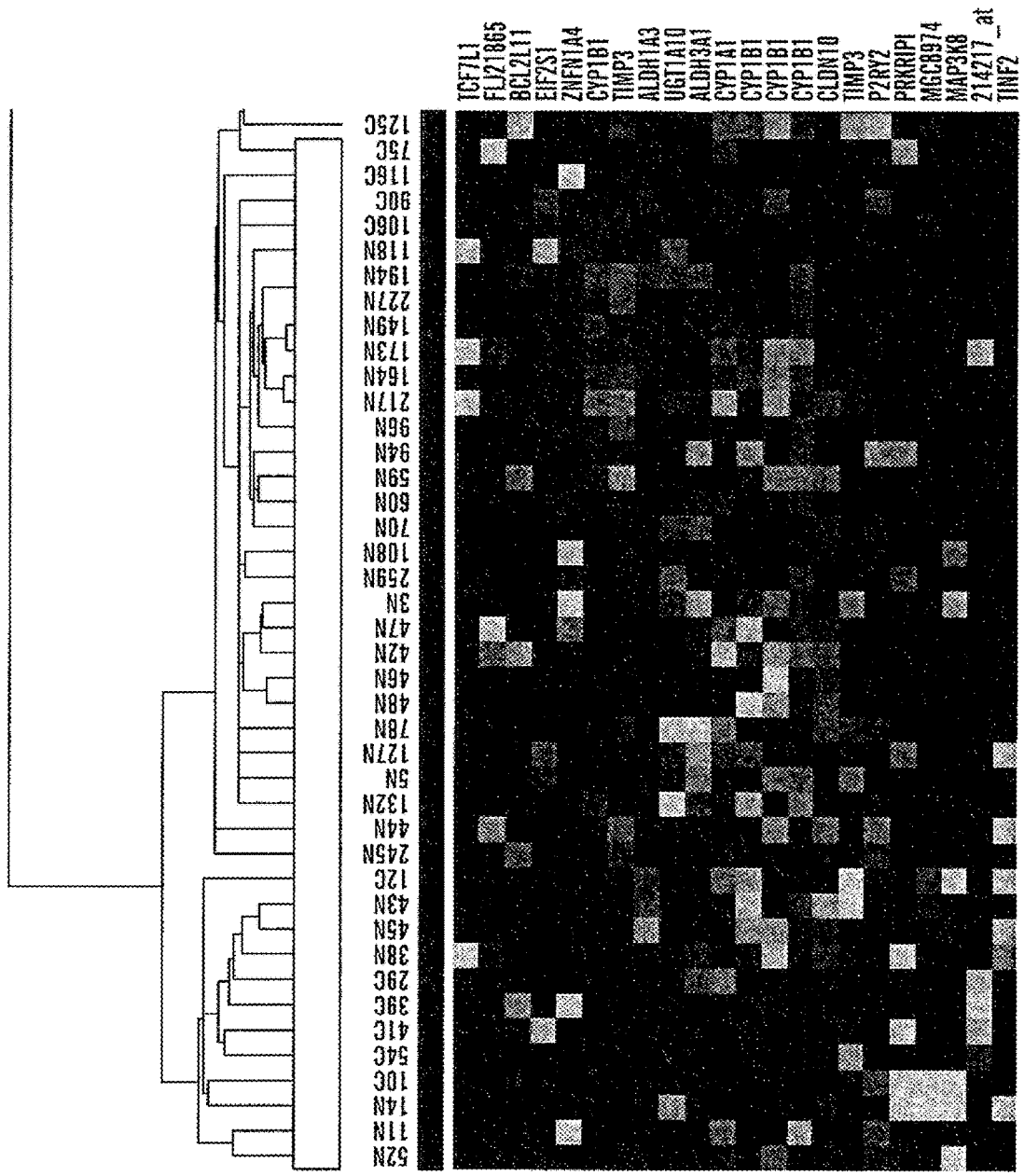
Figure 1D:
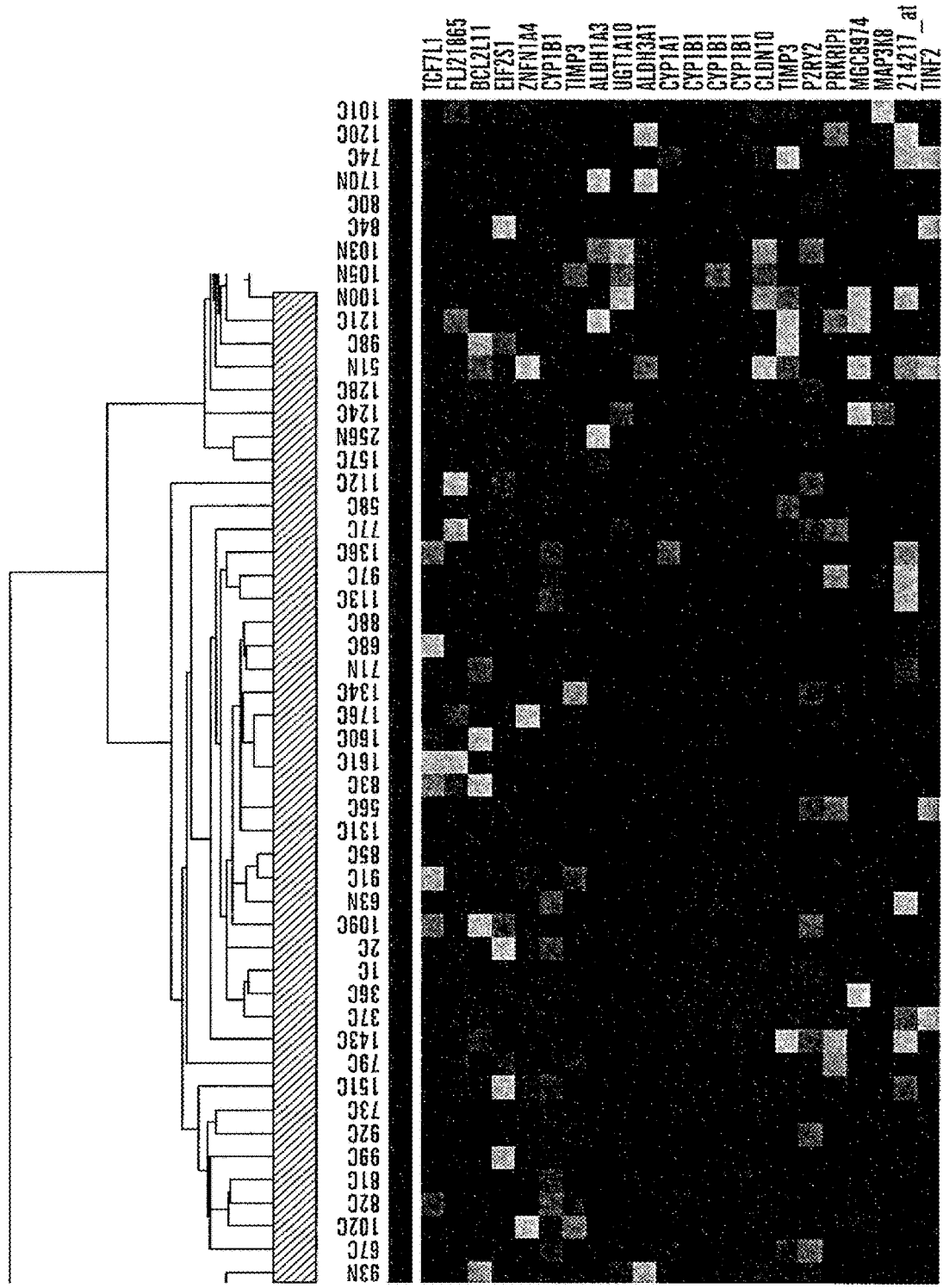
Figure 1E:
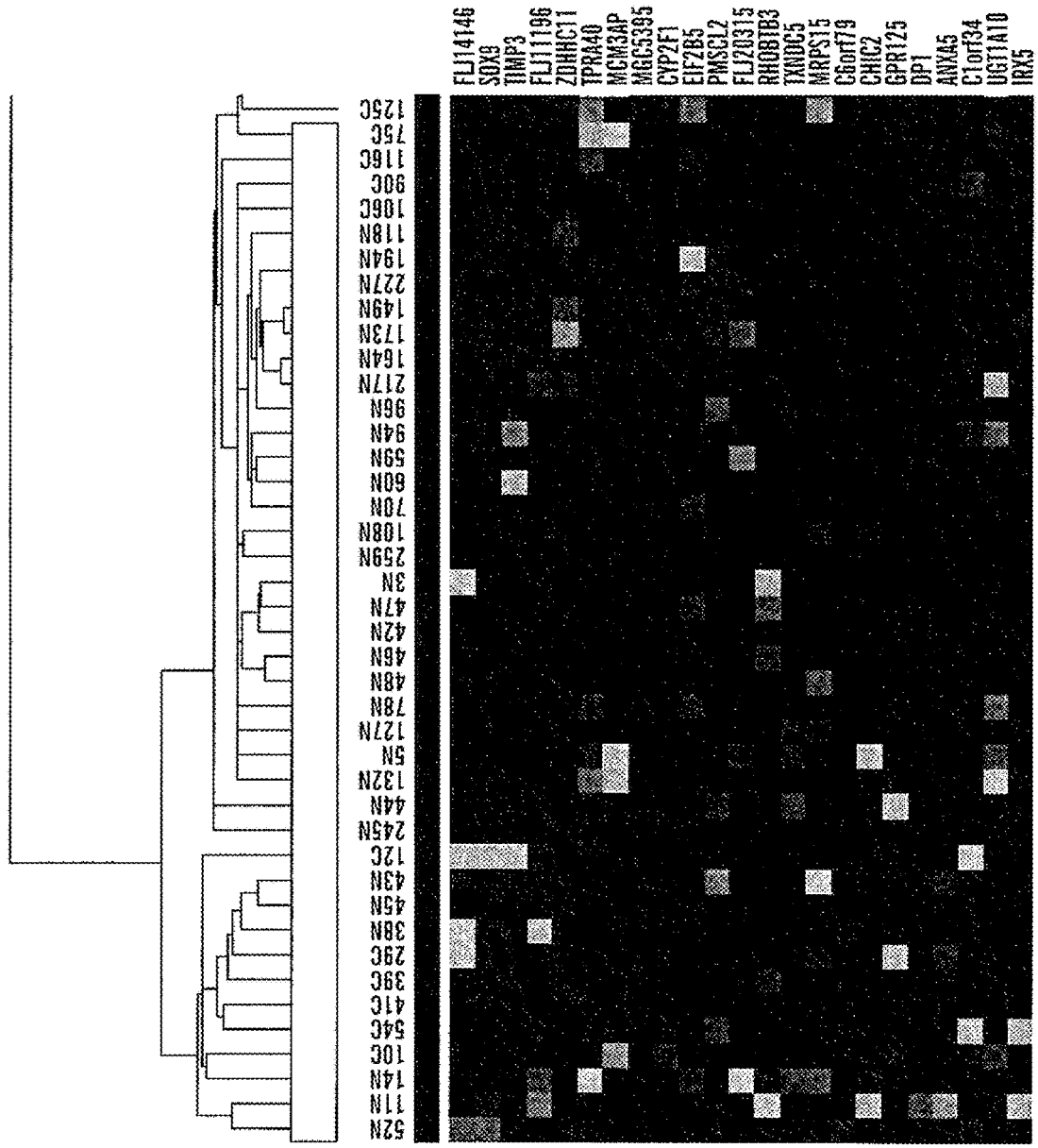
Figure 1F:
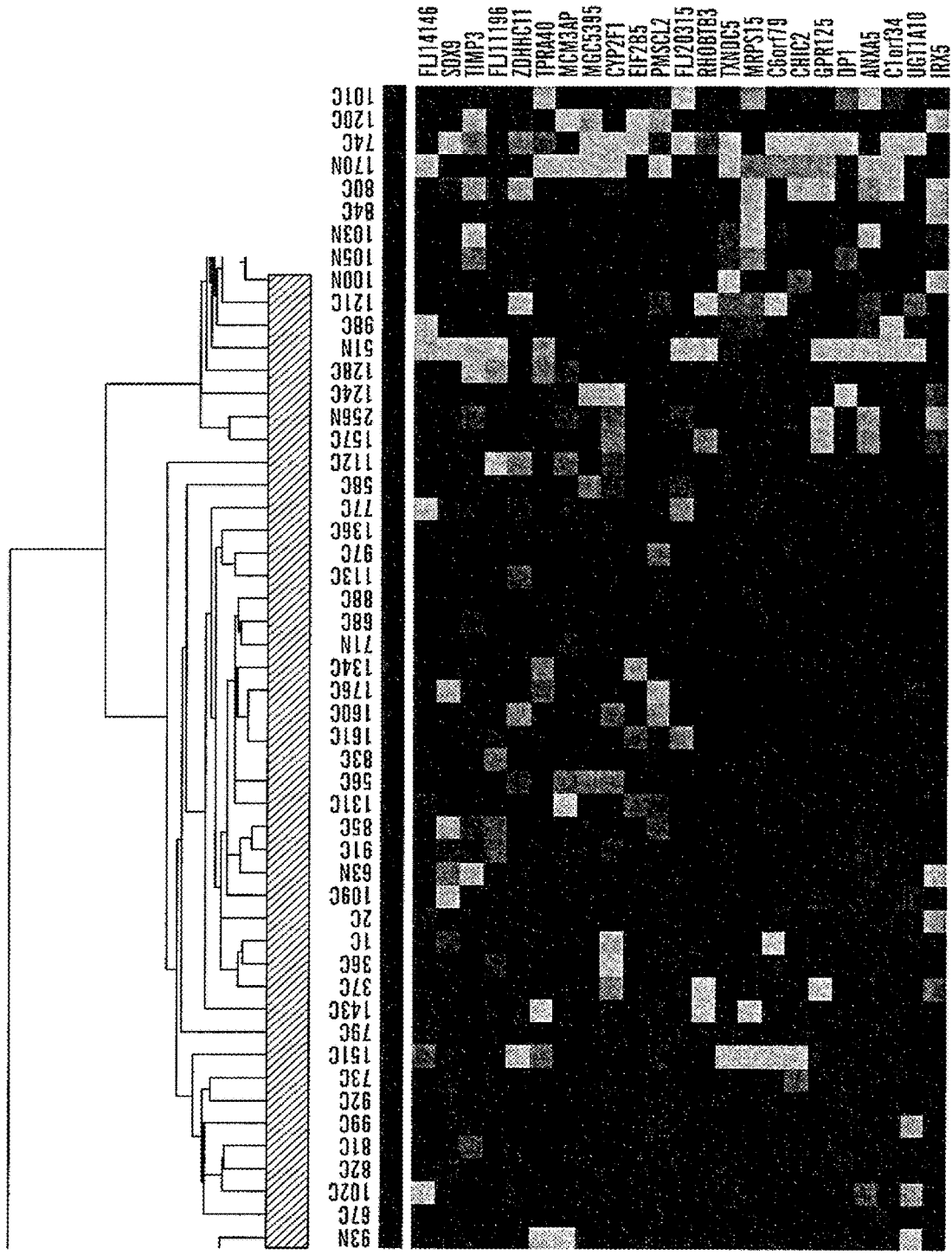

| | | |
|---|---|---|
| 2007/0092893 A1 | 4/2007 | Willey et al. |
| 2007/0148650 A1 | 6/2007 | Brody et al. |
| 2009/0061454 A1 | 3/2009 | Brody et al. |
| 2009/0186951 A1 | 7/2009 | Brody et al. |
| 2009/0246779 A1 | 10/2009 | Rabinovitch et al. |
| 2009/0311692 A1 | 12/2009 | Brody et al. |
| 2010/0035244 A1 | 2/2010 | Brody et al. |
| 2010/0055689 A1 | 3/2010 | Spira et al. |
| 2011/0053158 A1 | 3/2011 | Mambo et al. |
| 2011/0190150 A1 | 8/2011 | Brody et al. |
| 2011/0217717 A1 | 9/2011 | Brody et al. |
| 2012/0041686 A1 | 2/2012 | Brody et al. |
| 2012/0190567 A1 | 7/2012 | Brody et al. |
| 2012/0288860 A1 | 11/2012 | Van et al. |
| 2012/0322673 A1 | 12/2012 | Brody et al. |
| 2013/0023437 A1 | 1/2013 | Brody et al. |
| 2013/0303826 A1 | 11/2013 | Jurisica et al. |
| 2014/0378425 A1 | 12/2014 | Wilde et al. |
| 2015/0080243 A1 | 3/2015 | Whitney et al. |
| 2015/0088430 A1 | 3/2015 | Whitney et al. |
| 2015/0152474 A1 | 6/2015 | Pawlowski et al. |
| 2015/0232945 A1 | 8/2015 | Brody et al. |
| 2015/0354008 A1 | 12/2015 | Brody et al. |
| 2016/0024583 A1 | 1/2016 | Whitney et al. |
| 2016/0130656 A1 | 5/2016 | Whitney et al. |
| 2017/0226591 A1 | 8/2017 | Brody et al. |
| 2017/0247759 A1 | 8/2017 | Wilde et al. |
| 2017/0328908 A1 | 11/2017 | Brody et al. |
| 2018/0171418 A1 | 6/2018 | Brody et al. |
| 2023/0235401 A1 | 7/2023 | Brody et al. |

FOREIGN PATENT DOCUMENTS

| | | |
|---|---|---|
| WO | WO/1999/060160 A1 | 11/1999 |
| WO | WO 2000/006780 | 2/2000 |
| WO | WO2000/035473 A2 | 6/2000 |
| WO | WO 2001/028428 | 4/2001 |
| WO | WO 2002/006791 | 1/2002 |
| WO | WO 02/44331 | 6/2002 |
| WO | WO 2002/072866 | 9/2002 |
| WO | WO/2002/086443 A2 | 10/2002 |
| WO | WO 2003/015613 | 2/2003 |
| WO | WO 03/040317 A2 | 5/2003 |
| WO | WO/2003/040325 A2 | 5/2003 |
| WO | WO 2003/062389 A2 | 7/2003 |
| WO | WO/2004/005891 A2 | 1/2004 |
| WO | WO 2004/029055 | 4/2004 |
| WO | WO/2004/091511 A2 | 10/2004 |
| WO | WO/2004/111197 A2 | 12/2004 |
| WO | WO/2005/000098 A2 | 1/2005 |
| WO | WO 2005/020784 A2 | 3/2005 |
| WO | WO 2005/047451 * | 5/2005 |
| WO | WO/2005/047451 A2 | 5/2005 |
| WO | WO 2006/056080 | 6/2006 |
| WO | WO/2006/113467 A3 | 10/2006 |
| WO | WO/2007/103541 A2 | 9/2007 |
| WO | WO/2009/039457 A2 | 3/2009 |
| WO | WO/2003/029273 A2 | 4/2009 |
| WO | WO/2009/121070 A1 | 10/2009 |
| WO | WO 2010/054233 | 5/2010 |
| WO | WO 2013/033640 | 3/2013 |
| WO | WO 2013/049152 | 4/2013 |
| WO | WO 2013/163568 | 10/2013 |
| WO | WO 2013/177060 A2 | 11/2013 |
| WO | WO 2014/144564 | 9/2014 |
| WO | WO 2014/186036 | 11/2014 |
| WO | WO 2016/011068 | 1/2016 |
| WO | WO 2017/197335 | 11/2017 |
| WO | WO 2018/009915 | 1/2018 |
| WO | WO 2018/048960 | 3/2018 |

OTHER PUBLICATIONS

Final Office Action Issued in U.S. Appl. No. 16/510,584, dated Feb. 11, 2021.

Abrahamson, et al., Cystatins. Biochem. Soc. Symp. 70: 179-199 (2003).

Anderson, et al., National Vital Statistics Report; 52(9): 1-88 (Nov. 7, 2003).

Anthonisen, et al., Effects of Smoking Intervention and the Use of an Inhaled Anticholinergic Bronchodilator on the Rate of Decline of FEV1. JAMA; 272(19):1497-1505 (Nov. 16, 1994).

Beane, et al., A Prediction Model for Lung Cancer Diagnosis that Integrates Genomic and Clinical Features, Cancer Prev Res 2008, 1:56-64 (2008).

Beane, et al., Reversible and permanent effects of tobacco smoke exposure on airway epithelial gene expression. Genome Biology 2007, 8:R201 (Sep. 25, 2007).

Beer, et al., Gene-expression profiles predict survival of patients with lung adenocarcinoma. Nature Medicine, 8: 816-824 (2002).

Belinksky, et al., Aberrant promoter methylation in bronchial epithelium and sputum from current and former smokers. Cancer Res., 62(8): 2370-7 (2002).

Berman, Jeffrey S, Abstract Immunopathology of the nasal mucosa in sarcoidosis National Institutes of Health Grant No. 1 R21 HL077498-01 (Funding Start Date Sep. 15, 2004).

Beum, et al., Epidermal Growth Factor Downregulates Core 2 Enzymes in a Human Airway Adenocarcinoma Cell Line. Am. J. Respir. Cell Mol. Biol., 29:48-56 (2003).

Bhattacharjee, et al., Classification of human lung carcinoma by mRNA expression profiling reveals distinct adenocarcinoma subclasses. Proc Natl Acad Sci USA, 98(24): 13790-5 (Nov. 20, 2001).

Bild, et al., Oncogenic pathway signatures in human cancers as a guide to targeted therapies. Nature, 439: 353-357 (2006).

Chari, et al., Effect of active smoking on the human bronchial epithelium transcriptome. BMC Genomics, 8:297 (Aug. 29, 2007).

Clark, A., et al., "Altered Protein Kinase C (PKC) Isoforms in Non-Small Cell Lung Cancer Cells: PKCdelta Promotes Cellular Survival and Chemotherapeutic Resistance," *Cancer Research*, 63(4): 780-786 (2003).

Crawford, et al., Normal Bronchial Epithelial Cell Expression of Glutathione Transferase P1, Glutathione Transferase M3, and Glutathione Peroxidase is Low in Subjects with Bronchogenic Carcinoma. Cancer Research, 60: 1609-1618 (Mar. 15, 2000).

Cummings, Sr. et al., Estimating the probability of malignancy in solitary pulmonary nodules. A Bayesian approach, Am Rev Respir Dis 1986; 134:449-52 (1986).

Demeo, et al., The SERPINE2 gene is associated with chronic obstructive pulmonary disease. Am J Hum Genet., 78(2): 253-264 (Feb. 2006).

Denis, et al., RING3 Kinase Transactivates Promoters of Cell Cycle Regulatory Genes through E2F1 Cell. Growth Differ; 11: 417-424 (Aug. 2000).

Doll, R. et al., Mortality in relation to smoking: 40 years' observations on male British doctors. BMJ; 309:901-911 (Oct. 8, 1994).

Ebbert, et al., Lung Cancer Risk Reduction After Smoking Cessation: Observations From a Prospective Cohort of Women. J Clin Oncol; 21(5):921-926 (Mar. 1, 2003).

Fahy, Jv. Remodeling of the Airway Epithelium in Asthma. Am. J. Respir. Crit. Care Med. 164:S46-S51 (2001).

Freeman, et al., DNA from Buccal Swabs Recruited by Mail: Evaluation of Storage Effects on Long-term Stability and Suitability for Multiplex Polymerase Chain Reaction Genotyping, *Behavior Genetics*, 33: 67 (2003).

Garber, et al., Diversity of gene expression in adenocarcinoma of the lung. PNAS, 98(24): 13784-13789 (Nov. 20, 2001).

Garcia-Closas, Collection of Genomic DNA from Adults in Epidemiological Studies by Buccal Cytobrush and Mouthwash, Cancer Epidemiology, Biomarkers and Prevention, 10: 687-696, (2001).

Gebel, et al., Gene expression profiling in respiratory tissues from rats exposed to mainstream cigarette smoke. Carcinogenesis, 25(2): 169-178 (2004).

Golub, et al., Molecular classification of cancer: Class discovery and class prediction by gene expression monitoring, Science, American Association for the Advancement of Science, 286:5439 (Oct. 15, 1999).

Greenlee, et al., Cancer Statistics, 2001. CA Cancer J Clin; 51(1): 15-36 (2001).

(56) References Cited

OTHER PUBLICATIONS

Gurney, JW. Determining the likelihood of malignancy in solitary pulmonary nodules with Bayesian analysis, Part 1, Theory. Radiology 1993;186:405-13 (2005).
Hackett, et al., Variability of antioxidant-related gene expression in the airway epithelium of cigarette smokers. Am J Respir Cell Mol Biol., 29: 331-43 (2003).
Hecht, SS., Tobacco carcinogens, their biomarkers and tobacco-induced cancer. Nature Review Cancer; 3:733-744 (Oct. 2003).
Jang, et al., Activation of melanoma antigen tumor antigens occurs early in lung carcinogenesis. Cancer Research 61: 7959-7963 (2001).
Kanner, et al., Effects of randomized assignment to a smoking cessation intervention and changes in smoking habits on respiratory symptoms in smokers with early chronic obstructive pulmonary disease: the lung health study. American Journal of Medicine; 106:410-416 (1999).
Kao, et al., Tumor-associated Antigen L6 and the Invasion of Human Lung Cancer Cells. Clin Cancer Res. 9:2807-2816 (Jul. 2003).
Katz, et al., Automated detection of genetic abnormalities combined with cytology in sputum is a sensitive predictor of lung cancer, Modern Pathology;21:950-960 (2008).
Kazemi-Noureini, et al., Differential gene expression between squamous cell carcinoma of esophageus and its normal epithelium; altered pattern of mal, akr1c2, and rab11a expression. World J Gastroenterol, 10(12): 1716-1721 (2004).
Kitahara, et al. Alternations of Gene Expression during Colorectal Carcinogenesis Revealed by cDNA Microarrays after Laser-Capture Microdissection of Tumor Tissues and Normal Epithelia. Cancer Research, 61: 3544-3549 (May 1, 2001).
Lander, et al., Initial sequencing and analysis of the human genome. Nature, 409: 860-921 (Feb. 15, 2001).
Li, L., Survival prediction of diffuse large-B-cell lymphoma based on both clinical and gene expression information, Bioinformatics 2006; 22:466-71 (2006).
Liao, et al., Expression and significance of PTEN/PI3K signal transduction-related proteins in non-small cell lung cancer, Ai Zheng 25: 10, p. 1238-42. Abstract (2006).
Liu et al., Effects of physiological versus pharmacological β-carotene supplementation on cell proliferation and histopathological changes in the lungs of cigarette smoke-exposed ferrets. Carcinogenesis, 21: 2245-2253 (2000).
Mannino, DM. et al., Low lung function and incident lung cancer in the United States: data From the First National Health and Nutrition Examination Survey follow-up, Arch Intern Med. 163(12):1475-80 (2003).
Medical News: Targeted, Oral Agent Enzastaurin Shows Favorable Results in Late-Stage Lung Cancer. (Jun. 11, 2007), Retrieved from the Internet <URL: http:/www.medicalnewstoday.com/articles/73761.php>.
Michalczyk, et al., Fresh and cultured buccal cells as a source of mRNA and protein for molecular analysis. Biotechniques. 37(2):262-4, 266-9 (2004).
Miklos, et al., Microarray reality checks in the context of a complex disease. Nature Biotechnology, 22:5 (May 2005).
Miura, et al., Laser capture microdissection and microarray expression analysis of lung adenocarcinoma reveals tobacco smoking- and prognosis-related molecular profiles. Cancer Res., 62(11): 3244-50 (Jun. 1, 2002).
Mongiat, et al., Fibroblast Growth Factor-binding Protein Is a Novel Partner for Perlecan Protein Core. The Journal of Biological Chemistry; 276(13): 10263-10271 (Mar. 30, 2001).
Neubauer, et al., Cure of Helicobacter pylori Infection and Duration of Remission of Low-Grade Gastric Mucosa-Associated Lymphoid Tissue Lymphoma. J. Natl. Cancer Inst., 89(18): 1350-1378 (Sep. 17, 1997).
Okudela, K., et al., "K-ras Gene Mutation Enhances Motility of Immortalized Airway Cells and Lung Adenocarcinoma Cells Via Akt Activation: Possible Contribution to Non-Invasive Expansion of Lung Adenocarcinoma," The American Journal of Pathology, 164(1): 91-100 (2004).
Pittman, J. et al., Integrated modeling of clinical and gene expression information fo personalized prediction of disease outcomes, Proc Natl Acad Sci U S A 2004; 101:8431- (2004).
Potti et al., A Genomic Strategy to Refine Prognosis in Early-Stage Non Small-Cell Lung Cancer, The New England Journal of Medicine 2006; 335(6):570-580 (2006).
Powell, et al., Patterns of allelic loss differ in lung adenocarcinomas of smokers and nonsmokers. Lung Cancer, 39(1): 23-29 (2003).
Powell, et al., Gene expression in lung adenocarcinomas of smokers and nonsmokers. American Journal of Respiratory Cell and Molecular Biology, 29: 157-162 (Aug. 2003).
Proctor RN., Tobacco and the global lung cancer epidemic. Nature Reviews Cancer, 1: 82-86 (Oct. 2001).
Rusznak, et al., Effect of Cigarette Smoke on the Permeability and IL-1B and sICAM-1 Release from Cultured Human Bronchial Epithelial Cells of Never-Smokers, Smokers, and Patients with Chronic Obstructive Pulmonary Disease. Am. J. Respir. Cell Mol. Biol., 23:530-536 (2000).
Saheki, et al., Pathogenesis and pathophysiology of citrin (a mitochondrial aspartate glutamate carrier) deficiency. Metabolic Brain Disease; 17(4):335-346 (Dec. 2002).
Schembri, Frank et al., MicroRNAs as modulators of smoking-induced gene expression changes in human airway epithelium, Proc Natl Acad Sci U S A, 106(7):2319-24 (Feb. 2009).
Shields, PG., Molecular epidemiology of lung cancer. Annals of Oncology, 10(5):S7-S11 (1999).
Shriver, et al., Sex-Specific Expression of Gastrin-Releasing Peptide Receptor: Relationship to Smoking History and Risk of Lung Cancer. J. Natl. Cancer Inst., 92: 24-33 (2000).
Spira, et al., Noninvasive method for obtaining RNA from buccal mucosa epithelial cells for gene expression profiling. Biotechniques, 36(3): 484-7 (2004).
Spira, et al., Effects of cigarette smoke on the human airway epithelial cell transcriptome, PNAS, 101: 27, p. 10143-10148 (Jul. 6, 2004).
Spira, et al., Airway epithelial gene expression in the diagnostic evaluation of smokers with suspect lung cancer. Nature Medicine 13: 361-366 (2007).
Spira, et al., Gene Expression Profiling of Human Lung Tissue from Smokers with Severe Emphysema. Am J Respir Cell Mol Biol., 31(6):601-10 (2004).
Spira, et al., Impact of cigarette smoke on the normal airway transcriptome. Chest. 125 (5 Suppl):115S (May 2004).
Spira, Avrum E., Abstract The airway transcriptome as a biomarker for lung cancer National Institutes of Health Grant No. 1 R21 CA106506-01 (Funding Start Date Aug. 9, 2005).
Spira, Avrum E., Abstract Airway gene expression in smokers: an early diagnostic biomarker for lung cancer National Institutes of Health Grant No. 1 R01 CA124640-01 (Funding Start Date May 1, 2007).
Spivack, et al., Gene-environment interaction signatures by quantitative mRNA profiling in exfoliated buccal mucosal cells, Cancer Research, 64: 18, p. 6805-6813 (2004).
Sridhar, et al. Smoking-induced gene expression changes in the bronchial airway are reflected in nasal and buccal epithelium. BMC Genomics, 9: 259 (May 2008).
Stephenson, AJ et al., Integration of gene expression profiling and clinical variables to predict prostate carcinoma recurrence after radical prostatectomy, Cancer 2005; 104:290-8 (2005).
Stewart, JH. Lung Carcinoma in African Americans, A Review of the Current Literature. Cancer; 91(12): 2476-2482 (Jun. 15, 2001).
Swensen, SJ et al., The probability of malignancy in solitary pulmonary nodules. Application to small radiologically indeterminate nodules, Arch Intern Med 1997; 157:849-55 (1997).
Swensen, SJ et al., Abstract Solitary pulmonary nodules: clinical prediction model versus physicians, Mayo Clinic Proc 1999; 74:319-29 (1999).
Theocharis, et al., Metallothionein: a multifunctional protein from toxicity to cancer. Int Biol Markers, 18(3): 162- 169 (2003).

(56) References Cited

OTHER PUBLICATIONS

Thurston, SW et al., Modeling lung cancer risk in case-control studies using a new dose metric of smoking, Cancer Epidemiol Biomarkers Prev 2005; 14(10): 2296-302 (2005).
Trunk, G et al., The management and evaluation of the solitary pulmonary nodule, Chest 1974; 66:236-9 (1974).
Ung, YC et al., Fluorodeoxyglucose positron emission tomography in the diagnosis and staging of lung cancer: a systematic review, J Nat'l Cancer Institute, 99(23): 1753-67 (2007).
Volm, et al., Prognostic significance of the expression of c-fos, c-jun and c-erbB-1 oncogene products in human squamous cell lung carcinomas. J Cancer Res Clin Oncol, 119: 507-510 (1993).
Wahidi, MM et al., Evidence for the treatment of patients with pulmonary nodules: when is it lung cancer? ACCP evidence-based clinical practice guidelines 2nd Edition, Chest 2007; 132:94-107S (2007).
West, M., et al. Embracing the complexity of genomic data for personalized medicine, Genome Res 2006; 16:559-66 (2006).
Wistuba, et al., Molecular damage in the bronchial epithelium of current and former smokers. J Natl Cancer Inst., 89(18): 1366-73 (Sep. 17, 1997).
Wistuba, et al., High resolution chromosome 3p allelotyping of human lung cancer and preneoplastic/preinvasive bronchial epithelium reveals multiple, discontinuous sites of 3p allele loss and three regions of frequent breakpoints. Cancer Res., 60(7): 1949-60 (Apr. 1, 2000).
Zeeberg, et al.. GoMiner: a resource for biological interpretation of genomic and proteomic data. Genome Biology, 4(4):R28.1-R28.8 (2003).
Zhang, et al. Comparison of smoking-induced gene expression on Affymetrix Exon and 3'- based expression arrays. Genome Inform. 18: 247-57 (2007).
Retracted in Jan. 2011—Potti, A., et al., "Genomic Signatures to Guide the Use of Chemotherapeutics," Nature Medicine, 12(11): 1294-1300 (2006). (Retracted in Jan. 2011—Potti, A., et al., "Genomic Signatures to Guide the Use of Chemotherapeutics," Nature Medicine, 12(11): 1294-1300 (2006).).
Ambion, Inc. "GeneAssist Pathway Atlas for P13K Signaling," Accessed from http://www5.appliedbiosystems.com/tools/pathway/pathway_proteins.php?pathway=P13K on May 3, 2011.
Arimura, et al. Elevated Serum β-Defensins Concentrations in Patients with Lung Cancer, Anticancer Research, 24: 4051-4058 (2004).
Baker, Stuart. "The Central Role of Receiver Operating Characteristic (ROC) Curves in Evaluating Tests for the Early Detection of Cancer," *Journal of the National Cancer Institute*, 95(7): 511-515 (2003).
Braakhuis, et al. "A Genetic Explanation of Slaughter's Concept of Field Cancerization Evidence and Clinical Implications," *Cancer Research*, 63: 1727-1730 (2003).
Chan, et al. Integrating Transcriptomics and Proteomics, *Genomics & Proteomics Magazine*, 6(3), text of article reprinted and accessed from www.dddmag.com on May 27, 2005.
Chen, et al. "Discordant Protein and mRNA Expression in Lung Adenocarcinomas," *Molecular and Cellular Proteomics*, 1: 304-313 (2001).
Dauletbaev, et al. "Expression of Human Beta Defensin (HBD-1 and HBD-2) mRNA in Nasal Epithelia of Adult Cystic Fibrosis Patients, Healthy Individuals, and Individuals with Acute Cold," *Respiration*, 69:46-51 (2002).
Franklin, et al. "Widely Dispersed p53 Mutation in Respiratory Epithelium," *The Journal of Clinical Investigation*, 100(8): 2133-2137 (1997).
Hellmann, et al. "Gene Profiling of Cultured Human Bronchia Epithelial and Lung Cacinoma Cells," *Toxicological Sciences*, 61: 154-163 (2001).
Ikeda, et al. "Malignancy associated changes in bronchial epithelial cells and clinical application as a biomarker," *Lung Cancer*, 19(3): 161-166 (1998).

Kraft, et al. "Expression of epithelial markers in nocturnal asthma," *Journal of Allergy and Clinical Immunology*, 102(3): 376-381 (1998).
Liu, et al. "Quantitative Proteome Analysis Reveals Annexin A3 as a Novel Biomarker in Lung Adenocarcinoma," *Journal of Pathology*, 217: 54-64 (2009).
Reynolds, et al. "Pre-protachykinin-A mRNA is increased in the airway epithelium of smokers with chronic bronchitis." *Respiratory*, 6:187-197 (2001).
Riise, et al. "Bronchial Brush Biopsies for Studies of Epithelial Inflammation in Stable Asthma and Nonobstructive Chronic Bronchitis," *European Respiratory Journal*, 9: 1665- 1671 (1996).
Slonim, Donna. "From Patterns to Pathways: Gene Expression Data Analysis Comes of Age," *Nature Genetics Supplement*, 32: 502-508 (2002).
Takizawa, et al. "Increased expression of transforming growth factor-betal in small airway epithelium from tobacco smokers and patients with chronic obstructive pulmonary disease (COPD)," *American Journal of Respiratory and Critical Care Medicine*, 163:1476-1483 (2001).
Watters, et al. "Developing Gene Expression Signatures of Pathway Deregulation in Tumors," *Molecular Cancer Therapeutics*, 5: 2444-2449 (2006).
Ohtsuka, et al., "ADAM28 is overexpressed in human non-small cell lung carcinomas and correlates with cell proliferation and lymph node metastasis," *International Journal of Cancer*, 118(2): 263-273 (2006).
Hamilton and Sharp, "Diagnosis of lung cancer in primary care: a stmctured review," *Family Practice*, 21(6), 605-611 (2004).
AkitaA, et al., "Molecular Biology of Lung Cancer, " *The Journal of the Japanese Respiratory Society*, 42(5): (2004).
Printout from database NCBI GEO accession no. GSE4115 [Online] NCB, dated Feb. 27, 2006.
Brody, Jerome S., Abstract "Airway epithelial gene expression in COPD" National Institutes of Health Grant No. 1 R01 HL071771-01 (Funding Start Date Sept. 30, 2002).
Kiss, et al., "Anatomisk Atlas over Manniskokroppen, band II," Natur och Kultur Stockholm, Stockholm, Sweden ISBN: 91-27-67278-6.
Bohula et al., "The Efficacy of Small Interfering RNAs Targeted to the Type 1 Insulin-like Growth Factor Receptor (IGF1R) Is Influenced by Secondary Structure in the IGF1R Transcript," The Journal of Biological Chemistry 278(18): 15991-15997 (2003).
Wardlaw, et al., "Effect of Cigarette smoke on CYP1A1, CYP1A2 and CYP2B1/2 of nasal mucosae in F344 rats," Carcinogenesis 19(4): 655-662 (1998).
Lin, et al., "Effects of Dexarnethasone on Acute Lung Injury Rat Cells Signal Transduction Systems ERK and PI3-K," Medical Journal of Chinese People's Liberation Army 6(31): 592-594 (2006).
Guajardo, et al., "Altered gene expression profiles in nasal respiratory epithelium reflect stable versus acute childhood asthma", J. Allergy Clin Immunol 115(2): 243-251 (2005).
Voynow, et al., "Mucin Gene Expression (MUC1, MUC2, and MUC5/5AC) in Nasal Epithelial Cells of Cystic Fibrosis, Allergic Rhinitis, and Normal Individuals", Lung 176: 345-354 (1998).
Shah et al., "SIEGE: Smoking Induced Epithelial Gene Expression Database", Nucleic Acids Research, 33: D573-D579 (2005).
Enard et al., "Intra- and Interspecific Variation in Primate Gene Expression Patterns", Science 296: 340-343 (2002).
Cheung, et al., "Natural variation in human gene expression assessed in lymphoblastoid cells", Nature Genetics, 33: 422-425 (2003).
Wu, Thomas D., "Analysing gene expression data from DNA microarrays to identify candidate genes", Journal of Pathology, 195:53-65 (2001).
Newton, et al., "On Differential Variability of Expression Ratios: Improving Statistical Inference about Gene Expression Changes from Microarray Data", Journal of Computational Biology, 8: 37-52 (2001).
Fritz, et al., "Nasal mucosal gene expression in patients with allergic rhinitis with and without nasal polyps", Journal of Allergy Clin. Immunol, 112(6): 1057-1063 (2003).

(56) References Cited

OTHER PUBLICATIONS

Lam, et al., "A Phase I Study of myo-Inositol for Lung Cancer Chemoprevention", Cancer Epidemiology, Biomarkers & Prevention 15(8): 1526-1531 (2006).
Peluso, et al., "Comparison of DNA adduct levels in nasal mucosa, lymphocytes and bronchial mucosa of cigarette smokers and interaction with metabolic gene polymorphisms", Carcinogenesis 25(12): 2459-2465 (2004).
Marinov, et al., "Targeting mTOR signaling in lung cancer", Critical Reviews in Oncology/Hematology 63: 172-182 (2007).
Singhal, et al., "Alterations in Cell Cycle Genes in Early Stage Lung Adenocarcinoma Identified by Expression Profiling", Cancer Biology & Therapy 2(3): 291-299 (2003).
Zhang, et al., "Similarities and Differences Between Smoking-Related Gene Expression in Nasal and Bronchial Epithelium," *Physiol. Genomics*, 41:1-8, (2010).
Danel, et al., "Quantitative assessment of the epithelial and inflammatory cell populations in large airways of normal and individuals with cystic fibrosis," American Journal of Respiratory and Critical Care Medicine 153(1): 362-368 (1996).
Merriam-Webster.com (htpp://www.merriam-webster.com/dictionary/questionnaire, downloaded Oct. 26, 2013).
Tarca, et al., "Analysis of microarray experiments of gene expression profiling," American Journal of Obstetrics and Gynecology 195(2): 373-388 (2006).
May, "How many species are there on earth?" Science 241(4872): 1441-1449 (1988).
Benner, et al. "Evolution, language and analogy in functional genomics," Trends in Genetics 17(7): 414-418 (2001).
Modrek, et al., "Genome-wide detection of alternative splicing in expressed sequences of human genes," Nucleic Acids Research 29(13): 2850-2859 (2001).
Woenckhaus, et al., "Smoking and cancer-related gene expression in bronchial epithelium and non-small-cell lung cancers," The Journal of Pathology 210(2): 192-204 (2006).
Details for HG-U133A:202831_AT (https://www.affymetrix.com/analysis/netaffx/fullrecord.affx?pk=HG-U133A:202831_AT, downloaded Dec. 10, 2012).
Details for HG-U133A:210519_S_AT (https://www.affymetrix.com/analysis/netaffx/fullrecord.affx?pk=HG-U133A:210519_S_AT downloaded Dec. 10, 2012).
HG-U133a-207469_S_AT (https:www/affymetrix.com/analysis/netaffx/fullrecord.affx?pk=HG-U133A:207469_S_AT, downloaded Dec. 10, 2012.
HG-U133A:823_AT (https://www.affymetrix.com/analysis/netaffx/fullrecord.affx?pk=HG-U133A:823_AT, downloaded Dec. 10, 2012.
Demoly, et al., "c-fos Proto-oncogene Expression in Bronchial Biopsies of Asthmatics," American Journal of Respiratory Cell and Molecular Biology 7:128-133 (1992).
Hennessy, et al., "Exploiting the PI3K/AKT Pathway for Cancer Drug Discovery," Nature, vol. 4: 988-1004 (2005).
Langford, et al., "Is the Property of Being Positively Correlated Transitive," The American Statistician 55(4): 322-325 (2001).
Saal, et al., "Poor Prognosis in Carcinoma is Associated with A Gene Expression Signature of Aberrant PTEN Tumor Suppressor Pathway Activity," PNAS 104(18): 7564-7569 (2007).
Sotos, et al., "The Transitivity Misconception of Pearson's Correlation Coefficient," Statistics Education Research Journal 8(2): 33-55 (2009).
Thisted, Ronald A. "What is a P-value", Departments of Statistics and Health Studies, The University of Chicago, May 25, 1988.
Tichelaar, et al., "Increased Staining for Phospho-Akt, p65/RELA and cIAP-2 in Pre-neoplastic Human Bronchial Biopsies," BMC Cancer 5(155): 1-13 (2005).
Tsao, et al, "Increased Phospho-AKT (Ser$^{473}$)Expression in Bronchial Dysplasia: Implications for Lunch Cancer Prevention Studies," Cancer, Epidemiology, Biomarkers & Prevention 12:660-664 (2003).

West, et al, "Rapid Akt Activation by Nicotine and Tobacco Carcinogen Modulates the Phenotype of Normal Human Airway Epithelial Cells," The Journal of Clinical Investigation 111(1): 81-90 (2003).
Hoshikawa, et al., "Hypoxia induces difference genes in the lungs of rats compared with mice," Physiol Genomics 12: 209-219 (2003).
Cheng, et al., "Reduced expression levels of nucleotide excision repair genes in lung cancer: a case-control analysis," Carcinogenesis 21(8): 1527-1530 (2000).
Fielding, et al., "Heterogeneous Nuclear Ribonucleoprotein A2/B1 Up-Regulation in Bronchial Lavage Specimens: A Clinical Marker of Early Lung Cancer Detection," Clinical Cancer Research 5:4048-4052 (1999).
Yu-Rong, et al., "Tumor associated antigen L6 and the invasion of human lung cancer cells." Clinical Cancer Research 9(7): 2807-16 (2003).
Dempsey, et al., "Lung disease and PKCs," Pharmacological Research 55(6): 545-59 (2007).
MacKay et al., "Targeting the protein kinase C family: are we there yet?" Nature Reviews Cancer 7(7): 554-62 (2007).
Gustafson, et al., "Airway PI3K Pathway Activation Is an Early and Reversible Even in Lung Cancer Developrnent," www.ScienceTransmlationMedicine.org 2(26) (2010).
Fukumoto, et al., "Overexpression of the Aldo-Keto Reductase Family Protein AKR1B10 is Highly Correlated with Smokers' Non-Small Cell Lung Carcinomas," Clinical Cancer Research 11:1776-1786 (2005).
Whitehead et al., "Variation in tissue-specific gene expression among natural populations," Genome Biology 6(2):R13.1-R13.14 (2005).
Brambilla, et al., "Advances in Brief p53 Mutant Immunophenotype and Deregulation of p53 Transcription Pathway (Bcl2, Bax, and Waft) in Precursor Bronchial Lesions of Lung Cancer1", *Clinical Cancer Research*, 4: 1609-1618 (1998).
Demuth, et al., "The gene expression index c-rnyc x E2F-1/p21 is highly predictive of malignant phenotype in human bronchial epithelial cells", *American Journal of Respiratory Cell and Molecular Biology*, 19: 18-24 (1998).
Hirsch, et al., "Early Detection of Lung Cancer: Clinical Perspectives of Recent Advances in Biology and Radiology 1", *Clinical Cancer Research*, 7: 5-22 (2001).
Lacroix, et al., "Sensitive detection of rare cancer cells in sputum and peripheral blood samples of patients with lung cancer by preproGRP-specific RT-PCR", International Journal of Cancer, 92(1): 1-8 (2001).
Willey, et al., "Quantitative RT-PCR Measurement of Cytochromes p450 1A1, 1B1, and 2B7, Microsomal Epoxide Hydrolase, and NADPH Oxidoreductase Expression in Lung Cells of Smokers and Nonsmokers," Am. J. Respir. Cell Mol. Biol., 1997, 17:114-124.
Mollerup, et al., "Sex Differences in Lung CYP1A1 Expression and DNA Adduct Levels among Lung Cancer Patients," Cancer Research, 1999, 59: 3317-3320 (1999).
Saito-Hisaminato, "Genome-Wide Profiling of Gene Expression in 29 Normal Human Tissues with a cNDA Microarray," DNA Research, 2002, 9:35-45.
Details for HG-U133A:217291 _AT (CEACAM5) (https://www.affymetrix.com/analysis/netaffx/fullrecord.affx?pk=HG-U133A:217291 _AT, downloaded Apr. 22, 2016).
St. Croix, et al., "Genes Expressed in Human Tumor Endothelium," *Science*, 289:1197-1202, (Aug. 18, 2000).
Moller, et al., "Altered ratio of endothelin ETA- and ETB receptor mRNA in bronchial biopsies from patients with asthma and chronic airway obstruction," Eur. Journal of Pharmacology, 365:R1-R3, (1999).
Wojnarowski et al., "Cytokine expression in bronchial biopsies of cystic fibrosis patients with and without acute exacerbation," Eur. Respir. J., 14:1136-1144, (1999).
Anbazhagan, et al., "Classification of Small Cell Lung Cancer and Pulmonary Carcinoid by Gene Expression Profiles," *Cancer Research*, 59:5119-5122, (Oct. 15, 1999).
Chen, et al., "Up-regulations of Tumor Interleukin-8 Expression by Infiltrating Macrophages: Its Correlation with Tumor Angiogenesis

(56) References Cited

OTHER PUBLICATIONS and Patient Survival in Non-Small Cell Lung Cancer," *Clinical Cancer Research*: pp. 729-737, (Feb. 1, 2003).

Grepmeier, et al., "Deletions at Chromosome 2q and 12p are Early Frequent Molecular Alterations in Bronchial Epithelium and NSCLC of Long-Term Smokers." *Int J Oncol.*, 27(2):481-8, (2005).

Khan, et al., "Classification and Diagnostic Prediction of Cancers Using Gene Expression Profiling and Artificial Neural Networks," *Nature Medicine*, 7(6):673-679, (Jun. 2001).

Yoneda, et al., "Development of High-Density DNA Microarray Membrane for Profiling Smoke-and Hydrogen Peroxide-Induced Genes in a Human Bronchial Epithelial Cell Line," *American Journal of Respiratory and Critical Care Medicine*, 164:S86-S89, (2001).

Notterman, et al., "Tumor Biology and Microarray Analysis of Solid Tumors: Colorectal Cancer as a Model System," *Microarrays and Cancer Research*, Warrington et al.(eds.), Eaton Publishing, Westborough, MA, pp. xi-xvi, (2002).

Strausberg, et al., "Reading the Molecular Signatures of Cancer," *Microarrays and Cancer Research*, Warrington et al. (eds.), Eaton Publishing, Westborough, MA, pp. 81-111, (2002).

Zochbauer-Muller, et al., "5' CpG Island Methylation of the FHIT Gene is Correlated with Loss of Gene Expression in Lung and Breast," *Cancer Research*, 61:3581-3585, (May 2, 2001).

Cooper, "Gene Expression Studies in Lung Cancer," *The Molecular Genetics of Lung Cancer*, pp. 167-186, (2005).

Deng, et al., "Ubiquitous Induction of Resistance to Platinum Drugs in Human Ovarian, Cervical, Germ-Cell and Lung Carcinoma Tumor Cells Overexpressing Isoforms 1 and 2 of Dihydrodiol Dehydrogenase," *Cancer Chemother. Pharmacol.*, 54:301-307, (2004).

Schulz, et al., "Activation of Bronchial Epithelial Cells in Smokers Without Airway Obstruction and Patients with COPD," *Chest*, 125(5):1706-1713, (May 2004).

Su, et al., "Molecular Classification of Human Carcinomas by Use of Gene Expression Signatures," *Cancer Research*, 61:7388-7393, (Oct. 15, 2001).

Yang, et al., "Reduction of Dihydrodiol Dehydrogenase Expression in Resected Hepatocellular Carcinoma," *Oncol. Rep.*, 10(2):271-276, Abstract pp. 1-2 (2003).

Kuriakose, et al., "Selection and Validation of Differentially Expressed Genes in Head and Neck Cancer," CMLS, 61:1372-1383, (2004).

Sugita, et al., "Combined Use of Oligonucleotide and Tissue Microarrays Identifies Cancer/Testis Antigens as Biomarkers in Lung Carcinoma," Cancer Research, 62:3971-3979, (Jul. 15, 2002).

Vartiainen, et al., "Validation of Self-Reported Smoking by Serum Cotinine Measurement in a Community-Based Study," *J. Epidemiol Community Health*, 56:167-170, (2002).

Beane-Ebel, "Single-Cell RNA Sequencing of the Bronchial Epithelium in Smokers With Lung Cancer," U.S. Army Medical Research and Material Command. Jul. 1, 2016 [retrieved on Sep. 19, 2017]. Retrieved from the Internet at http://www.dtic.mil/dtic/tr/fulltext/u2/a624219.pdf.

Coleman, "Of Mouse and Man—What is the Value of the Mouse in Predicting Gene Expression in Humans?" Drug Discovery Today, 8(6):233-235, (Mar. 2003).

Durham, et al., "The Relationship Between COPD and Lung Cancer," Lung Cancer, 90:121-127, (2015).

Kocarnik, et al., "Replication of Associations Between GWAS SNPs and Melanoma Risk in the Population Architecture Using Genomics and Epidemiology (PAGE) Study," Journal of Investigative Dermatology, 134:2049-2052, (Feb. 27, 2014).

Ooi, et al., "Molecular Profiling of Premalignant Lesions in Lung Squamous Cell Carcinomas Identifies Mechanisms Involved in Stepwise Carcinogenesis," Cancer Prevention Research, 7(5):487-495, (Mar. 11, 2014).

Anonymous: "Bronchogenic carcinoma is a malignant neoplasm of the lung arising from the epithelium of the bronchus or bronchiole", Apr. 22, 2003 (Apr. 22, 2003), retrieved from the internet: URL:http://www.meddean.luc.edu/lumen/meded/medicine/pulmonar/pathms/path19.htm [retrieved on Feb. 13, 2019].

Brenner, Sydney, et al. "Gene expression analysis by massively parallel signature sequencing (MPSS) on microbead arrays." Nature biotechnology 18.6 (2000): 630.

Gerrein, J., et al., "/Poster Discussion Session/ Sunday, May 18 / 2:00 -4:30 PM / Room 30 A-B (Upper Level) San A107 The Lung's Silver Lining: Airway and Alveolar Epithelial Biology Leveraging Gene Expression in the Bronchial Airway to Develop a Nasal Biomarker for Early Detection of Lung Cancer," retrieved from the Internet: URL:https://www.atsjournals.org/doi/pdf/10.1164/ajrccm-conference.2014.189.1_MeetingAbstract.A2362 (2014).

Chen, et al., "Expression of dihydrodiol dehydrogenase in the resected stage I non-small cell lung cancer," Oncology Reports, vol. 9, No. 3, May 1, 2002, pp. 515-519.

Hsu, et al., "Overexpression of dihydrodiol dehydrogenase as a prognostic maker of non-small cell lung cancer," Cancer Research vol. 6, No. 6, Mar. 15, 2001, pp. 2727-2731.

Shibuya, Kiyoshi, et al. "Increased telomerase activity and elevated hTERT mRNA expression during multistage carcinogenesis of squamous cell carcinoma of the lung." Cancer 92.4 (2001): 849-855.

Tockman, Melvyn S., et al. "Considerations in bringing a cancer biomarker to clinical application." Cancer Research 52.9 Supplement (1992): 2711s-2718s.

Anonymous: "Bronchogenic carcinoma / definition of bronchogenic carcinoma by Medical dictionary," Feb. 13, 2019 (Feb. 13, 2019), retrieved from the internet: URL:https://medical-dictionary.thefreedictionary.com/bronchogenic+carcinoma [retrieved on Feb. 13, 2019].

Spira, et al., Translating Airway Gene Expression into Biomarkers for Tobacco Smoke Exposure and Lung Cancer Detection Smoking and the Airway "field of Injury" as a Paradigm.Retrieved from the internet: URL: https://www.epa.gov/sites/production/files/2014-07/documents/spiraavrum_epa_dec_2012.pdf.

Affymetrix Show Results SULF1 (http://www.affymetrix.com/analysis/netaffx/showresults.affx, downloaded Jul. 6, 2020).

Iacobuzio-Donahue, Christine A., et al. "Highly expressed genes in pancreatic ductal adenocarcinomas: a comprehensive characterization and comparison of the transcription profiles obtained from three major technologies." Cancer research 63.24 (2003): 8614-8622.

Powell, Charles A., et al. "Loss of heterozygosity in epithelial cells obtained by bronchial brushing: clinical utility in lung cancer." Clinical Cancer Research 5.8 (1999): 2025-2034.

Gorringe, Kylie L. "Loss of heterozygosity." eLS (2016): 1-8.

Jung, et al. (Korean Journal of Medicine, 2002, 62(1): 58-68).

British Thoracic Society Bronchoscopy Committee (Thorax, 2001) 56 (suppl): i1-i21.

Tjard Van Heek et al., (Cancer Biology & Therapy, 2004 3(7): 651-656).

International Search Report for PCT/US2017/032517, dated Oct. 2, 2017.

International Search Report for PCT/US2017/041267, dated Dec. 15, 2017.

European Search Report in Application EP 10 18 4732, dated Mar. 21, 2011.

European Search Report in Application EP 10 18 4813, dated Mar. 21, 2011.

European Search Report in Application EP 10 18 4888, dated Mar. 21, 2011.

European Search Report in Application EP 04 81 0818, dated Oct. 28, 2010.

European Search Report in Application EP 08 83 2403, dated Oct. 22, 2010.

European Search Report in Application EP 09 72 4548, dated Jun. 16, 2011.

European Search Report for European Application No. EP 10195816, dated Oct. 13, 2011.

European Search Report in Application EP 12 17 0635, dated Apr. 22, 2013.

Chinese Search Report in Application 2008801147951 dated Aug. 24, 2012.

Extended European Search Report from EP 16186152.1, dated May 31, 2017.

(56) References Cited

OTHER PUBLICATIONS

European Search Report for European Application No. EP 17185133.0, dated Feb. 21, 2018.
Supplementary European Search Report for European Application No. EP 17 79 6983, dated Feb. 3, 2020.
European Search Report EP10195822 dated Jun. 20, 2011.
European Search Report EP10195803 dated Jun. 20, 2011.
Non-Final Office Action for U.S. Appl. No. 12/234,588, dated Jun. 27, 2011.
Non-Final Office Action for U.S. Appl. No. 10/579,376, dated Jul. 9, 2008.
Non-Final Office Action for U.S. Appl. No. 12/884,714, dated Sep. 23, 2011.
Final Office Action for U.S. Appl. No. 12/234,588, dated Nov. 4, 2011.
Non-Final Office Action for U.S. Appl. No. 12/414,555, dated Nov. 30, 2011.
Final Office Action for U.S. Appl. No. 12/414,555, dated Mar. 15, 2012.
Non-Final Office Action for U.S. Appl. No. 13/346,444, dated Dec. 12, 2012.
Non-Final Office Action for U.S. Appl. No. 12/234,588, dated Mar. 28, 2014.
Final Office Action for U.S. Appl. No. 13/346,444, dated Nov. 27, 2013.
Non-Final Office Action for U.S. Appl. No. 11/294,834, dated Jan. 29, 2014.
Non-Final Office Action for U.S. Appl. No. 14/584,960, dated Apr. 27, 2016.
Final Office Action for U.S. Appl. No. 13/524,749, dated Apr. 3, 2014.
Final Office Action for U.S. Appl. No. 13/323,655, dated Jul. 17, 2014.
Final Office Action for U.S. Appl. No. 11/294,834, dated Aug. 22, 2016.
Non-Final Office Action for U.S. Appl. No. 11/294,834, dated Dec. 15, 2015.
Non-Final Office Action for U.S. Appl. No. 11/294,834, dated Jun. 24, 2008.
Non-Final Office Action for U.S. Appl. No. 13/323,655, dated Apr. 9, 2013.
Non-Final Office Action for U.S. Appl. No. 13/524,749, dated Sep. 9, 2013.
Final Office Action for U.S. Appl. No. 11/294,834 dated Aug. 18, 2014.
Non-Final Office Action for U.S. Appl. No. 13/323,655 dated Nov. 7, 2013.
Non-Final Office Action for U.S. Appl. No. 11/294,834, dated Jul. 29, 2014.
Non-Final Office Action for U.S. Appl. No. 14/613,210, dated Dec. 6, 2016.
Final Office Action for U.S. Appl. No. 14/500,475, dated Feb. 28, 2017.
Final Office Action for U.S. Appl. No. 14/613,210, dated Apr. 3, 2017.
Non-Final Office Action for U.S. Appl. No. 15/439,791, dated Jun. 14, 2017.
Final Office Action for U.S. Appl. No. 14/500,475, dated Aug. 2, 2017.
Notice of Allowance for U.S. Appl. No. 14/613,210, dated Oct. 31, 2017.
Non-Final Office Action for U.S. Appl. No. 15/644,721, dated Dec. 27, 2017.
Final Office Action for U.S. Appl. No. 15/439,891, dated Feb. 14, 2018.
Non-Final Office Action for U.S. Appl. No. 14/500,475, dated Mar. 26, 2018.
Non-Final Office Action for U.S. Appl. No. 14/690,182, dated Apr. 20, 2018.
Non-Final Office Action for U.S. Appl. No. 15/336,469, dated Apr. 10, 2018.
Non-Final Office Action for U.S. Appl. No. 15/888,831, dated Mar. 27, 2018.
Final Office Action for U.S. Appl. No. 15/644,721, dated Jun. 20, 2018.
Final Office Action for U.S. Appl. No. 15/888,831, dated Jul. 24, 2018.
Final Office Action for U.S. Appl. No. 15/336,469, dated Oct. 9, 2018).
Final Office Action for U.S. Appl. No. 14/690,182, dated Oct. 9, 2018.
Non-Final Office Action for U.S. Appl. No. 15/439,891, dated Dec. 28, 2018.
Non-Final Office Action for U.S. Appl. No. 14/690,182, dated Mar. 22, 2019.
Non-Final Office Action for U.S. Appl. No. 15/888,831, dated Mar. 27, 2019.
Non-Final Office Action for U.S. Appl. No. 15/644,721, dated Mar. 7, 2019.
Final Office Action for U.S. Appl. No. 14/500,475, dated May 14, 2019.
Final Office Action for U.S. Appl. No. 15/439,891, dated Jun. 18, 2019.
Final Office Action for U.S. Appl. No. 15/888,831, dated Oct. 10, 2019.
Notice of Allowance for U.S. Appl. No. 14/500,475, dated Oct. 15, 2019.
Non-final Office Action for U.S. Appl. No. 15/336,469 dated Dec. 4, 2019.
Non-Final Office Action for U.S. Appl. No. 16/510,584 dated Jan. 16, 2020.
Notice of Allowance issued in U.S. Appl. No. 15/888,831, dated Feb. 20, 2020.
Final Office Action for U.S. Appl. No. 16/510,584, dated Apr. 23, 2020.
Final Office Action for U.S. Appl. No. 15/336,469, dated Jul. 10, 2020.
Notice of Allowance issued in U.S. Appl. No. 15/888,831, dated Jun. 1, 2020.
Non-Final Office Action issued in U.S. Appl. No. 16/810,827, dated Aug. 10, 2020.
Notice of Allowance issued in U.S. Appl. No. 15/644,721, dated Sep. 30, 2020.
Non-Final Office Action Issued in U.S. Appl. No. 16/510,584, dated Sep. 30, 2020.
Non-Final Office Action Issued in U.S. Appl. No. 16/300,947, dated Oct. 22, 2020.
Final Office Action Issued in U.S. Appl. No. 16/810,827, dated Nov. 23, 2020.).
Korn, S. H., et al. "Glucocorticoid receptor mRNA levels in bronchial epithelial cells of patients with COPD: influence of glucocorticoids." Respiratory medicine 92.9 (1998): 1102-1109.
Hindiyeh, Musa, et al. "Evaluation of a multiplex real-time reverse transcriptase PCR assay for detection and differentiation of influenza viruses A and B during the 2001-2002 influenza season in Israel." Journal of clinical microbiology 43.2 (2005): 589-595.
Li, Jin, et al. "The cystic fibrosis transmembrane conductance regulator as a biomarker in non-small cell lung cancer." International journal of oncology 46.5 (2015): 2107-2115.
Mak, Victor. Expression of CFTR mRNA in nasal epithelium and vas deferens. Diss. 1999.
Tokunaga, Katsuo, et al. "Enhanced expression of a glyceraldehyde-3-phosphate dehydrogenase gene in human lung cancers." Cancer Research 47.21 (1987): 5616-5619.
Weng, Ching-Fu, et al. "Association between the risk of lung cancer and influenza: A population-based nested case-control study." International Journal of Infectious Diseases 88 (2019): 8-13.
Wong, SC Cesar, et al. "Development of a quantitative assay for SARS coronavirus and correlation of GAPDH mRNA with SARS coronavirus in clinical specimens." Journal of clinical pathology 58.3 (2005): 276-280.

(56) References Cited

OTHER PUBLICATIONS

Zabner, Joseph, et al. "Comparison of DNA-lipid complexes and DNA alone for gene transfer to cystic fibrosis airway epithelia in vivo." The Journal of clinical investigation 100.6 (1997): 1529-1537.
Non-Final Office Action issued in U.S. Appl. No. 16/810,827, dated Apr. 22, 2021.
Final Office Action issued in U.S. Appl. No. 15/336,469, dated Jun. 25, 2021.
Non-Final Office Action issued in U.S. Appl. No. 16/751,145 dated Aug. 18, 2021.
Non-Final Office Action issued in U.S. Appl. No. 16/510,584 dated Aug. 25, 2021.
Non-Final Office Action issued in U.S. Appl. No. 16/810,827 dated Aug. 23, 2021.
Pirooznia, Mehdi, et al. "A comparative study of different machine learning methods on microarray gene expression data." *BMC genomics* 9.1 (2008): 1-13.
Bertone, Paul, and Mark Gerstein. "Integrative data mining: the new direction in bioinformatics." *IEEE Engineering in Medicine and Biology Magazine* 20.4 (2001): 33-40.
Details for HT_HG-U133A:212344_AT (Affymetrix Expression Probeset Details, downloaded Mar. 1, 2022).
Non-Final Office Action issued in U.S. Appl. No. 16/657,816 dated May 11, 2022.
Non-Final Office Action issued in U.S. Appl. No. 15/336,469, dated Mar. 8, 2022.
Non-Final Office Action from U.S. Appl. No. 16/657,816, dated May 11, 2022.
Woenckhaus, et al., "Expression Profiling of Non-Small Cell Lung Cancers and Bronchi of Smokers and Non Smokers," Study Group: Molecular Pathology/Pathology—Research and Practice, 200:p. 255, (2004).
Bankovic, et al., "Identification of genes associated with non-small-cell lung cancer promotion and progression", Lung Cancer, vol. 67, No. 2, (2010), pp. 151-159.
Picozzi, et al., "Genomic organization and transcription of the human retinol dehydrogenase 10 (RDH10) gene", Febs Letters, vol. 554, (2003), pp. 59-66.
Dubinett, et al. Abstract "The UCLA-Boston University Lung Cancer Biomarker Development Laboratory," National Institutes of Health Grant No. CA152751 (Funding Start Date: Sep. 24, 2010).
Spira et al. Abstract "The Boston University-UCLA Lung Cancer Biomarker Development Lab," National Institutes of Health Grant No. CA214182 (Funding Start Date: Sep. 20, 2016).

\* cited by examiner

DIAGNOSTIC AND PROGNOSTIC METHODS FOR LUNG DISORDERS USING GENE EXPRESSION PROFILES FROM NOSE EPITHELIAL CELLS

CROSS-REFERENCE TO RELATED APPLICATIONS

This application is a continuation of U.S. application Ser. No. 14/690,182, filed on Apr. 17, 2015, which is a continuation of U.S. application Ser. No. 13/323,655, filed on Dec. 12, 2011, which is a continuation of U.S. application Ser. No. 12/940,840, filed on Nov. 5, 2010, which is a continuation of U.S. application Ser. No. 12/282,320, filed on Sep. 9, 2008, which is a national stage filing under 35 U.S.C. 371 of International Application PCT/US2007/006006, filed Mar. 8, 2007, which claims the benefit under 35 U.S.C. 119(e) from U.S. provisional application Ser. No. 60/780,552, filed on Mar. 9, 2006, the content of which is herein incorporated by reference in their entirety. International Application PCT/US2007/006006 was published under PCT Article 21(2) in English.

GOVERNMENT SUPPORT

The present invention was made, in part, by support from the National Institutes of Health grant No. HL077498. The United States Government has certain rights to the Invention.

BACKGROUND OF THE INVENTION

Field of the Invention

The present invention is directed to method; for diagnosing lung diseases from nasal epithelial cells using gene expression analysis. More specifically, the invention is directed to diagnostic and prognostic methods for detecting from nasal epithelial cell samples lung diseases, particularly lung cancer in subjects, preferably humans. The invention also provides genes the expression of which can be used to analyze lung diseases from the nasal epithelial cell samples.

Background

Lung disorders represent a serious health problem in the modern society. For example, lung cancer claims more than 150,000 lives every year in the United States, exceeding the combined mortality from breast, prostate and colorectal cancers. Cigarette smoking is the most predominant cause of lung cancer. Presently, 25% of the U.S. population smokes, but only 10% to 15% of heavy smokers develop lung cancer. There are also other disorders associated with smoking such as emphysema. There are also health questions arising from people exposed to smokers, for example, second hand smoke. Former smokers remain at risk for developing such disorders including cancer and now constitute a large reservoir of new lung cancer cases. In addition to cigarette smoke, exposure to other air pollutants such as asbestos, and smog, pose a serious lung disease risk to individuals who have been exposed to such pollutants.

Approximately 85% of all subjects with lung cancer die within three years of diagnosis. Unfortunately survival rates have not changed substantially over the past several decodes. This in largely because there are no affective methods for identifying smokers who are at highest risk for developing lung cancer no effective tools for early diagnosis.

The methods that are currently employed to diagnose lung cancer include chest X-ray analysis, bronchoscopy or sputum cytological analysis, computer tomographic analysis of the chest, and positron electron tomographic (PET) analysis. However, none of these methods provide a combination of both sensitivity and specificity needed for an optimal diagnostic test.

We have previously found that a gene group expression pattern analysis from biological samples taken from bronchial epithelial cells permits accurate method for diagnosis and prognosis for development of lung diseases, such as lung cancer (PCT/US2006/014132).

However, the method of sampling epithelial cells from bronchial tissue while less invasive than many other methods has some drawbacks. For example, the patient may not eat or drink for about 6-12 hours prior to the test. Also, if the procedure is performed using a rigid bronchoscope the patient needs general anesthesia involving related risks to the patient. When the method is performed using a flexible bronchoscope, the procedure is performed using local anesthesia. However, several patients experience uncomfortable sensations, such as a sensation of suffocating during such a procedure and thus are relatively resistant for going through the procedure more than once. Also, after the bronchoscopy procedure, the throat may feel uncomfortably scratchy for several days.

While it has been previously described, that RNA can be isolated from mouth epithelial cells for gene expression analysis (U.S. Ser. No. 10/579,376), it has not been clear if such samples routinely reflect the same gene expression changes as bronchial samples that can be used in accurate diagnostic and prognostic methods.

Thus, there is significant interest and need in developing simple non-invasive screening methods for assessing an individual's lung disease, such as lung cancer or risk for developing lung cancer, including primary lung malignancies. It would be preferable if such a method would be more accurate than the traditional chest x-ray or PET analysis or cytological analysis, for example by identifying marker genes which have their expression altered at various states of disease progression.

Therefore, the development of non-invasive tests would be very helpful.

SUMMARY OF THE INVENTION

The present invention provides a much less invasive method for diagnosing lung diseases, such as lung cancer based on analysis of gene expression in nose epithelial cells.

We have found surprisingly that the gene expression changes in nose epithelial cells closely mirrors the gene expression changes in the lung epithelial cells. Accordingly, the invention provides methods for diagnosis, prognosis and follow up of progression or success of treatment for lung diseases using gene expression analysis from nose epithelial cells.

We have also found that the gene expression pattern in the bronchial epithelial cells and nasal epithelial cells very closely correlated. This is in contrast with epithelial cell expression pattern in any other tissue we have studies thus far. The genes the expression of which is particularly closely correlated between the lung and the nose are listed in tables 8, 9 and 10.

The method provides an optimal means for screening for changes indicating malignancies in individuals who, for example are at risk of developing lung diseases, particularly lung cancers because they have been exposed to pollutants, such as cigarette or cigar smoke or asbestos or any other known pollutant. The method allows screening at a routine annual medical examination because it does not need to be performed by an expert trained in bronchoscopy and it does not require sophisticated equipment needed for bronchoscopy.

We discovered that there is a significant correlation between the epithelial cell gene expression in the bronchial tissue and in the nasal passages. We discovered this by analyzing samples from individuals with cancer as well as by analyzing samples from smokers compared to non-smokers.

We discovered a strong correlation between the gene expression profile in the bronchial and nasal epithelial cell samples when we analyzed genes that distinguish individuals with known sarcoidosis from individuals who do not have sarcoidosis.

We also discovered that the same is true, when one compares the changes in the gene expression pattern between smokers and individuals who have never smoked.

Accordingly, we have found a much less invasive method of sampling for prognostic, diagnostic and follow-up purposes by taking epithelial samples from the nasal passages as opposed to bronchial tissue, and that the same genes that have proven effective predictors for lung diseases, such as lung cancer, in smokers and non-smokers, can be used in analysis of epithelial cells from the nasal passages.

The gene expression analysis can be performed using genes and/or groups of genes as described in tables 8, 9 and 10 and, for example, in PCT/US2006/014132. Naturally, other diagnostic genes may also be used, as they are identified.

Accordingly, the invention provides a substantially less invasive method for diagnosis, prognosis and follow-up of lung diseases using samples from nasal epithelial cells. To provide an improved analysis, one preferably uses gene expression analysis.

One can use analysis of gene transcripts individually and in groups or subsets for enhanced diagnosis for lung diseases, such as lung cancer.

Similarly, as the art continues to identify the gene expression changes associated with other lung diseases wherein the disease causes a field effect, namely, wherein the disease-causing agent, i.e. a pollutant, or a microbe or other airway irritant, the analysis and discoveries presented herein allow us to conclude that those gene expression changes can also be analyzed from nasal epithelial cells thus providing a much less invasive and more accurate method for diagnosing lung diseases in general. For example, using the methods as described, one can diagnose any lung disease that results in detectable gene expression changes, including, but not limited to acute pulmonary eosinophilia (Loeffler's syndrome), CMV pneumonia, chronic pulmonary coccidioidomycosis, cryptococcosis, disseminated tuberculosis (infectious), chronic pulmonary histoplasmosis, pulmonary actinomycosis, pulmonary aspergilloma (mycetoma), pulmonary aspergillosis (invasive type), pulmonary histiocytosis X (eosinophilic granuloma), pulmonary nocardiosis, pulmonary tuberculosis, and sarcoidosis. In fact, one of the examples shows a group of genes the expression of which changes when the individual is affected with sarcoidosis.

One example of the gene transcript groups useful in the diagnostic/prognostic tests of the invention using nasal epithelial cells are set forth in Table 6. We have found that taking groups of at least 20 of the Table 6 genes provides a much greater diagnostic capability than chance alone.

Preferably one would use more than 20 of these gene transcript, for example about 20-100 and any combination between, for example, 21, 22, 23, 24, 25, 26, 27, 28, 29, 30, and so on. Our preferred groups are the groups of 361 (Table 8), 107 (Table 9), 70 (Table 10), 96 (Table 1), 84 (Table 2), 50 (Table 3), 36 (Table 4), 80 (Table 5), 535 (Table 6) and 20 (Table 7).

In some instances, we have found that one can enhance the accuracy of the diagnosis by adding certain additional genes to any of these specific groups. When one uses these groups, the genes in the group are compared to a control or a control group. The control groups can be individuals who have not been exposed to a particular airway irritant, such as non-smokers, smokers, or former smokers, or individuals not exposed to viruses or other substance that can cause a "filed effect" in the airways thus resulting in potential for lung disease. Typically, when one wishes to diagnose a disease, the control sample should be from an individual who does not have the diseases and alternatively include one or more samples with individuals who have similar or different lung diseases. Thus, one can match the sample one wishes to diagnose with a control wherein the expression pattern most closely resembles the expression pattern in the sample. Preferably, one compares the gene transcripts or their expression product in the biological sample of an individual against a similar group, except that the members of the control groups do not have the lung disorder, such as emphysema or lung cancer. For example, comparing can be performed in the biological sample from a smoker against a control group of smokers who do not have lung cancer. When one compares the transcripts or expression products against the control for increased expression or decreased expression, which depends upon the particular gene and is set forth in the tables—not all the genes surveyed will show an increase or decrease. However, at least 50% of the genes surveyed must provide the described pattern. Greater reliability is obtained as the percent approaches 100%. Thus, in one embodiment, one wants at least 55%, 60%, 65%, 70%, 75%, 80%, 85%, 90%, 95%, 98%, or 99% of the genes surveyed to show the altered pattern indicative of lung disease, such as lung cancer, as set forth in the tables, infra.

In one embodiment, the nasal epithelial cell sample is analyzed for a group of genes the expression of which is altered in individuals who are at risk of developing lung diseases, such as lung cancer, because of the exposure to air pollutants or other airway irritant such as microbes that occur in the air and are inhaled. This is because we have discovered that air pollutant The method can also be used for analysis of groups of genes the expression of which is consistently altered as a group in individuals who are at risk of developing lung diseases because of the exposure to such air pollutants including microbes and viruses present in the air.

One can analyze the nasal epithelial cells according to the methods of the present invention using gene groups the expression pattern or profile of which can be used to diagnose lung diseases, such as lung cancer and even the type of lung cancer, in more than 60%, preferably more than 65%, still more preferably at least about 70%, still more preferably about 75%, or still more preferably about 80%-95% accuracy from a sample taken from airways of an individual screened fora lung disease, such as lung cancer.

In one embodiment, the invention provides a method of diagnosing a lung disease such as lung cancer using a combination of nasal epithelial cells and the analysis of gene expression pattern of the gene groups as described in the present invention.

Accordingly, the invention provides methods for analyzing gene groups from nasal epithelial cells, wherein the gene expression pattern that can be directly used in diagnosis and prognosis of lung diseases. Particularly, the invention provides analysis from nasal epithelial cells groups of genes the expression profile of which provides a diagnostic and or prognostic test to determine lung disease in an individual exposed to air pollutants. For example, the invention provides analysis from nasal epithelial cells, groups of genes the expression profile of which can distinguish individuals with lung cancer from individuals without lung cancer.

In one embodiment, the invention provides an early asymptomatic screening system for lung cancer by using the analysis of nasal epithelial cells for the disclosed gene expression profiles. Such screening can be performed, for example, in similar age groups as colonoscopy for screening colon cancer. Because early detection in lung cancer is crucial for efficient treatment, the gene expression analysis system of the present invention provides an improved method to detect tumor cells. Thus, the analysis can be made at various time intervals, such as once a year, once every other year for screening purposes. Alternatively, one can use a more frequent sampling if one wishes to monitor disease progression or regression in response to a therapeutic intervention. For example, one can take samples from the same patient once a week, once or two times a month, every 3, 4, 5, or 6 months.

The probes that can be used to measure expression of the gene groups of the invention can be nucleic acid probes capable of hybridizing to the individual gene/transcript sequences identified in the present invention, or antibodies targeting the proteins encoded by the individual gene group gene products of the invention. The probes are preferably immobilized on a surface, such as a gene or protein chip so as to allow diagnosis and prognosis of lung diseases in an individual.

In one preferred embodiment, the invention provides a group of genes that can be used in diagnosis of lung diseases from the nasal epithelial cells. These genes were identified using In one embodiment, the invention provides a group of genes that can be used as individual predictors of lung disease. These genes were identified using probabilities with a t-test analysis and show differential expression in smokers as opposed to non-smokers. The group of genes comprise ranging from 1 to 96, and all combinations in between, for example 5, 10, 15, 20, 25, 30, for example at least 36, at least about, 40, 45, 50, 60, 70, 80, 90, or 96 gene transcripts, selected from the group consisting of genes identified by the following GenBank sequence identification numbers (the identification numbers for each gene are separated by ";" while the alternative GenBank ID numbers are separated by "///"): NM_003335; NM_000918; NM_006430.1; NM_001416.1; NM_004090; NM_006406.1; NM_003001.2; NM_001319; NM_006545.1; NM_021145.1; NM_002437.1; NM_006286; NM_001003698///NM_001003699///NM_002955; NM_001123///NM_006721; NM_024824; NM_004935.1; NM_002853.1; NM_019067.1; NM_024917.1; NM_020979.1; NM_005597.1; NM_007031.1; NM_009590.1; NM_020217.1; NM_025026.1; NM_014709.1; NM_014896.1; AF010144; NM_005374.1; NM_001696; NM_005494///NM_058246; NM_006534/// NM_181659; NM_006368; NM_002268///NM_032771; NM_014033; NM_016138; NM_007048///NM_194441; NM_006694; NM_000051///NM_138292///NM_138293; NM_000410///NM_139002///NM_139003///NM_39004/// NM_139005///NM_139006///NM_139007///NM_139008/// NM_139009///NM_139010///NM_139011; NM_004691; NM_012070///NM_139321///NM_139322; NM_006095; AI632181; AW024467; NM_021814; NM_005547.1; NM_203458; NM_015547///NM_147161; AB007958.1; NM_207488; NM_005809///NM_181737///NM_181738; NM_016248///NM_144490; AK022213.1; NM_005708; NM_207102; AK023895; NM_144606///NM_144997; NM_018530; AK021474; U43604.1; AU147017; AF222691.1; NM_015116; NM_001005375/// NM_001005785///NM_001005786///NM_004081/// NM_020363///NM_020364///NM_020420; AC004692; NM_001014; NM_000585///NM_172174///NM_172175; NM_054020///NM_172095///NM_172096///NM_172097; BE466926; NM_018011; NM_024077; NM_012394; NM_019011///NM_207111///NM_207116; NM_017646; NM_021800; NM_016049; NM_014395; NM_014336; NM_018097; NM_019014; NM_024804; NM_018260; NM_018118; NM_014128; NM_024084; NM_005294; AF077053; NM_138387; NM_024531; NM_000693; NM_018509; NM_033128; NM_020706; AI523613; and NM_014884, the expression profile of which can be used to diagnose lung disease, for example lung cancer, in lung cell sample from a smoker, when the expression pattern is compared to the expression pattern of the same group of genes in a smoker who does not have or is not at risk of developing lung cancer.

In another embodiment, the gene/transcript analysis comprises a group of about 10-20, 20-30, 30-40, 40-50, 50-60, 60-70, 70-80, 80, 80-90, 90-100, 100-120, 120-140, 140-150, 150-160, 160-170, 170-180, 180-190, 190-200, 200-210, 210-220, 220-230, 230-240.240-250, 250-260, 260-270, 270-280, 280-290, 290-300, 300-310, 310-320, 320-330, 330-340, 340-350, 350-360, 360-370, 370-380, 380-390, 390-400, 400-410, 410-420, 420-430, 430-440, 440-450, 450-460, 460-470, 470-480, 480490, 490.500, 500-510, 510-520, 520-530, and up to about 535 genes selected from the group consisting of genes or transcripts as shown in the Table 6.

In one embodiment, the genes are selected from the group consisting of genes or transcripts as shown in Table 5.

In another embodiment, the genes are selected from the genes or transcripts as shown in Table 7.

In one embodiment, the transcript analysis gene group comprises a group of individual genes the change of expression of which is predictive of a lung disease either alone or as a group, the gene transcripts selected from the group consisting of NM_007062.1; NM_001281.1; BC002642.1; NM_000346.1; NM_006545.1; BG034328; NM_019067.1; NM_017925.1; NM_017932.1; NM_030757.1; NM_030972.1; NM_002268 NM_032771; NM_007048/// NM_194441; NM_006694; U85430.1; NM_004691; AB014576.1; BF218804; BE467941; R83000; AL161952.1; AK023843.1; AK021571.1; AK023783.1; AL080112.1; AW971983; AI683552; NM_024006.1; AK026565.1; NM_014182.1; NM_021800.1; NM_016049.1; NM_021971.1; NM_014128.1; AA133341; AF198444.1.

In one embodiment, the gene group comprises a probe set capable of specifically hybridizing to at least all of the 36 gene products. Gene product can be mRNA which can be recognized by an oligonucleotide or modified oligonucleotide probe, or protein, in which case the probe can be, for example an antibody specific to that protein or an antigenic epitope of the protein.

In yet another embodiment, the invention provides a gene group, wherein the expression pattern of the group of genes provides diagnostic for a lung disease. The gene group comprises gene transcripts encoded by a gene group consisting of at least for example 5, 10, 15, 20, 25, 30, preferably at least 36, still more preferably 40, still more preferably 45, and still more preferably 46, 47, 48, 49, or all 50 of the genes selected from the group consisting of and identified by their GenBank identification numbers: NM_007062.1; NM_001281.1; BC000120.1; NM_014255.1; BC002642.1; NM_000346.1; NM_006545.1; BG034328; NM_021822.1; NM_021069.1; NM_019067.1; NM_017925.1; NM_017932.1; NM_030757.1; NM_030972.1; AF126181.1; U 93240.1; U90552.1; AF151056.1; U85430.1; U51007.1; BC005969.1; NM_002271.1; AL566172; AB014576.1; BF218804; AK022494.1; AA114843; BE467941; NM_003541.1; R83000; AL161952.1; AK023843.1; AK021571.1; AK023783.1; AU147182; AL080112.1; AW971983; AI683552; NM_024006.1; AK026565.1; NM_014182.1; NM_021800.1; NM_016049.1; NM_019023.1; NM_021971.1; NM_014128.1; AK025651.1; AA133341; and AF198444.1. In one preferred embodiment, one can use at least 20 of the 36 genes that overlap with the individual predictors and, for example, 5-9 of the non-overlapping genes and combinations thereof.

In another embodiment, the invention provides a group of about 30-180, preferably, a group of about 36-150 genes, still more preferably a group of about 36-100, and still more preferably a group of about 36-50 genes, the expression profile of which is diagnostic of lung cancer in individuals who smoke.

In one embodiment, the invention provides a group of genes the expression of which is decreased in an individual having lung cancer. In one embodiment, the group of genes comprises at least 5-10, 10-15, 15-20, 20-25 genes selected from the group consisting of NM_000918; NM_006430.1; NM_001416.1; NM_004090; NM_006406.1; NM_003001.2; NM_006545.1; NM_002437.1; NM_006286; NM_001123///NM_006721; NM_024824; NM_004935.1; NM_001696; NM_005494///NM_058246; NM_006368; NM_002268///NM_032771; NM_006694; NM_004691; NM_012394; NM_021800; NM_016049; NM_138387; NM. 024531; and NM_018509. One or more other genes can be added to the analysis mixtures in addition to these genes.

In another embodiment, the group of genes comprises genes selected from the group consisting of NM_014182.1; NM_001281.1; NM_024006.1; AF135421.1; L76200.1; NM_000346.1; BC008710.1; BC000423.2; BC008710.1; NM_007062; BC075839.1///BC073760.1; BC072436.1/// BC004560.2; BC001016.2; BC005023.1; BC000360.2; BC007455.2; BC023528.2///BC047680.1; BC064957.1; BC008710.1; BC066329.1; BC023976.2; BC008591.2/// BC050440.1///BC048096.1; and BC028912.1.

In yet another embodiment, the group of genes comprises genes selected from the group consisting of NM_007062.1; NM_001281.1; BC000120.1; NM_014255.1; BC002642.1; NM_000346.1; NM_006545.1; BG034328; NM_021822.1; NM_021069.1; NM_019067.1; NM_017925.1; NM_017932.1; NM_030757.1; NM_030972.1; AF126181.1; U93240.1; U90552.1; AF151056.1; U85430.1; U51007.1; BC005969.1; NM_002271.1; AL566172; and AB014576.1.

In one embodiment, the invention provides a group of genes the expression of which is increased in an individual having lung cancer. In one embodiment, the group of genes comprises genes selected from the group consisting of NM_003335; NM_001319; NM_021145.1; NM_001003698///NM_001003699///; NM_002955; NM_002853.1; NM_019067.1; NM_024917.1; NM_020979.1; NM_005597.1; NM_007031.1; NM_009590.1; NM_020217.1; NM_025026.1; NM_014709.1; NM_014896.1; AF010144; NM_005374.1; NM_006534///NM_181659; NM_014033; NM_016138; NM_007048///NM_194441; NM_000051///NM_138292/// NM_138293; NM_000410///NM_139002///NM_139003/// NM_139004///NM_139005///NM_139006///NM_139007/// NM_139008///NM_139009///NM_139010///NM_139011; NM_012070///NM_139321///NM_139322; NM_006095; AI632181; AW024467; NM_021814; NM_005547.1; NM_203458; NM_015547///NM_147161; AB007958.1; NM_207488; NM_005809///NM_181737///NM_181738; NM_016248///NM_144490; AK022213.1; NM_005708; NM_207102; AK023895; NM_144606///NM_144997; NM_018530; AK021474; U43604.1; AU147017; AF222691.1; NM_015116; NM_001005375/// NM_001005785///NM_001005786///NM_004081/// NM_020363///NM_020364///NM_020420; AC004692; NM_001014; NM_000585///NM_172174///NM_172175; NM_054020///NM_172095///NM_172096///NM_172097; BE466926; NM_018011; NM_024077; NM_019011/// NM_207111///NM_207116; NM_017646; NM_014395; NM_014336; NM_018097; NM_019014; NM_024804; NM_018260; NM_018118; NM_014128; NM_024084; NM_005294; AF077053; NM_000693; NM_033128; NM_020706; AI523613; and NM_014884.

In one embodiment, the group of genes comprises genes selected from the group consisting of NM_030757.1; R83000; AK021571.1; NM_17932.1; U85430.1; AI683552; BC002642.1; AW024467; NM_030972.1; BC021135.1; AL161952.1; AK026565.1; AK023783.1; BF218804; AK023843.1; BC001602.1; BC034707.1; BC064619.1; AY280502.1; BC059387.1; BC061522.1; U50532.1; BC006547.2; BC008797.2; BC000807.1; AL080112.1; BC033718.1///BC046176.1///; BC038443.1; Hs.288575 (UNIGENE ID); AF020591.1; BC002503.2; BC009185.2; Hs.528304 (UNIGENE ID); U50532.1; BC013923.2; BC031091; Hs.249591 (Unigene ID); Hs.286261 (Unigene ID); AF348514.1; BC066337.1///BC058736.1/// BC050555.1; Hs.216623 (Unigene ID); BC072400.1; BC041073.1; U43965.1; BC021258.2; BC016057.1; BC016713.1///BC014535.1///AF237771.1; BC000701.2; BC010067.2; Hs.156701 (Unigene ID); BC030619.2; U43965.1; Hs.438867 (Unigene ID); BC035025.2/// BC050330.1; BC074852.2///BC074851.2; Hs.445885 (Unigene ID); AF365931.1; and AF257099.1.

In one embodiment, the group of genes comprises genes selected from the group consisting of BF218804; AK022494.1; AA114843; BE467941; NM_003541.1; R83000; AL161952.1; AK023843.1; AK021571.1; AK023783.1; AU147182; AL080112.1; AW971983; A1683552; NM_024006.1; AK026565.1; NM_014182.1; NM_021800.1; NM_016049.1; NM_019023.1; NM_021971.1; NM_014128.1; AK025651.1; AA133341; and AF198444.1.

In another embodiment, the invention provides a method for diagnosing a lung disease comprising obtaining a nucleic acid sample from lung, airways or mouth of an individual exposed to an air pollutant, analyzing the gene transcript levels of one or more gene groups provided by the present invention in the sample, and comparing the expression pattern of the gene group in the sample to an expression pattern of the same gene group in an individual, who is exposed to similar air pollutant but not having lung disease, such as lung cancer or emphysema, wherein the difference in the expression pattern is indicative of the test individual having or being at high risk of developing a lung disease. The decreased expression of one or more of the genes, preferably all of the genes including the genes listed on Tables 1-4 as "down" when compared to a control, and/or increased expression of one or more genes, preferably all of the genes listed on Tables 1-4 as "up" when compared to an individual exposed to similar air pollutants who does not have a lung disease, is indicative of the person having a lung disease or being at high risk of developing a lung disease, preferably, lung cancer, in the near future and needing frequent follow ups to allow early treatment of the disease.

In one preferred embodiment, the lung disease is lung cancer. In one embodiment, the air pollutant is tobacco or tobacco smoke.

Alternatively, the diagnosis can separate the individuals, such as smokers, who are at lesser risk of developing lung diseases, such as lung cancer by analyzing from the nasal epithelial cells the expression pattern of the gene groups of the invention provides a method of excluding individuals from invasive and frequent follow ups.

Accordingly, in one embodiment, the invention provides methods for prognosis, diagnosis and therapy designs for lung diseases comprising obtaining an nasal epithelial cell sample from an individual who smokes and analyzing expression profile of the gene groups of the present invention, wherein an expression pattern of the gene group that deviates from that in a healthy age, race, and gender matched smoker, is indicative of an increased risk of developing a lung disease. Tables 1-4 indicate the expression pattern differences as either being down or up as compared to a control, which is an individual exposed to similar airway pollutant but not affected with a lung disease.

The invention also provides methods for prognosis, diagnosis and therapy designs for lung diseases comprising obtaining an nasal epithelial cell sample from a non-smoker individual and analyzing expression profile of the gene groups of the present invention, wherein an expression pattern of the gene group that deviates from that in a healthy age, race, and gender matched smoker, is indicative of an increased risk of developing a lung disease.

In one embodiment, the analysis is performed using nucleic acids, preferably RNA, in the biological sample.

In one embodiment, the analysis is performed analyzing the amount of proteins encoded by the genes of the gene groups of the invention present in the sample.

In one embodiment the analysis is performed using DNA by analyzing the gene expression regulatory regions of the groups of genes of the present invention using nucleic acid polymorphisms, such as single nucleic acid polymorphisms or SNPs, wherein polymorphisms known to be associated with increased or decreased expression are used to indicate increased or decreased gene expression in the individual. For example, methylation patterns of the regulatory regions of these genes can be analyzed.

In one embodiment, the present invention provides a minimally invasive sample procurement method for obtaining nasal epithelial cell RNA that can be analyzed by expression profiling of the groups of genes, for example, by array-based gene expression profiling. These methods can be used to diagnose individuals who are already affected with a lung disease, such as lung cancer, or who are at high risk of developing lung disease, such as lung cancer, as a consequence of being exposed to air pollutants. These methods can also be used to identify further patterns of gene expression that are diagnostic of lung disorders/diseases, for example, cancer or emphysema, and to identify subjects at risk for developing lung disorders.

The invention further provides a method of analyzing nasal epithelial cells using gene group microarray consisting of one or more of the gene groups provided by the invention, specifically intended for the diagnosis or prediction of lung disorders or determining susceptibility of an individual to lung disorders.

In one embodiment, the invention relates to a method of diagnosing a disease or disorder of the lung comprising obtaining a sample from nasal epithelial cells, wherein the sample is a nucleic acid or protein sample, from an individual to be diagnosed; and determining the expression of group of identified genes in said sample, wherein changed expression of such gene compared to the expression pattern of the same gene in a healthy individual with similar life style and environment is indicative of the individual having a disease of the lung.

In one embodiment, the invention relates to a method of diagnosing a disease or disorder of the lung comprising obtaining at least two nasal epithelial samples, wherein the samples are either nucleic acid or protein samples in at least one, two, 3, 4, 5, 6, 7, 8, 9, or more time intervals from an individual to be diagnosed; and determining the expression of the group of identified genes in said sample, wherein changed expression of at least about for example 5, 10, 15, 20, 25, 30, preferably at least about 36, 40, 50, 60, 70, 80, 90, 100, 110, 120, 130, 140, 150, 160, 170, or 180 of such genes in the sample taken later in time compared to the sample taken earlier in time is diagnostic of a lung disease.

In one embodiment, the disease of the lung is selected from the group consisting of asthma, chronic bronchitis, emphysema, primary pulmonary hypertension, acute respiratory distress syndrome, hypersensitivity pneumonitis, eosinophilic pneumonia, persistent fungal infection, pulmonary fibrosis, systemic sclerosis, idiopathic pulmonary hemosiderosis, pulmonary alveolar proteinosis, and lung cancer, such as adenocarcinoma, squamous cell carcinoma, small cell carcinoma, large cell carcinoma, and benign neoplasm of the lung (e.g., bronchial adenomas and hamartomas).

In a particular embodiment, the nucleic acid sample is RNA.

In one embodiment, individual to be diagnosed is an individual who has been exposed to tobacco smoke, an individual who has smoked, or an individual who currently smokes.

The invention also provides analysis of nasal epithelial cells using an array, for example, a microarray for diagnosis of a disease of the lung having immobilized thereon a plurality of oligonucleotides which hybridize specifically to genes of the gene groups which are differentially expressed in airways exposed to air pollutants, such as cigarette smoke, and have or are at high risk of developing lung disease, as compared to those individuals who are exposed to similar air pollutants and airways which are not exposed to such pollutants. In one embodiment, the oligonucleotides hybridize specifically to one allelic form of one or more genes which are differentially expressed for a disease of the lung. In a particular embodiment, the differentially expressed genes are selected from the group consisting of the genes shown in tables 1-4; preferably the group of genes comprises genes selected from the Table 3. In one preferred embodiment, the group of genes comprises the group of at least 20 genes selected from Table 3 and additional 5-10 genes selected from Tables 1 and 2. In one preferred embodiment, at least about 10 genes are selected from Table 4.

BRIEF DESCRIPTION OF FIGS

FIGS. 1A-1F show, hierarchical clustering of bronchial airway epithelial samples from current (striped box) and never (white box) smokers according to the expression of 60 genes whose expression levels are altered by smoking in the nasal epithelium. Airway samples tend to group with their appropriate class. Dark grey indicates higher level of expression and light grey lower level of expression.

Figure 2:
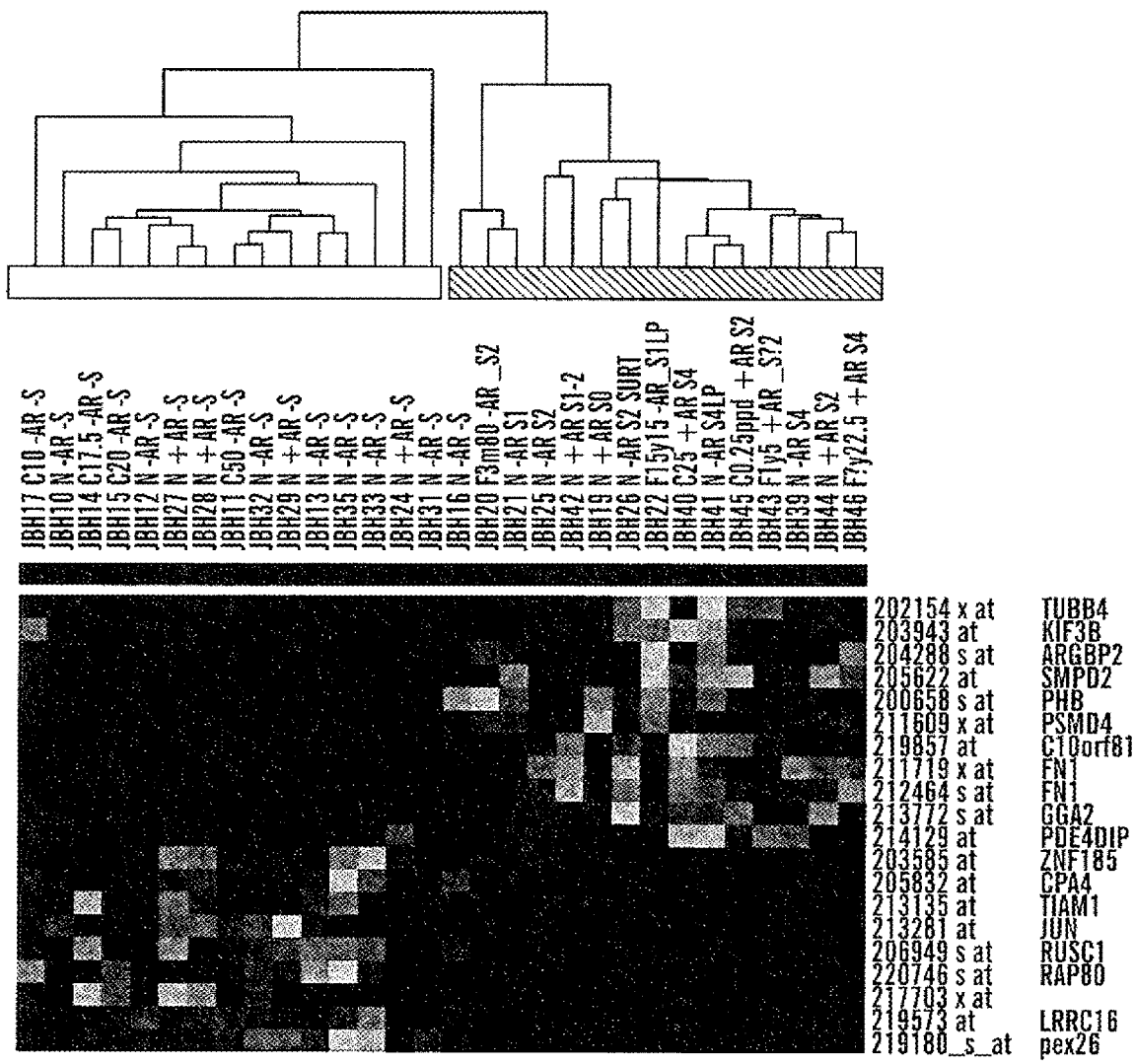

FIG. 2 shows hierarchical clustering of nasal epithelial samples from patients with sarcoid (striped box) and normal healthy volunteers (white box) according to the expression of top 20 t-test genes that differ between the 2 groups (P<0.00005). With few exceptions, samples group into their appropriate classes. Light grey=low level of expression, black=mean level of expression, dark grey=high level of expression.

Figure 3:
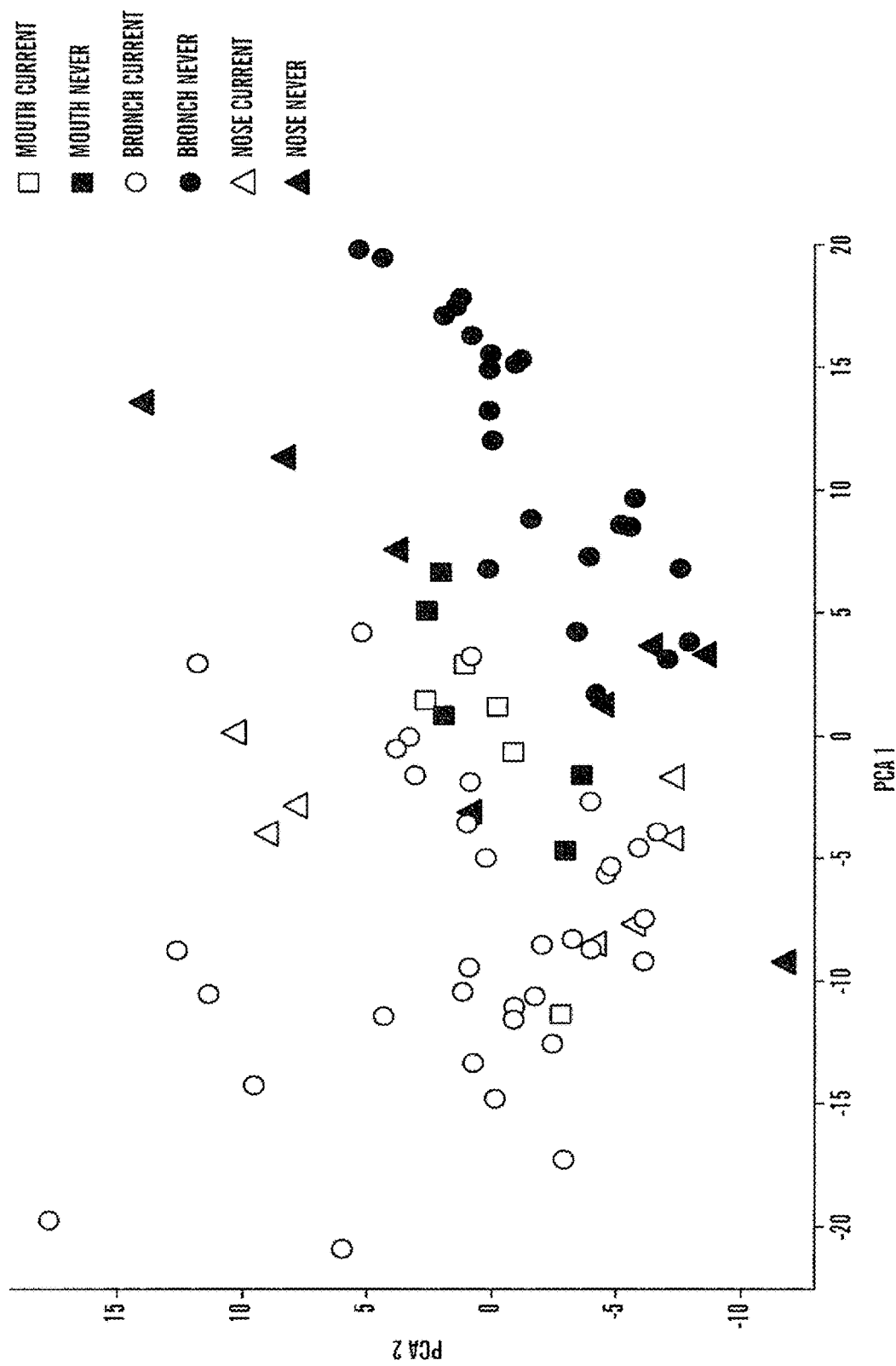

FIG. 3 shows smoking related genes in mouth, nose and bronchus. Principal component analysis (PCA) shows the variation in expression of genes affected by tobacco exposure in current smokers (dark grey) and never smokers (black). Airway epithelium type is indicated by the symbol shape: bronchial (circle), nasal (triangle) and mouth (square). Samples largely separate by smoking status across the first principal component, with the exception of samples from mouth. This indicates a common gene expression host response that can be seen both in the bronchial epithelial tissue and the nasal epithelial tissue.

Figure 4:
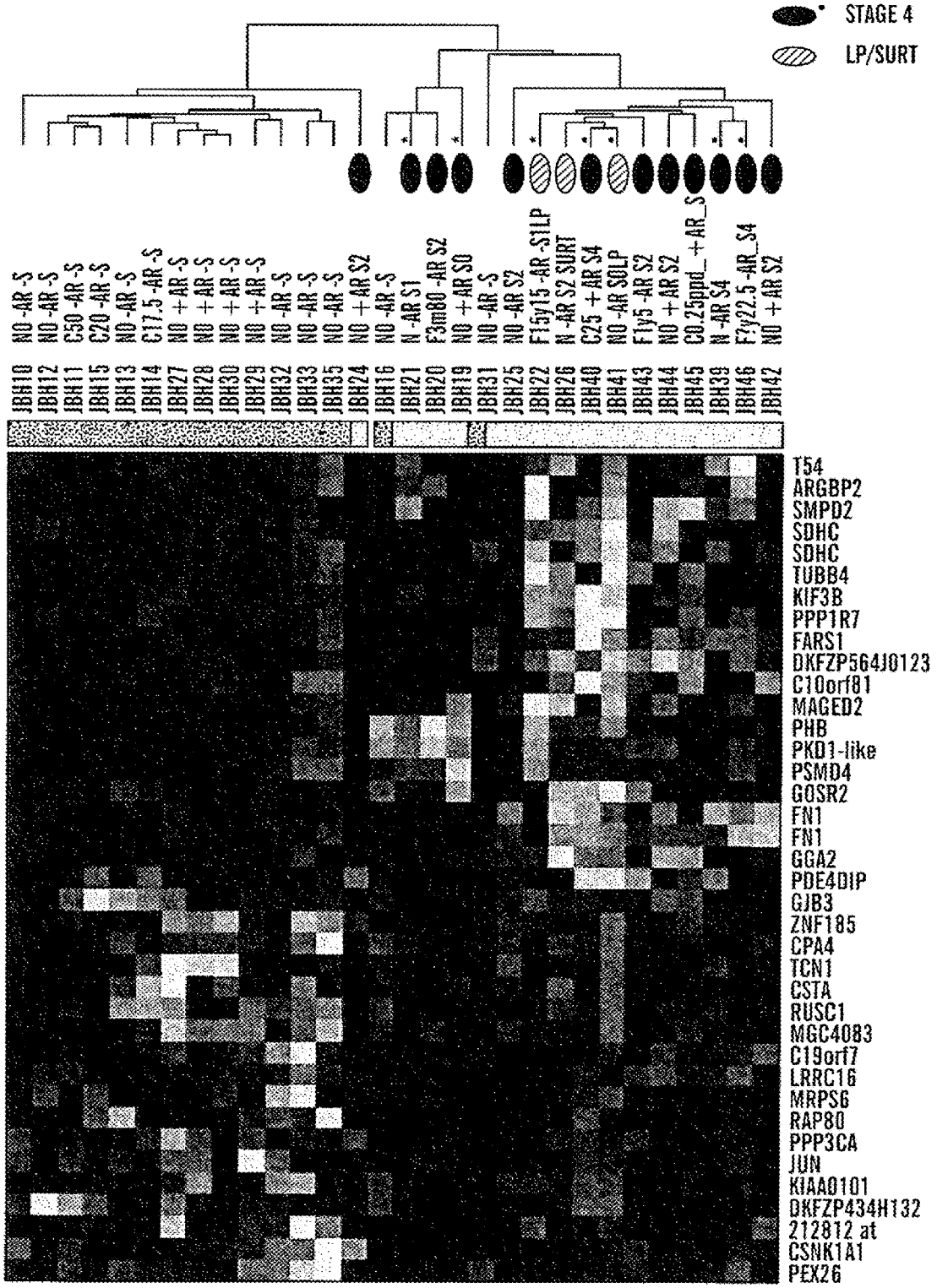

FIG. 4 shows a supervised hierarchical clustering analysis of cancer samples. Individuals with sarcoidosis and individuals with no sarcoids were sampled from both lung tissues and nasal tissues. Gene expression analysis showed that expression of 37 genes can be used to differentiate the cancer samples and non-cancer sampled either from bronchial or nasal epithelial cells. Light grey in the clustering analysis indicates low level of expression and dark grey high level of expression. Asterisk next to the circles indicates that these samples were from an individual with stage 0-1 sarcoidosis. The dot next to the circle indicates that these samples were from an individual with a stage 4 sarcoidosis.

Figure 5:
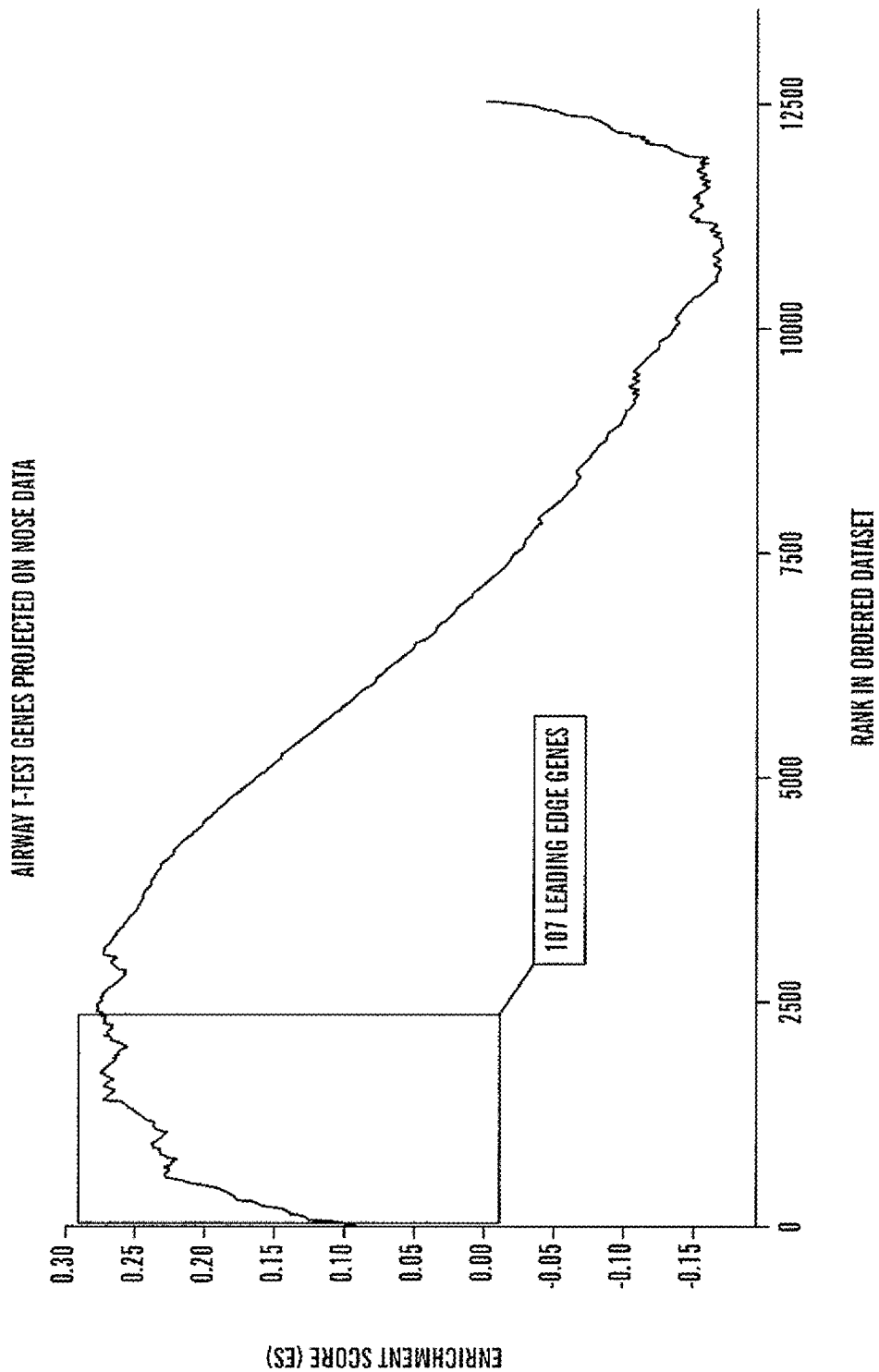

FIG. 5 shows airway t-test genes projected on nose data including the 107 leading edge genes as shown in Table 9. Enrichment of differentially expressed bronchial epithelial genes among genes highly changed in the nasal epithelium in response to smoking. Results from GSEA analysis shows the leading edge of the set of 361 differentially expressed bronchial epithelial genes being overrepresented among the top ranked list of genes differentially expressed in nasal epithelium cells in response to smoking. There are 107 genes that comprise the "leading edge subset" (p<0.001).

Figure 6:
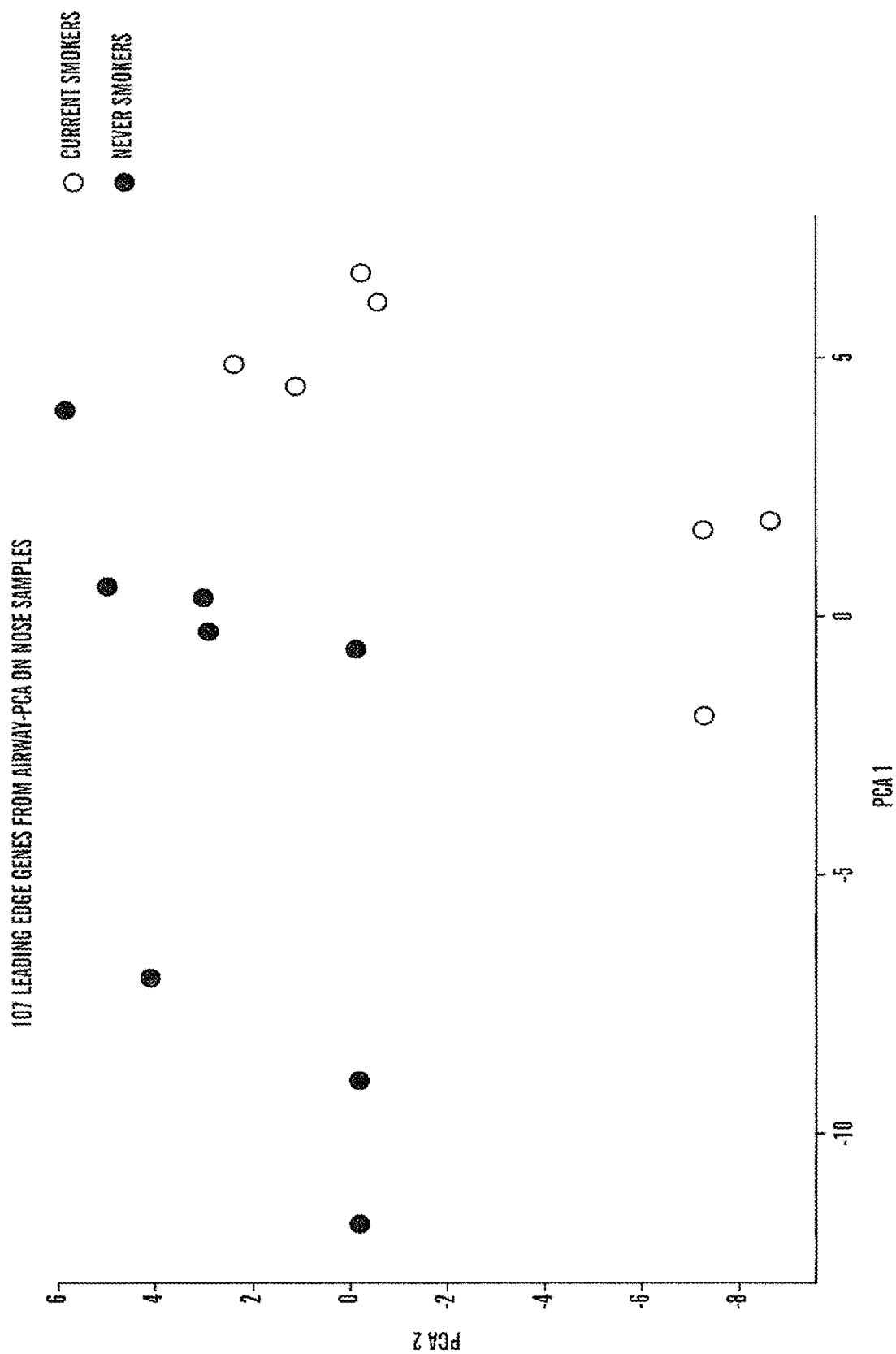

FIG. 6 shows 107 Leading Edge Genes from Airway—PCA on Nose Samples. Asterisk next to the circle indicates current smokers. Dark circles represent samples from never smokers. Principal component analysis of 107 "leading edge" genes from bronchial epithelial cells enriched in the nasal epithelial gene expression profile. Two dimensional PCA of the 107 "leading edge" genes from the bronchial epithelial signature that are enriched in the nasal epithelial cell expression profile.

Figure 7:
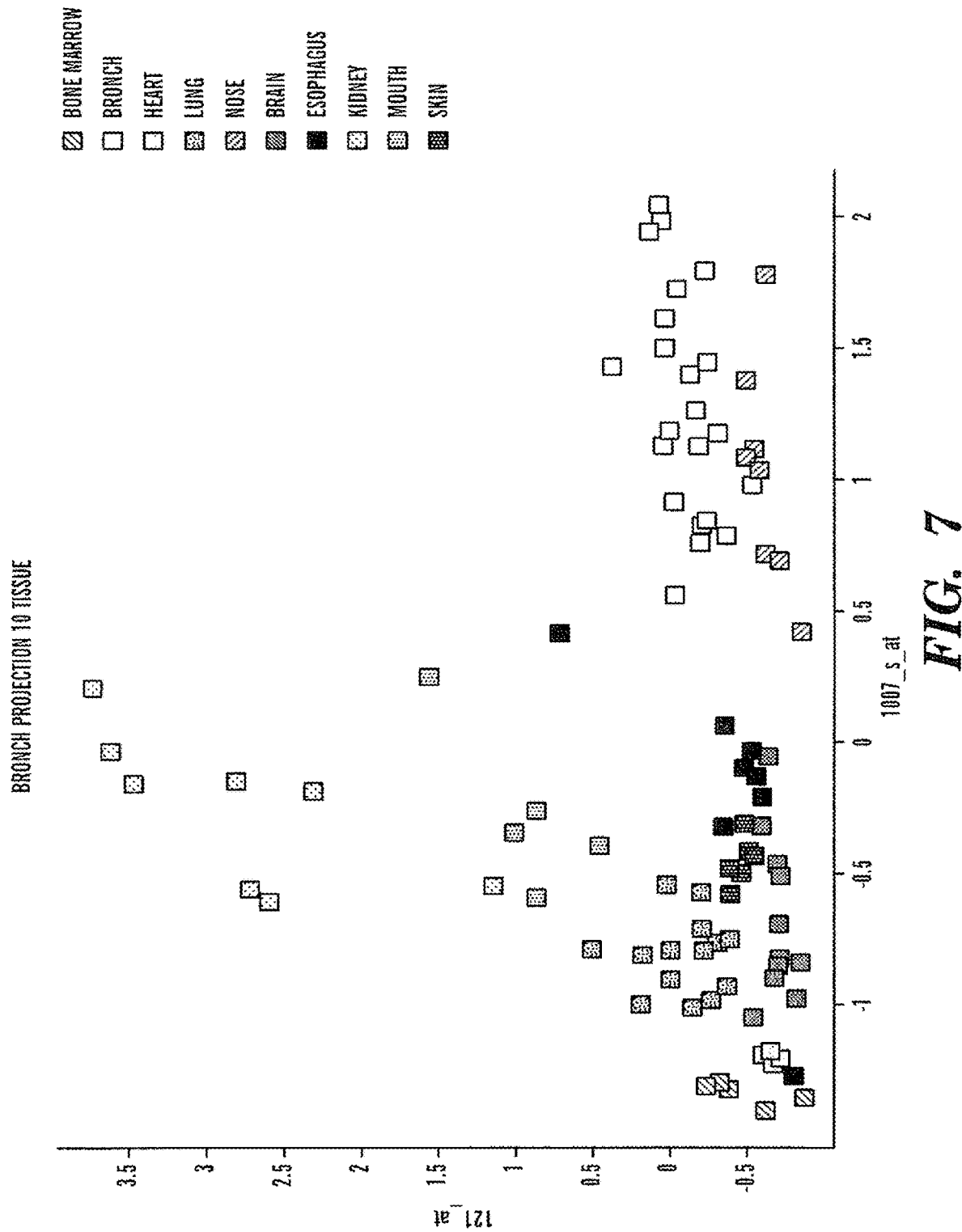

FIG. 7 shows a Bronch projection from 10 tissues. From this figure one can see, that the samples from bronchial epithelial cells (dotted squares) and the samples from nose epithelial cells (crossed squares) overlapped closely and were clearly distinct from samples from other tissues, including mouth. Principal component analysis of 2382 genes from normal airway transcriptome across 10 tissues. Principal component analysis (PCA) of 2382 genes from the normal airway transcriptome across 10 different tissue types. Samples separate based on expression of transcriptome genes.

Figure 8A:
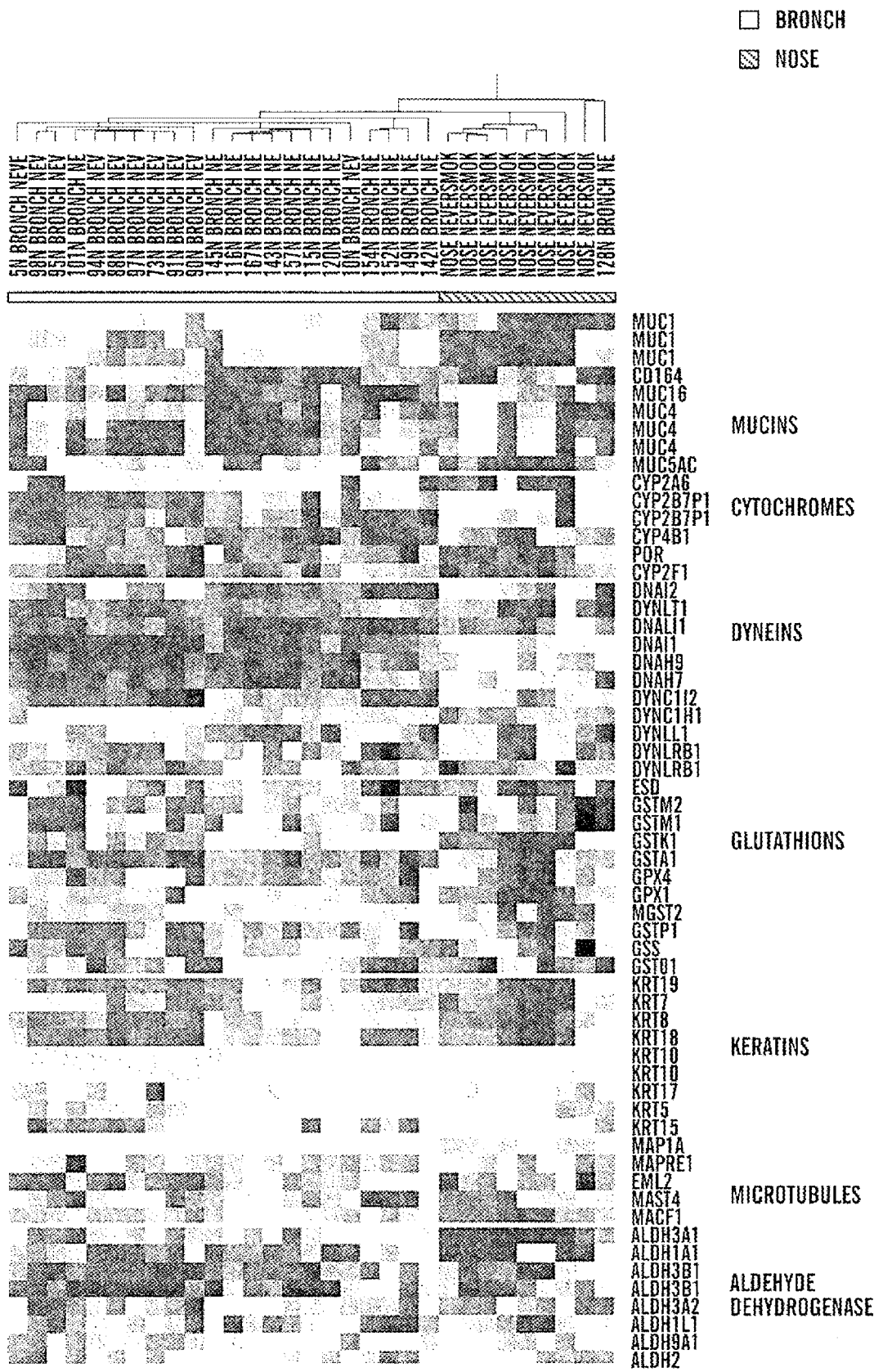
Figure 8B:
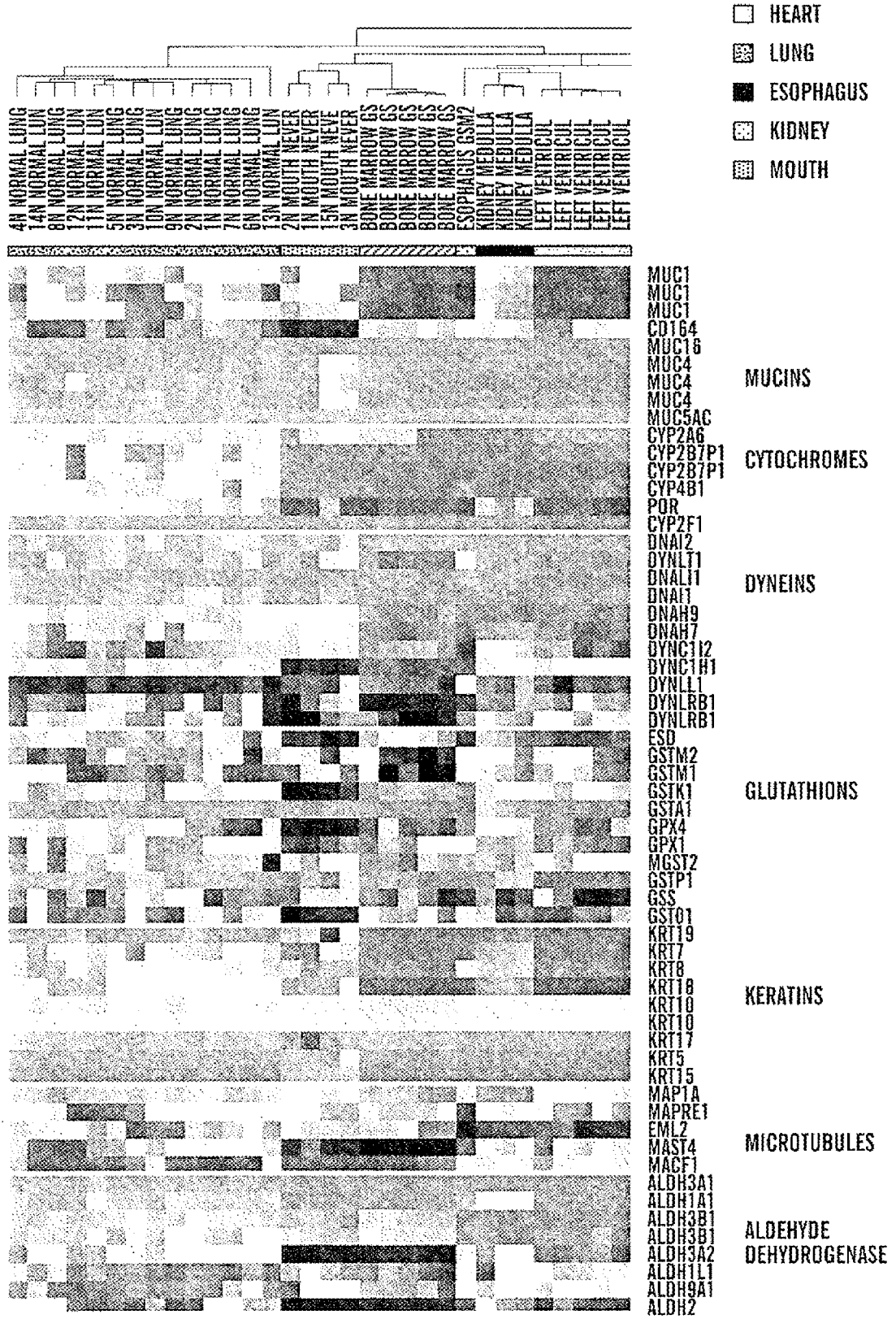
Figure 8C:
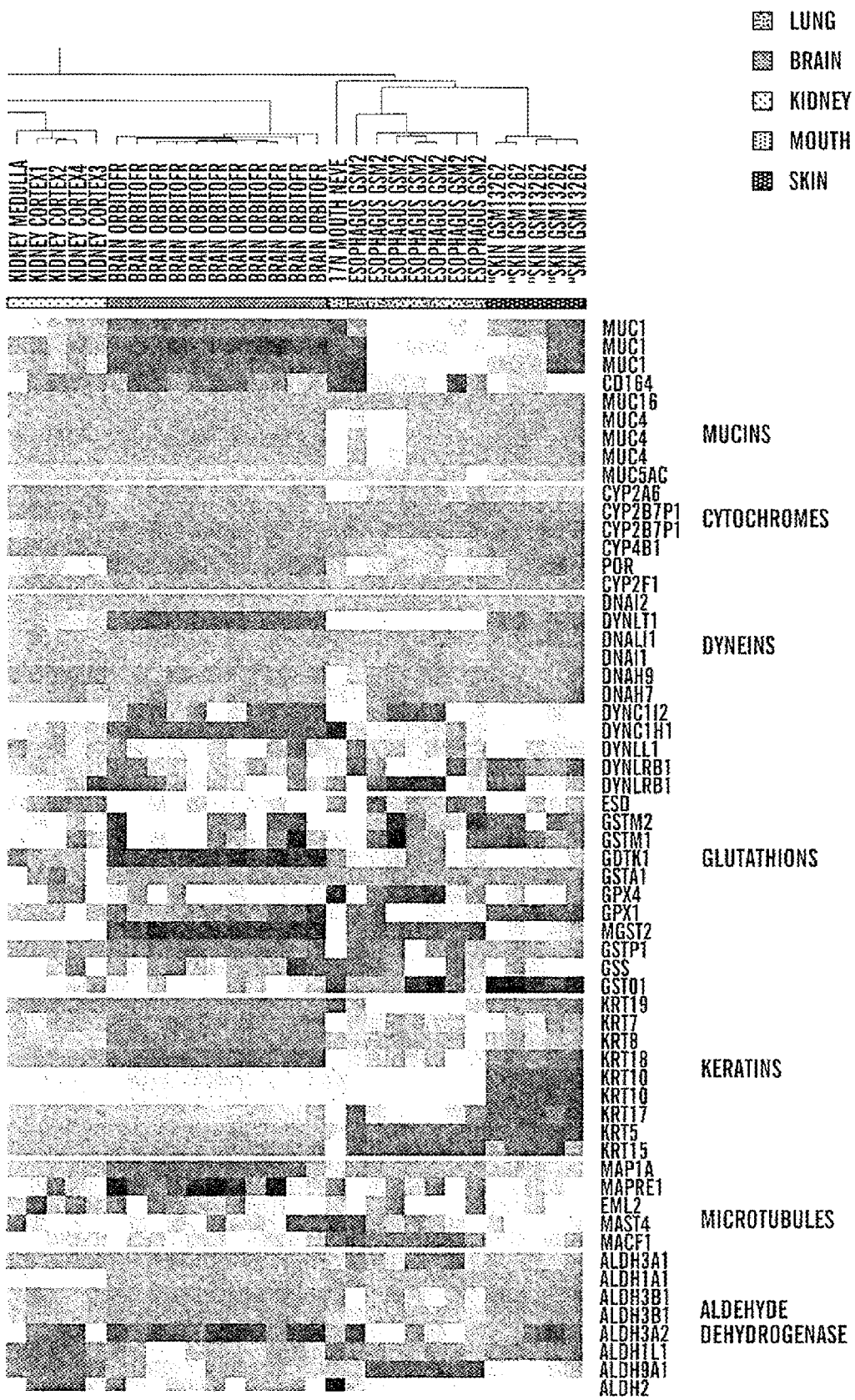

FIGS. 8A-8C show a hierarchical clustering of 51 genes across epithelial cell functional categories. Supervised hierarchical clustering of 51 genes spanning mucin, dynein/microtubule, cytochrome P450, glutathione, and keratin functional gene categories. The 51 genes were clustered across the 10 tissue types separately for each functional group.

DETAILED DESCRIPTION OF THE INVENTION

The present invention describes a novel method for prognosis and diagnosis and follow-up for lung diseases. The method is based on detecting gene expression changes of nose epithelial cells which we have discovered closely mirror the gene expression changes in the lung.

Specifically, we have discovered that similar patterns of gene expression changes can be found in the nose epithelial cells when compared to lung epithelial changes in two model systems. In one experiment, we showed that a host gene expression in response to tobacco smoke is similar whether it is measured from the lung epithelial cells or from the nasal epithelial cells (FIG. 3). Accordingly, we have discovered that we can rely on the results and data obtained with bronchial epithelial cells. This correlation is similar, typically better than 75%, even if it is not identical. Thus, by looking at the same gene groups that are diagnostic and/or prognostic for bronchial epithelial cells those groups are also diagnostic and/or prognostic for nasal epithelial cells. We also showed that gene expression changes distinguishing between individuals affected with a lung diseases, such as sarcoidosis, and from individuals not affected with that diseases.

Accordingly, the invention provides a substantially less invasive method for diagnosis, prognosis and follow-up of lung diseases using gene expression analysis of samples from nasal epithelial cells.

One can take the nose epithelial cell sample from an individual using a brush or a swab. One can collect the nose epithelial cells in any way known to one skilled in the art. For example one can use nasal brushing. For example, one can collect the nasal epithelial cells by brushing the inferior turbinate and/or the adjacent lateral nasal wall. For example, following local anesthesia with 2% lidocaine solution, a CYROBRUSH® (MedScand Medical, Malmö, Sweden) or a similar device, is inserted into the nare, for example the right nare, and under the inferior turbinate using a nasal speculum for visualization. The brush is turned a couple of times, for example 1, 2, 3, 4, 5 times, to collect epithelial cells.

To isolate nucleic acids from the cell sample, the cells can be placed immediately into a solution that prevents nucleic acids from degradation. For example, if the cells are collected using the CYTOBRUSH, and one wishes to isolate RNA, the brush is placed immediately into an RNA stabilizer solution, such as RNALATER®, AMBION®, Inc.

One can also isolate DNA. After brushing, the device can be placed in a buffer, such as phosphate buffered saline (PBS) for DNA isolation.

The nucleic acids are then subjected to gene expression analysis. Preferably, the nucleic acids are isolated and purified. However, if one uses techniques such as microfluidic devises, cells may be placed into such device as whole cells without substantial purification.

In one preferred embodiment, one analyzes gene expression from nasal epithelial cells using gene/transcript groups and methods of using the expression profile of these gene/transcript groups in diagnosis and prognosis of lung diseases.

We provide a method that is much less invasive than analysis of bronchial samples. The method provided herein not only significantly increases the diagnostic accuracy of lung diseases, such as lung cancer, but also make the analysis much less invasive and thus much easier for the patients and doctors to perform. When one combines the gene expression analysis of the present invention with bronchoscopy, the diagnosis of lung cancer is dramatically better by detecting the cancer in an earlier stage than any other available method to date, and by providing far fewer false negatives and/or false positives than any other available method.

In one embodiment, one analyzes the nasal epithelial calls for a group of gene transcripts that one can use individually and in groups or subsets for enhanced diagnosis for lung diseases, such as lung cancer, using gene expression analysis.

On one embodiment, the invention provides a group of genes useful for lung disease diagnosis from a nasal epithelial cell sample as listed in Tables 8, 9, and/or 10.

In one embodiment, one would analyze the nasal epithelial cells using at least one and no more than 361 of the genes listed in Table 8. For example, one can analyze 1, 2, 3, 4, 5, 6, 7, 8, 9, 10, 10-15, 15-20, 20-30, 30-40, 40-50, at least 10, at least 20, at least 30, at least 40 at least 50, at least 60, at least 70, at least 80, at least 90, at least 100, at least 110, at least 120, at least 130, at least 140, at least 150, at least 160, at least or at maximum of 170, at least or at maximum of 180; at least or at maximum of 190, at least or at maximum of 200, 210, 220, 230, 240, 250, 260, 270, 280, 290, 300, 310, 320, 330, 340, 350, 360, or at least 361 or at maximum of the 361 genes of genes as listed on Table 8.

In one embodiment, the invention provides genes

One example of the gene transcript groups useful in the diagnostic/prognostic tests of the invention is set forth in Table 6. We have found that taking any group that has at least 20 of the Table 6 genes provides a much greater diagnostic capability than chance alone and that these changes are substantially the same in the nasal epithelial cells than they are in the bronchial samples as described in PCT/US2006/014132.

Preferably one would analyze the nasal epithelial cells using more than 20 of these gene transcript, for example about 20-100 and any combination between, for example, 21, 22, 23, 24, 25, 26, 27, 28, 29, 30, and so on. Our preferred groups are the groups of 96 (Table 1), 84 (Table 2), 50 (Table 3), 36 (Table 4), 80 (Table 5), 535 (Table 6) and 20 (Table 7). In some instances, we have found that one can enhance the accuracy of the diagnosis by adding additional genes to any of these specific groups.

Naturally, following the teachings of the present invention, one may also include one or more of the genes and/or transcripts presented in Tables 1-7 into a kit or a system for a multicancer screening kit. For example, any one or more genes and or transcripts from Table 7 may be added as a lung cancer marker for a gene expression analysis.

When one uses these groups, the genes in the group are compared to a control or a control group. The control groups can be non-smokers, smokers or former smokers. Preferably, one compares the gene transcripts or their expression product in the nasal epithelial cell sample of an individual against a similar group, except that the members of the control groups do not have the lung disorder, such as emphysema or lung cancer. For example, comparing can be performed in the nasal epithelial cell sample from a smoker against a control group of smokers who do not have lung cancer. When one compares the transcripts or expression products against the control for increased expression or decreased expression, which depends upon the particular gene and is set forth in the tables—not all the genes surveyed will show an increase or decrease. However, at least 50% of the genes surveyed must provide the described pattern. Greater reliability if obtained as the percent approaches 100%. Thus, in one embodiment, one wants at least 55%, 60%, 65%, 70%, 75%, 80%, 85%, 90%, 95%, 98%, 99% of the genes surveyed to show the altered pattern indicative of lung disease, such as lung cancer, as set forth in the tables as shown below.

The presently described gene expression profile can also be used to screen for individuals who are susceptible for lung cancer. For example, a smoker, who is over a certain age, for example over 40 years old, or a smoker who has smoked, for example, a certain number of years, may wish to be screened for lung cancer. The gene expression analysis from nasal epithelial cells as described herein can provide an accurate very early diagnosis for lung cancer. This is particularly useful in diagnosis of lung cancer, because the earlier the cancer is detected, the better the survival rate is.

For example, when we analyzed the gene expression results, we found, that if one applies a less stringent threshold, the group of 80 genes as presented in Table 5 are part of the most frequently chosen genes across 1000 statistical test runs (see Examples below for more details regarding the statistical testing). Using random data, we have shown that no random gene shows up more than 67 times out of 1000. Using such a cutoff, the 535 genes of Table 6 in our data show up more than 67 times out of 1000. All the 80 genes in Table 5 form a subset of the 535 genes. Table 7 shows the top 20 genes which are subset of the 535 list. The direction of change in expression is shown using signal to noise ratio. A negative number in Tables 5, 6, and 7 means that expression of this gene or transcript is up in lung cancer samples. Positive number in Table 5, 6, and 7, indicates that the expression of this gene or transcript is down in lung cancer.

Accordingly, any combination of the genes and/or transcripts of Table 6 can be used. In one embodiment, any combination of at least 5-10, 10-20, 20-30, 30-40, 40-50, 50-60, 60-70, 70-80, 80, 80-90, 90-100, 100-120, 120-140, 140-150, 150-160, 160-170, 170-180, 180-190, 190-200, 200-210, 210-220, 220-230, 230-240, 240-250, 250-260, 260-270, 270-280, 280-290, 290-300, 300-310, 310-320, 320-330, 330-340, 340-350, 350-360, 360-370, 370-380, 380-390, 390-400, 400.410, 410-420, 420-430, 430-440, 440-450, 450-460, 460-470, 470-480, 480-490, 490-500, 500-510, 510-520, 520-530, and up to about 535 genes selected from the group consisting of genes or transcripts as shown in the Table 6.

Table 7 provides 20 of the most frequently variably expressed genes in lung cancer when compared to samples without cancer. Accordingly, in one embodiment, any combination of about 3-5, 5-10, 11, 12, 13, 14, 15, 16, 17, 18, 19, or all 20 genes and/or transcripts of Table 7, or any subcombination thereof are used.

In one embodiment, the invention provides a gene group the expression profile of nasal epithelial cells which is useful in diagnosing lung diseases and which comprises probes that hybridize ranging from 1 to 96 and all combinations in between for example 5, 10, 15, 20, 25, 30, 35, at least about 36, at least to 40, at least to 50, at least to 60, to at least 70, to at least 80, to at least 90, or all of the following 96 gene sequences: NM_003335; NM_000918; NM_006430.1; NM_001416.1; NM_004090; NM_006406.1; NM_003001.2; NM_001319; NM_006545.1; NM_021145.1; NM_002437.1; NM_006286; NM_001003698///NM_001003699///NM_002955; NM_001123///NM_006721; NM_024824; NM_004935.1; NM_002853.1; NM_019067.1; NM_024917.1; NM_020979.1; NM_005597.1; NM_007031.1; NM_009590.1; NM_020217.1; NM_025026.1; NM_014709.1; NM_014896.1; AF010144; NM_005374.1; NM_001696; NM_005494///NM_058246; NM_006534/// NM_181659; NM_006368; NM_002268///NM_032771; NM_014033; NM_016138; NM_007048///NM_194441; NM_006694; NM_000051///NM_138292///NM_138293; NM_000410///NM_139002///NM_139003///NM_139004/// NM_139005///NM_139006///NM_139007///NM_139008/// NM_139009///NM_139010///NM_139011; NM_004691; NM_012070///NM_139321///NM_139322; NM_006095; AI632181; AW024467; NM_021814; NM_005547.1; NM_203458; NM_015547///NM_147161; AB007958.1; NM_207488; NM_005809///NM_181737///NM_181738; NM_016248///NM_144490; AK022213.1; NM_005708; NM_207102; AK023895; NM_144606///NM_144997; NM_018530; AK021474; U43604.1; AI147017; AF222691.1; NM_015116; NM_001005375/// NM_001005785///NM_001005786 NM_004081/// NM_020363///NM_020364///NM_020420; AC004692; NM_001014; NM_000585///NM_172174///NM_172175; NM_054020///NM_172095///NM_172096///NM_172097; BE466926; NM_018011; NM_024077; NM_012394; NM_019011///NM_2071111///NM_207116; NM_017646; NM_021800; NM 016049; NM_014395; NM_014336; NM_018097; NM_019014; NM_024804; NM_018260; NM_018118; NM_014128; NM_024084; NM_005294; AF077053; NM_138387; NM_024531; NM_000693; NM_018509; NM_033128; NM_020706; AI523613; and NM_014884

In one embodiment, the invention provides a gene group the expression profile of nasal epithelial cells of which is useful in diagnosing lung diseases and comprises probes that hybridize to at least, for example, 5, 10, 15, 20, 25, 30, 35, at least about 36, at least to 40, at least to 50, at least to 60, to at least 70, at least 80, to all of the following 84 gene sequences: NM_030757.1; R83000; AK021571.1; NM_014182.1; NM_17932.1; U85430.1; AI683552; BC002642.1; AW024467; NM_030972.1; BC021135.1; AL161952.1; AK026565.1; AK023783.1; BF218804; NM_001281.1; NM_024006.1; AK023843.1; BC001602.1; BC034707.1; BC064619.1; AY280502.1; BC059387.1; AF135421.1; BC061522.1; L76200.1; U50532.1; BC006547.2; BC008797.2; BC000807.1; AL080112.1; BC033718.1///BC046176.1///BC038443.1; NM_000346.1; BC008710.1; Hs.288575 (UNIGENE ID); AF020591.1; BC000423.2; BC002503.2; BC008710.1; BC009185.2; Hs.528304 (UNIGENE ID); U50532.1; BC013923.2; BC031091; NM_007062; Hs.249591 (Unigene ID); BC075839.1///BC073760.1; BC072436.1///BC004560.2; BC001016.2; Hs.286261 (Unigene ID); AF348514.1; BC005023.1; BC066337.1///BC058736.1///BC050555.1; Hs.216623 (Unigene ID); BC072400.1; BC041073.1; U43965.1; BC021258.2; BC016057.1; BC016713.1/// BC014535.1///AF237771.1; BC000360.2; BC007455.2; BC000701.2; BC010067.2; BC023528.2///BC047680.1; BC064957.1; Hs.156701 (Unigene ID); BC030619.2; BC008710.1; U43965.1; BC066329.1; Hs.438867 (Unigene ID); BC035025.2///BC050330.1; BC023976.2; BC074852.2///BC074851.2; Hs.445885 (Unigene ID); BC008591.2///BC050440.1///; BC048096.1; AF365931.1; AF257099.1; and BC028912.1.

In one embodiment, the invention provides a gene group the expression profile of nasal epithelial cells which is useful in diagnosing lung diseases and comprises probes that hybridize to at least, for example 5, 10, 15, 20, 25, 30, preferably at least about 36, still more preferably at least to 40, still more preferably at least to 45, still more preferably all of the following 50 gene sequences, although it can include any and all members, for example, 20, 21, 22, up to and including 36: NM_007062.1; NM_001281.1; BC000120.1; NM_014255.1; BC002642.1; NM_000346.1; NM_006545.1; BG034328; NM_021822.1; NM_021069.1; NM_019067.1; NM_017925.1; NM_017932.1; NM_030757.1; NM_030972.1; AF126181.1; U93240.1; U90552.1; AF151056.1; U85430:1; U51007.1; BC005969.1; NM_002271.1; AL566172; AB014576.1; BF218804; AK022494.1; AAI 14843; BE467941; NM_003541.1; R83000; AL161952.1; AK023843.1; AK021571.1; AK023783.1; AU147182; AL080112.1; AW971983; AI683552; NM_024006.1; AK026565.1; NM_014182.1; NM_021800.1; NM_016049.1; NM_019023.1; NM_021971.1; NM_014128.1; AK025651.1; AA133341; and AF198444.1. In one preferred embodiment, one cart use at least 20-30, 30-40, of the 50 genes that overlap with the individual predictor genes identified in the analysis using the t-test, and, for example, 5-9 of the non-overlapping genes, identified using the t-test analysis as individual predictor genes, and combinations thereof.

In one embodiment, the invention provides a gene group the expression profile of nasal epithelial cells which is useful in diagnosing lung diseases and comprises probes that hybridize to at least for example 5, 10, 15, 20, preferably at least about 25, still more preferably at least to 30, still more preferably all of the following 36 gene sequences: NM_007062.1; NM_001281.1; BC002642.1; NM_000346.1; NM_006545.1; BG034328; NM_019067.1; NM_017925.1; NM_017932.1; NM_030757.1; NM_030972.1; NM_002268///NM_032771; NM_007048/// NM_194441; NM_006694; U85430.1; NM_004691; AB014576.1; BF218804; BE467941; R83000; AL161952.1; AK023843.1; AK021571.1; AK023783.1; AL080112.1; AW971983; AI683552; NM_024006.1; AK026565.1; NM_014182.1; NM_021800.1; NM_016049.1; NM_021971.1; NM_014128.1; AA133341; and AF198444.1. In one preferred embodiment, one can use at least 20 of the 36 genes that overlap with the individual predictors and, for example, 5-9 of the non-overlapping genes, and combination thereof.

The expression of the gene groups in an individual sample can be analyzed using any probe specific to the nucleic acid sequences or protein product sequences encoded by the gene group members. For example, in one embodiment, a probe set useful in the methods of the present invention is selected from the nucleic acid probes of between 10-15, 15-20, 20-180, preferably between 30-180, still more preferably between 36-96, still more preferably between 36-84, still more preferably between 36-50 probes, included in the Affymetrix Inc. gene chip of the Human Genome U133 Set and identified as probe ID Nos: 208082_x_at, 214800_x_at, 215208_x_at, 218556_at, 207730_x_at, 210556_at, 217679_x_at, 202901_x_at, 213939_s_at, 208137_x_at, 214705_at, 215001_s_at, 218155_x_at, 215604_x_at, 212297_at, 201804_x_at, 217949_s_at, 215179_x_at, 211316_x_at, 217653_ x_at, 266_s_at, 204718_at, 211916_s_at, 215032_at, 219920_s_at, 211996_s_at, 200075_s_at, 214753_at, 204102_s_at, 202419_at, 214715_x_at, 216859_x_at, 215529x_at, 202936_s_at, 212130_x_at, 215204_at, 218735_s_at, 200078_s_at, 203455_s_at, 212227_x_at, 222282_at, 219678_x_at, 208268_at, 221899_at, 213721_at, 214718_at, 201608_s_at, 205684_s_at, 209008_x_at, 200825_s_at, 218160_at, 57739_at, 211921_x_at, 218074_at, 200914_x_at, 216384_x_at, 214594_x_at, 222122_s_at, 204060_s_at, 215314_at, 208238_x_at, 210705_s_at, 211184_s_at, 215418_at, 209393_x_at, 210101_x_at, 212052_s_at, 215011_at, 221932_s_at, 201239_s_at, 215553_x_at, 213351_s_at, 202021_x_at, 209442_x_at, 210131_x_at, 217713_x_at, 214707_x_at, 203272_s_at, 206279_at, 214912_at, 201729_s_at, 205917_at, 200772_x_at, 202842_s_at, 203588_s_at, 209703_x_at, 217313_at, 217588_at, 214153_at, 222155_s_at, 203704_s_at, 220934_s_at, 206929_s_at, 220459_at, 215645_at, 217336_at, 203301_s_at, 207283_at, 222168_at, 222272_x_at, 219290_x_at, 204119_s_at, 215387_x_at, 222358_x_at, 205010_at, 1316_at, 216187_x_at, 208678 at, 222310_at, 210434_x_at, 220242_x_at, 207287_at, 207953_at, 209015_s_at, 221759_at, 220856_x_at, 200654_at, 220071_x_at, 216745_x_at, 218976_at, 214833_at, 202004_x_at, 209653_at, 210858_x_at, 212041_at, 221294_at, 207020_at, 204461_x_at, 205367_at, 219203_at, 215067_x_at, 212517_at, 220215_at, 201923_at, 215609_at, 207984_s_at, 215373_x_at, 216110_x_at, 215600_x_at, 216922_x_at, 215892_at, 201530_x_at, 217371_s_at, 222231_s_at, 218265_at, 201537_s_at, 221616_s_at, 213106_at, 215336_at, 209770_at, 209061_at, 202573_at, 207064_s_at, 64371_at, 219977_at, 218617_at, 214902_x_at, 207436_x_at, 215659_at, 204216_s_at, 214763_at, 200877_at, 218425_at, 203246_s_at, 203466_at, 204247_s_at, 216012 at, 211328_x_at, 218336_at, 209746_s_at, 214722_at, 214599_at, 220113_x_at, 213212_x_at, 217671_at, 207365_x_at, 218067_s_at, 205238 at, 209432_s_at, and 213919_at. In one preferred embodiment, one can use at least, for example, 10-20, 20-30, 30-40, 40-50, 50-60, 60-70, 70-80, 80-90, 90-100; 110, 120, 130, 140, 150, 160, or 170 of the 180 genes that overlap with the individual predictors genes and, for example, 5-9 of the non-overlapping genes and combinations thereof.

Sequences for the Affymetrix probes are available from Affymetrix. Other probes and sequences that recognize the genes of interest can be easily prepared using, e.g. synthetic oligonucleotides recombinant oligonucleotides. These sequences can be selected from any, preferably unique part of the gene based on the sequence information publicly available for the genes that are indicated by their HUGO ID, GenBank No. or Unigene No.

One can analyze the expression data to identify expression patters associated with any lung disease. For example, one can analyze diseases caused by exposure to air pollutants, such as cigarette smoke, asbestos or any other pollutant. For example, the analysis can be performed as follows. One first scans a gene chip or mixture of beads comprising probes that are hybridized with a study group samples. For example, one can use samples of non-smokers and smokers, non-asbestos exposed individuals and asbestos-exposed individuals, non-smog exposed individuals and smog-exposed individuals, smokers without a lung disease and smokers with lung disease, to obtain the differentially expressed gene groups between individuals with no lung disease and individuals with lung disease. One must, of course select appropriate groups, wherein only one air pollutant can be selected as a variable. So, for example, one can compare non-smokers exposed to asbestos but not smog and non-smokers not exposed to asbestos or smog.

The obtained expression analysis, such as microarray or microbead raw data consists of signal strength and detection p-value. One normalizes or scales the data, and filters the poor quality chips/bead sets based on images of the expression data, control probes, and histograms. One also filters contaminated specimens which contain non-epithelial cells.

Lastly, one filters the genes of importance using detection p-value. This results in identification of transcripts present in normal airways (normal airway transcriptome). Variability and multiple regression analysis can be used. This also results in identification of effects of smoking on airway epithelial cell transcription. For this analysis, one can use T-test and Pearson correlation analysis. One can also identify a group or a set of transcripts that are differentially expressed in samples with lung disease, such as lung cancer and samples without cancer. This analysis was performed using class prediction models.

For analysis of the data, one can use, for example, a weighted voting method. The weighted voting method ranks, and gives a weight "p" to all genes by the signal to noise ration of gene expression between two classes: $P=mean_{(class\ 1)} - mean_{(class\ 2)} sd_{(class\ 1)} = sd_{(class\ 2)}$. Committees of variable sizes of the top ranked genes are used to evaluate test samples, but genes with more significant p-values can be more heavily weighed. Each committee genes in test sample votes for one class or the other, based on how close that gene expression level is to the class 1 mean or the class 2 mean. $V_{(gene\ A)} = P_{(gene\ A)}$, i.e. level of expression in test sample less the average of the mean expression values in the two classes. Votes for each class are tallied and the winning class is determined along with prediction strength as $PS = V_{win} - V_{lose}/V_{win} + V_{lose}$. Finally, the accuracy can be validated using cross-validation+/− independent samples.

Table 1 shows 96 genes that were identified as a group distinguishing smokers with cancer from smokers without cancer. The difference in expression is indicated at the column on the right as either "down", which indicates that the expression of that particular transcript was lower in smokers with cancer than in smokers without cancer, and "up", which indicates that the expression of that particular transcript was higher in smokers with cancer than smokers without cancer. In one embodiment, the exemplary probes shown in the Column "Affymetrix Id in the Human Genome U133 chip" can be used.

TABLE 1

96 Gene Group

| Affymetrix ID for an example probe identifying the gene | GenBank ID | Gene Name | Expression in cancer compared to a sample with no cancer. |
|---|---|---|---|
| 1316_at | NM_003335 | UBE1L | down |
| 200654_at | NM_000918 | P4HB | up |
| 200877_at | NM_006430.1 | CCT4 | up |
| 201530_x_at | NM_001416.1 | EIF4A1 | up |
| 201537_s_at | NM_004090 | DUSP3 | up |
| 201923_at | NM_006406.1 | PRDX4 | up |
| 202004_x_at | NM_003001.2 | SDHC | up |
| 202573_at | NM_001319 | CSNK1G2 | down |
| 203246_s_at | NM_006545.1 | TUSC4 | up |
| 203301_s_at | NM_021145.1 | DMTF1 | down |
| 203466_at | NM_002437.1 | MPV17 | up |

TABLE 1-continued

96 Gene Group

| Affymetrix ID for an example probe identifying the gene | GenBank ID | Gene Name | Expression in cancer compared to a sample with no cancer. |
|---|---|---|---|
| 203588_s_at | NM_006286 | TFDP2 | up |
| 203704_s_at | NM_001003698 /// NM_001003699 /// NM_002955 | RREB1 | down |
| 204119_s_at | NM_001123 /// NM_006721 | ADK | up |
| 204216_s_at | NM_024824 | FLJ11806 | up |
| 204247_s_at | NM_004935.1 | CDK5 | up |
| 204461_x_at | NM_002853.1 | RAD1 | down |
| 205010_at | NM_019067.1 | FLJ10613 | down |
| 205238_at | NM_024917.1 | CXorf34 | down |
| 205367_at | NM_020979.1 | APS | down |
| 206929_s_at | NM_005597.1 | NFIC | down |
| 207020_at | NM_007031.1 | HSF2BP | down |
| 207064_s_at | NM_009590.1 | AOC2 | down |
| 207283_at | NM_020217.1 | DKFZp547I014 | down |
| 207287_at | NM_025026.1 | FLJ14107 | down |
| 207365_x_at | NM_014709.1 | USP34 | down |
| 207436_x_at | NM_014896.1 | KIAA0894 | down |
| 207953_at | AF010144 | — | down |
| 207984_s_at | NM_005374.1 | MPP2 | down |
| 208678_at | NM_001696 | ATP6V1E1 | up |
| 209015_s_at | NM_005494 /// NM_058246 | DNAJB6 | up |
| 209061_at | NM_006534 /// NM_181659 | NCOA3 | down |
| 209432_s_at | NM_006368 | CREB3 | up |
| 209653_at | NM_002268 /// NM_032771 | KPNA4 | up |
| 209703_x_at | NM_014033 | DKFZP586A0522 | down |
| 209746_s_at | NM_016138 | COQ7 | down |
| 209770_at | NM_007048 /// NM_194441 | BTN3A1 | down |
| 210434_x_at | NM_006694 | JTB | up |
| 210858_x_at | NM_000051 /// NM_138292 /// NM_138293 | ATM | down |
| 211328_x_at | NM_000410 /// NM_139002 /// NM_139003 /// NM_139004 /// NM_139005 /// NM_139006 /// NM_139007 /// NM_139008 /// NM_139009 /// NM_139010 /// NM_139011 | HFE | down |
| 212041_at | NM_004691 | ATP6V0D1 | up |
| 212517_at | NM_012070 /// NM_139321 /// NM_139322 | ATRN | down |
| 213106_at | NM_006095 | ATP8A1 | down |
| 213212_x_at | AI632181 | — | down |
| 213919_at | AW024467 | — | down |
| 214153_at | NM_021814 | ELOVL5 | down |
| 214599_at | NM_005547.1 | IVL | down |
| 214722_at | NM_203458 | N2N | down |
| 214763_at | NM_015547 /// NM_147161 | THEA | down |
| 214833_at | AB007958.1 | KIAA0792 | down |
| 214902_x_at | NM_207488 | FLJ42393 | down |
| 215067_x_at | NM_005809 /// NM_181737 /// NM_181738 | PRDX2 | down |
| 215336_at | NM_016248 /// NM_144490 | AKAP11 | down |
| 215373_x_at | AK022213.1 | FLJ12151 | down |
| 215387_x_at | NM_005708 | GPC6 | down |
| 215600_x_at | NM_207102 | FBXW12 | down |
| 215609_at | AK023895 | — | down |
| 215645_at | NM_144606 /// NM_144997 | FLCN | down |
| 215659_at | NM_018530 | GSDML | down |
| 215892_at | AK021474 | — | down |
| 216012_at | U43604.1 | — | down |
| 216110_x_at | AU147017 | — | down |
| 216187_x_at | AF222691.1 | LNX1 | down |
| 216745_x_at | NM_015116 | LRCH1 | down |
| 216922_x_at | NM_001005375 /// NM_001005785 /// NM_001005786 /// NM_004081 /// NM_020363 /// NM_020364 /// NM_020420 | DAZ2 | down |
| 217313_at | AC004692 | — | down |
| 217336_at | NM_001014 | RPS10 | down |
| 217371_s_at | NM_000585 /// NM_172174 /// NM_172175 | IL15 | down |
| 217588_at | NM_054020 /// NM_172095 /// NM_172096 /// NM_172097 | CATSPER2 | down |
| 217671_at | BE466926 | — | down |
| 218067_s_at | NM_018011 | FLJ10154 | down |
| 218265_at | NM_024077 | SECISBP2 | down |
| 218336_at | NM_012394 | PFDN2 | up |
| 218425_at | NM_019011 /// NM_207111 /// NM_207116 | TRIAD3 | down |
| 218617_at | NM_017646 | TRIT1 | down |
| 218976_at | NM_021800 | DNAJC12 | up |
| 219203_at | NM_016049 | C14orf122 | up |
| 219290_x_at | NM_014395 | DAPP1 | down |
| 219977_at | NM_014336 | AIPL1 | down |
| 220071_x_at | NM_018097 | C15orf25 | down |
| 220113_x_at | NM_019014 | POLR1B | down |
| 220215_at | NM_024804 | FLJ12606 | down |
| 220242_x_at | NM_018260 | FLJ10891 | down |
| 220459_at | NM_018118 | MCM3APAS | down |
| 220856_at | NM_014128 | — | down |
| 220934_s_at | NM_024084 | MGC3196 | down |
| 221294_at | NM_005294 | GPR21 | down |
| 221616_s_at | AF077053 | PGK1 | down |
| 221759_at | NM_138387 | G6PC3 | up |
| 222155_s_at | NM_024531 | GPR172A | up |
| 222168_at | NM_000693 | ALDH1A3 | down |
| 222231_s_at | NM_018509 | PRO1855 | up |
| 222272_x_at | NM_033128 | SCIN | down |
| 222310_at | NM_020706 | SFRS15 | down |
| 222358_x_at | AI523613 | — | down |
| 64371_at | NM_014884 | SFRS14 | down |

Table 2 shows one preferred 84 gene group that has been identified as a group distinguishing smokers with cancer from smokers without cancer. The difference in expression is indicated at the column on the right as either "down", which indicates that the expression of that particular transcript was lower in smokers with cancer than in smokers without cancer, and "up", which indicates that the expression of that particular transcript was higher in smokers with cancer than smokers without cancer. These genes were identified using traditional Student's t-test analysis.

In one embodiment, the exemplary probes shown in the column "Affymetrix Id in the Human Genome U133 chip" can be used in the expression analysis.

TABLE 2

84 Gene Group

| GenBank ID (unless otherwise mentioned) | Gene Name Abbreviation | Direction in Cancer compared to a non-cancer sample | Affymetrix ID |
|---|---|---|---|
| NM_030757.1 | MKRN4 | down | 208082_x_at |
| R83000 | BTF3 | down | 214800_x_at |
| AK021571.1 | MUC20 | down | 215208_x_at |
| NM_014182.1 | ORMDL2 | up | 218556_at |
| NM_17932.1 | FLJ20700 | down | 207730_x_at |
| U85430.1 | NFATC3 | down | 210556_at |
| AI683552 | — | down | 217679_x_at |
| BC002642.1 | CTSS | down | 202901_x_at |
| AW024467 | RIPX | down | 213939_s_at |
| NM_030972.1 | MGC5384 | down | 208137_x_at |
| BC021135.1 | INADL | down | 214705_at |
| AL161952.1 | GLUL | down | 215001_s_at |
| AK026565.1 | FLJ10534 | down | 218155_s_at |
| AK023783.1 | — | down | 215604_x_at |
| BF218804 | AFURS1 | down | 212297_at |
| NM_001281.1 | CKAP1 | up | 201804_x_at |
| NM_024006.1 | IMAGE3455200 | up | 217949_s_at |
| AK023843.1 | PGF | down | 215179_x_at |
| BC001602.1 | CFLAR | down | 211316_x_at |
| BC034707.1 | — | down | 217653_x_at |
| BC064619.1 | CD24 | down | 266_s_at |
| AY280502.1 | EPHB6 | down | 204718_at |
| BC059387.1 | MYO1A | down | 211916_s_at |
| | — | down | 215032_at |
| AF135421.1 | GMPPB | up | 219920_s_at |
| BC061522.1 | MGC70907 | down | 211996_s_at |
| L76200.1 | GUK1 | up | 200075_s_at |
| U50532.1 | CG005 | down | 214753_at |
| BC006547.2 | EEF2 | down | 204102_s_at |
| BC008797.2 | FVT1 | down | 202419_at |
| BC000807.1 | ZNF160 | down | 214715_at |
| AL080112.1 | — | down | 216859_x_at |
| BC033718.1 /// BC046176.1 /// BC038443.1 | C21orf106 | down | 215529_x_at |
| NM_000346.1 | SOX9 | up | 202936_s_at |
| BC008710.1 | SUI1 | up | 212130_x_at |
| Hs.288575 (Unigene ID) | — | down | 215204_at |
| AF020591.1 | AF020591 | down | 218735_s_at |
| BC000423.2 | ATP6V0B | up | 200078_s_at |
| BC002503.2 | SAT | down | 203455_s_at |
| BC008710.1 | SUI1 | up | 212227_x_at |
| | — | down | 222282_at |
| BC009185.2 | DCLRE1C | down | 219678_x_at |
| Hs.528304 (UNIGENE ID) | ADAM28 | down | 208268_at |
| U50532.1 | CG005 | down | 221899_at |
| BC013923.2 | SOX2 | down | 213721_at |
| BC031091 | ODAG | down | 214718_at |
| NM_007062 | PWP1 | up | 201608_s_at |
| Hs.249591 (Unigene ID) | FLJ20686 | down | 205684_s_at |
| BC075839.1 /// BC073760.1 | KRT8 | up | 209008_s_at |
| BC072436.1 /// BC004560.2 | HYOU1 | up | 200825_s_at |
| BC001016.2 | NDUFA8 | up | 218160_at |
| Hs.286261 (Unigene ID) | FLJ20195 | down | 57739_at |
| AF348514.1 | — | down | 211921_x_at |
| BC005023.1 | CGI-128 | up | 218074_at |
| BC066337.1 /// BC058736.1 /// BC050555.1 | KTN1 | down | 200914_x_at |
| | — | down | 216384_x_at |
| Hs.216623 (Unigene ID) | ATP8B1 | down | 214594_at |
| BC072400.1 | THOC2 | down | 222122_s_at |
| BC041073.1 | PRKX | down | 204060_s_at |
| U43965.1 | ANK3 | down | 215314_at |
| | — | down | 208238_x_at |
| BC021258.2 | TRIM5 | down | 210705_s_at |
| BC016057.1 | USH1C | down | 211184_s_at |
| BC016713.1 /// BC014535.1 /// AF237771.1 | PARVA | down | 215418_at |
| BC000360.2 | EIF4EL3 | up | 209393_s_at |
| BC007455.2 | SH3GLB1 | up | 210101_x_at |
| BC000701.2 | KIAA0676 | down | 212052_s_at |
| BC010067.2 | CHC1 | down | 215011_at |
| BC023528.2 /// BC047680.1 | C14orf87 | up | 221932_s_at |
| BC064957.1 | KIAA0102 | up | 201239_s_at |
| Hs.156701 (Unigene ID) | — | down | 215553_x_at |
| BC030619.2 | KIAA0779 | down | 213351_s_at |
| BC008710.1 | SUI1 | up | 202021_x_at |
| U43965.1 | ANK3 | down | 209442_x_at |
| BC066329.1 | SDHC | up | 210131_x_at |
| Hs.438867 (Unigene ID) | — | down | 217713_x_at |
| BC035025.2 /// BC050330.1 | ALMS1 | down | 214707_x_at |
| BC023976.2 | PDAP2 | up | 203272_s_at |
| BC074852.2 /// BC074851.2 | PRKY | down | 206279_at |
| Hs.445885 (Unigene ID) | KIAA1217 | down | 214912_at |
| BC008591.2 /// BC050440.1 /// BC048096.1 | KIAA0100 | up | 201729_s_at |
| AF365931.1 | ZNF264 | down | 205917_at |
| AF257099.1 | PTMA | down | 200772_x_at |
| BC028912.1 | DNAJB9 | up | 202842_s_at |

Table 3 shows one preferred 50 gene group that was identified as a group distinguishing smokers with cancer from smokers without cancer. The difference in expression is indicated at the column on the right as either "down", which indicates that the expression of that particular transcript was lower in smokers with cancer than in smokers without cancer, and "up", which indicates that the expression of that particular transcript was higher in smokers with cancer than smokers without cancer.

This gene group was identified using the GenePattern server from the Broad Institute, which includes the Weighted Voting algorithm. The default settings, i.e., the signal to noise ratio and no gene filtering, were used.

In one embodiment, the exemplary probes shown in the column "Affymetrix Id in the Human Genome U133 chip" can be used in the expression analysis.

TABLE 3

50 Gene Group

| GenBank ID | Gene Name | Direction in Cancer | Affymetrix ID |
|---|---|---|---|
| NM_007062.1 | PWP1 | up in cancer | 201608_s_at |
| NM_001281.1 | CKAP1 | up in cancer | 201804_x_at |
| BC000120.1 | | up in cancer | 202355_s_at |
| NM_014255.1 | TMEM4 | up in cancer | 202857_at |
| BC002642.1 | CTSS | up in cancer | 202901_x_at |
| NM_000346.1 | SOX9 | up in cancer | 202936_s_at |
| NM_006545.1 | NPR2L | up in cancer | 203246_s_at |
| BG034328 | | up in cancer | 203588_s_at |
| NM_021822.1 | APOBEC3G | up in cancer | 204205_at |
| NM_021069.1 | ARGBP2 | up in cancer | 204288_s_at |

TABLE 3-continued

50 Gene Group

| GenBank ID | Gene Name | Direction in Cancer | Affymetrix ID |
|---|---|---|---|
| NM_019067.1 | FLJ10613 | up in cancer | 205010_at |
| NM_017925.1 | FLJ20686 | up in cancer | 205684_s_at |
| NM_017932.1 | FLJ20700 | up in cancer | 207730_x_at |
| NM_030757.1 | MKRN4 | up in cancer | 208082_x_at |
| NM_030972.1 | MGC5384 | up in cancer | 208137_x_at |
| AF126181.1 | BCG1 | up in cancer | 208682_s_at |
| U93240.1 | | up in cancer | 209653_at |
| U90552.1 | | up in cancer | 209770_at |
| AF151056.1 | | up in cancer | 210434_x_at |
| U85430.1 | NFATC3 | up in cancer | 210556_at |
| U51007.1 | | up in cancer | 211609_x_at |
| BC005969.1 | | up in cancer | 211759_x_at |
| NM_002271.1 | | up in cancer | 211954_s_at |
| AL566172 | | up in cancer | 212041_at |
| AB014576.1 | KIAA0676 | up in cancer | 212052_s_at |
| BF218804 | AFURS1 | down in cancer | 212297_at |
| AK022494.1 | | down in cancer | 212932_at |
| AA114843 | | down in cancer | 213884_s_at |
| BE467941 | | down in cancer | 214153_at |
| NM_003541.1 | HIST1H4K | down in cancer | 214463_x_at |
| R83000 | BTF3 | down in cancer | 214800_x_at |
| AL161952.1 | GLUL | down in cancer | 215001_s_at |
| AK023843.1 | PGF | down in cancer | 215179_x_at |
| AK021571.1 | MUC20 | down in cancer | 215208_x_at |
| AK023783.1 | — | down in cancer | 215604_x_at |
| AU147182 | | down in cancer | 215620_at |
| AL080112.1 | — | down in cancer | 216859_x_at |
| AW971983 | | down in cancer | 217588_at |
| AI683552 | — | down in cancer | 217679_x_at |
| NM_024006.1 | IMAGE3455200 | down in cancer | 217949_s_at |
| AK026565.1 | FLJ10534 | down in cancer | 218155_x_at |
| NM_014182.1 | ORMDL2 | down in cancer | 218556_at |
| NM_021800.1 | DNAJC12 | down in cancer | 218976_at |
| NM_016049.1 | CGI-112 | down in cancer | 219203_at |
| NM_019023.1 | PRMT7 | down in cancer | 219408_at |
| NM_021971.1 | GMPPB | down in cancer | 219920_s_at |
| NM_014128.1 | — | down in cancer | 220856_x_at |
| AK025651.1 | | down in cancer | 221648_s_at |
| AA133341 | C14orf87 | down in cancer | 221932_s_at |
| AF198444.1 | | down in cancer | 222168_at |

Table 4 shows one preferred 36 gene group that was identified as a group distinguishing smokers with cancer from smokers without cancer. The difference in expression is indicated at the Column on the right as either "down", which indicates that the expression of that particular transcript was lower in smokers with cancer than in smokers without cancer, and "up", which indicates that the expression of that particular transcript was higher in smokers with cancer than smokers without cancer.

In one embodiment, the exemplary probes shown in the column "Affymetrix Id in the Human Genome U133 chip" can be used in the expression analysis.

TABLE 4

36 Gene Group

| GenBank ID | Gene Name | Affymetrix ID |
|---|---|---|
| NM_007062.1 | PWP1 | 201608_s_at |
| NM_001281.1 | CKAP1 | 201804_x_at |
| BC002642.1 | CTSS | 202901_x_at |
| NM_000346.1 | SOX9 | 202936_s_at |
| NM_006545.1 | NPR2L | 203246_s_at |
| BG034328 | | 203588_s_at |
| NM_019067.1 | FLJ10613 | 205010_at |
| NM_017925.1 | FLJ20686 | 205684_s_at |
| NM_017932.1 | FLJ20700 | 207730_x_at |
| NM_030757.1 | MKRN4 | 208082_x_at |
| NM_030972.1 | MGC5384 | 208137_x_at |
| NM_002268 /// NM_032771 | KPNA4 | 209653_at |
| NM_007048 /// NM_194441 | BTN3A1 | 209770_at |
| NM_006694 | JBT | 210434_x_at |
| U85430.1 | NFATC3 | 210556_at |
| NM_004691 | ATP6V0D1 | 212041_at |
| AB014576.1 | KIAA0676 | 212052_s_at |
| BF218804 | AFURS1 | 212297_at |
| BE467941 | | 214153_at |
| R83000 | BTF3 | 214800_x_at |
| AL161952.1 | GLUL | 215001_s_at |
| AK023843.1 | PGF | 215179_x_at |
| AK021571.1 | MUC20 | 215208_x_at |
| AK023783.1 | — | 215604_x_at |
| AL080112.1 | — | 216859_x_at |
| AW971983 | | 217588_at |
| AI683552 | — | 217679_x_at |
| NM_024006.1 | IMAGE3455200 | 217949_s_at |
| AK026565.1 | FLJ10534 | 218155_x_at |
| NM_014182.1 | ORMDL2 | 218556_at |
| NM_021800.1 | DNAJC12 | 218976_at |
| NM_016049.1 | CGI-112 | 219203_at |
| NM_021971.1 | GMPPB | 219920_s_at |
| NM_014128.1 | — | 220856_x_at |
| AA133341 | C14orf87 | 221932_s_at |
| AF198444.1 | | 222168_at |

In one embodiment, the gene group of the present invention comprises at least, for example, 5, 10, 15, 20, 25, 30, more preferably at least 36, still more preferably at least about 40 still more preferably at least about 50, still more preferably at least about 60, still more preferably at least about 70, still more preferably at least about 80, still more preferably at least about 86, still more preferably at least about 90, still more preferably at least about 96 of the genes as shown in Tables 1-4.

In one preferred embodiment, the gene group comprises 36-180 genes selected worn the group consisting of the genes listed in Tables 1-4.

In one embodiment, the invention provides group of genes the expression of which is lower in individuals with cancer.

Accordingly, in one embodiment, the invention provides of a group of genes useful in diagnosing lung diseases, wherein the expression of the group of genes is lower in individuals exposed to air pollutants with cancer as compared to individuals exposed to the same air pollutant who do not have cancer, the group comprising probes that hybridize at least 5, preferably at least about 5-10, still more preferably at least about 10-20, still more preferably at least about 20-30, still more preferably at least about 30-40, still more preferably at least about 40-50, still more preferably at least about 50-60, still more preferably at least about 60-70, still more preferably about 72 genes consisting of transcripts (transcripts are identified using their GenBank ID or Unigene ID numbers and the corresponding gene names appear in Table 1): NM_003335; NM_001319; NM_021145.1; NM_001003698///NM_001003699///; NM_002955; NM_002853.1; NM_019067.1; NM_024917.1; NM_020979.1; NM_005597.1; NM_007031.1; NM_009590.1; NM_020217.1; NM_025026.1; NM_014709.1; NM_014896.1; AF010144; NM_005374.1; NM_006534///NM_181659; NM_014033; NM_016138; NM_007048///NM_194441; NM_000051///NM_138292///NM_138293; NM_000410///NM_139002///NM_139003///NM_139004///NM_139005///NM_139006///NM_139007///NM_139008///NM_139009///NM_139010///NM_139011;

NM_012070///NM_139321///NM_139322; NM_006095; AI632181; AW024467; NM_021814; NM_005547.1; NM_203458; NM_015547///NM_147161; AB007958.1; NM_207488; NM_005809///NM_181737///NM_181738; NM_016248///NM_144490; AK022213.1; NM_005708; NM_207102; AK023895; NM_144606///NM_144997; NM_018530; AK021474; U43604.1; AU147017; AF222691.1; NM_015116; NM_001005375///NM_001005785///NM_001005786///NM_004081///NM_020363///NM_020364///NM_020420; AC004692; NM_001014; NM_000585///NM_172174///NM_172175; NM_054020///NM_172095///NM_172096///NM_172097; BE466926; NM_018011; NM_024077; NM_019011///NM_207111///NM_207116; NM_017646; NM_014395; NM_014336; NM_018097; NM_019014; NM_024804; NM_018260; NM_018118; NM_014128; NM_024084; NM_005294; AF077053; NM_000693; NM_033128; NM_020706; AI523613; and NM_014884.

In another embodiment, the invention provides of a group of genes useful in diagnosing lung diseases wherein the expression of the group of genes is lower in individuals exposed to air pollutants with cancer as compared to individuals exposed to the same air pollutant who do not have cancer, the group comprising probes that hybridize at least 5, preferably at least about 5-10, still more preferably at least about 10-20, still more preferably at least about 20-30, still more preferably at least about 30-40, still more preferably at least about 40-50, still more preferably at least about 50-60, still more preferably about 63 genes consisting of transcripts (transcripts are identified using their GenBank ID or Unigene ID numbers and the corresponding gene names appear in Table 2): NM_030757.1; R83000; AK021571.1; NM_17932.1; U85430.1; AI683552; BC002642.1; AW024467; NM_030972.1; BC021135.1; AL161952.1; AK026565.1; AK023783.1; BF218804; AK023843.1; BC001602.1; BC034707.1; BC064619.1; AY280502.1; BC059387.1; BC061522.1; U50532.1; BC006547.2; BC008797.2; BC000807.1; AL080112.1; BC033718.1///BC046176.1///; BC038443.1; Hs.288575 (UNIGENE ID); AF020591.1; BC002503.2; BC009185.2; Hs.528304 (UNIGENE ID); U50532.1; BC013923.2; BC031091; Hs.249591 (Unigene ID); Hs.286261 (Unigene ID); AF348514.1; BC066337.1///BC058736.1///BC050555.1; Hs.216623 (Unigene ID); BC072400.1; BC041073.1; U43965.1; BC021258.2; BC016057.1; BC016713.1///BC014535.1///AF237771.1; BC000701.2; BC010067.2; Hs.156701 (Unigene ID); BC030619.2; U43965.1; Hs.438867 (Unigene ID); BC035025.2///BC050330.1; BC074852.2///BC074851.2; Hs.445885 (Unigene ID); AF365931.1; and AF257099.1

In another embodiment, the invention provides of a group of genes useful in diagnosing lung diseases wherein the expression of the group of genes is lower in individuals exposed to air pollutants with cancer as compared to individuals exposed to the same air pollutant who do not have cancer, the group comprising probes that hybridize at least 5, preferably at least about 5-10, still more preferably at least about 10-20, still more preferably at least about 20-25, still more preferably, about 25 genes consisting of transcripts (transcripts are identified using their GenBank ID or Unigene ID numbers and the corresponding gene names appear in Table 3):BF218804; AK022494.1; AA114843; BE467941; NM_003541.1; R83000; AL161952.1; AK023843.1; AK021571.1; AK023783.1; AU147182; AL080112.1; AW971983; AI683552; NM_024006.1; AK026565.1; NM_014182.1; NM_021800.1; NM_016049.1; NM_019023.1; NM_021971.1; NM_014128.1; AK025651.1; AA133341; and AF198444.1.

In another embodiment, the invention provides of a group of genes useful in diagnosing lung diseases wherein the expression of the group of genes is higher in individuals exposed to air pollutants with cancer as compared to individuals exposed to the same air pollutant who do not have cancer, the group comprising probes that hybridize at least to 5, preferably at least about 5-10, still more preferably at least about 10-20, still more preferably at least about 20-25, still more preferably about 25 genes consisting of transcripts (transcripts are identified using their GenBank 11) or Unigene ID numbers and the corresponding gene names appear in Table 1): NM_000918; NM_006430.1; NM_001416.1; NM_004090; NM_006406.1; NM_003001.2; NM_006545.1; NM_002437.1; NM_006286; NM_001123///NM_006721; NM_024824; NM_004935.1; NM_001696; NM_005494///NM_058246; NM_006368; NM_002268///NM_032771; NM_006694; NM_004691; NM_012394; NM_021800; NM_016049; NM_138387; NM_024531; and NM_018509.

In another embodiment, the invention provides of a group of genes useful in diagnosing lung diseases wherein the expression of the group of genes is higher in individuals exposed to air pollutants with cancer as compared to individuals exposed to the same air pollutant who do not have cancer, the group comprising probes that hybridize at least to 5, preferably at least about 5-10, still more preferably at least about 10-20, still more preferably at least about 20-23, still more preferably about 23 genes consisting of transcripts (transcripts are identified using their GenBank ID or Unigene ID numbers and the corresponding gene names appear in Table 2): NM_014182.1; NM_001281.1; NM_024006.1; AF135421.1; L76200.1; NM_000346.1; BC008710.1; BC000423.2; BC008710.1; NM_007062; BC075839.1///BC073760.1; BC072436.1///BC004560.2; BC001016.2; BC005023.1; BC000360.2; BC007455.2; BC023528.2///BC047680.1; BC064957.1; BC008710.1; BC066329.1; BC023976.2; BC008591.2///BC050440.1///BC048096.1; and BC28912.1.

In another embodiment, the invention provides of a group of genes useful in diagnosing lung diseases wherein the expression of the group of genes is higher in individuals exposed to air pollutants with cancer as compared to individuals exposed to the same air pollutant who do not have cancer, the group comprising probes that hybridize at least to 5, preferably at least about 5-10, still more preferably at least about 10-20, still more preferably at least about 20-25, still more preferably about 25 genes consisting of transcripts (transcripts are identified using their GenBank ID or Unigene ID numbers and the corresponding gene names appear in Table 3): NM_007062.1; NM_001281.1; BC000120.1; NM_014255.1; BC002642.1; NM_000346.1; NM_006545.1; BG034328; NM_021822.1; NM_021069.1; NM_019067.1; NM_017925.1; NM_017932.1; NM_030757.1; NM_030972.1; AF126181.1; U93240.1; U90552.1; AF151056.1; U85430.1; U51007.1; BC005969.1; NM_002271.1; AL566172; and AB014576.1.

In one embodiment, the invention provides a method of diagnosing lung disease comprising the steps of measuring the expression profile of a gene group in an individual suspected of being affected or being at high risk of a lung disease (i.e. test individual), and comparing the expression profile (i.e. control profile) to an expression profile of an individual without the lung disease who has also been exposed to similar air pollutant than the test individual (i.e. control individual), wherein differences in the expression of genes when compared between the afore mentioned test individual and control individual of at least 10, more preferably at least 20, still more preferably at least 30, still more preferably at least 36, still more preferably between 36-180, still more preferably between 36-96, still more preferably between 36-84, still more preferably between 36-50, is indicative of the test individual being affected with a lung disease. Groups of about 36 genes as shown in table 4, about 50 genes as shown in table 3, about 84 genes as shown in table 2 and about 96 genes as shown in table 1 are preferred. The different gene groups can also be combined, so that the test individual can be screened for all, three, two, or just one group as shown in tables 1-4.

For example, if the expression profile of a test individual exposed to cigarette smoke is compared to the expression profile of the 50 genes shown in table 3, using the Affymetrix Inc. probe set on a gene chip as shown in table 3, the expression profile that is similar to the one shown in FIG. 10 for the individuals with cancer, is indicative that the test individual has cancer. Alternatively, if the expression profile is more like the expression profile of the individuals who do not have cancer in FIG. 10, the test individual likely is not affected with lung cancer.

The group of 50 genes was identified using the GenePattern server from the Broad Institute, which includes the Weighted Voting algorithm. The default settings, i.e., the signal to noise ratio and no gene filtering, were used. GenePattern is available through the World Wide Web at location broad.mit.edu/cancer/software/genepattern. This program allows analysis of data in groups rather than as individual genes. Thus, in one preferred embodiment, the expression of substantially all 50 genes of Table 3, are analyzed together. The expression profile of lower that normal expression of genes selected from the group consisting of BF218804; AK022494.1; AAI14843; BE467941; NM_003541.1; 883000; AL161952.1; AK023843.1; AK021571.1; AK023783.1; AU147182; AL080112.1; AW971983; AI683552; NM_024006.1; AK026565.1; NM_014182.1; NM_021800.1; NM_016049.1; NM_019023.1; NM_021971.1; NM_014128.1; AK025651.1; AA133341; and AF198444.1, and the gene expression profile of higher than normal expression of genes selected from the group consisting of NM_007062.1; NM_001281.1; BC000120.1; NM_014255.1; BC002642.1; NM_000346.1; NM_006545.1; BG034328; NM_021822.1; NM_021069.1; NM_019067.1; NM_017925.1; NM_017932.1; NM_030757.1; NM_030972.1; AF126181.1; 093240.1; U90552.1; AF151056.1; U85430.1; U51007.1; BC005969.1; NM_002271.1; AL566172; and AB014576.1, is indicative of the individual having or being at high risk of developing lung disease, such as lung cancer. In one preferred embodiment, the expression pattern of all the genes in the Table 3 is analyzed. In one embodiment, in addition to analyzing the group of predictor genes of Table 3, 1, 2, 3.4, 5, 6, 7, 8, 9, 10-15, 15-20, 20-30, or more of the individual predictor genes identified using the t-test analysis are analyzed. Any combination of, for example, 5-10 or more of the group predictor genes and 5-10, or more of the individual genes can also be used.

The term "expression profile" as used herein, refers to the amount of the gene product of each of the analyzed individual genes in the sample. The "expression profile" is like a signature expression map, like the one shown for each individual in FIG. 10, on the Y-axis.

The term "lung disease" as used herein, refers to disorders including, but not limited to, asthma, chronic bronchitis, emphysema, bronchictasis, primary pulmonary hypertension and acute respiratory distress syndrome. The methods described herein may also be used to diagnose or treat lung disorders that involve the immune system including, hypersensitivity pneumonitis, eosinophilic pneumonias, and persistent fungal infections, pulmonary fibrosis, systemic sclerosis, idiopathic pulmonary hemosiderosis, pulmonary alveolar proteinosis, cancers of the lung such as adenocarcinoma, squamous cell carcinoma, small cell and large cell carcinomas, and benign neoplasm of the lung including bronchial adenomas and hamartomas. In one preferred embodiment; the lung disease is lung cancer.

The term "air pollutants", as used herein, refers to any air impurities or environmental airway stress inducing agents, such as cigarette smoke, cigar smoke, smog, asbestos, and other air pollutants that have suspected or proven association to lung diseases.

The term "individual", as used herein, preferably refers to human. However, the methods are not limited to humans, and a skilled artisan can use the diagnostic/prognostic gene groupings of the present invention in, for example, laboratory test animals, preferably animals that have lungs, such as non-human primates, murine species, including, but not limited to rats and mice, dogs, sheep, pig, guinea pigs, and other model animals. Such laboratory tests can be used, for example in pre-clinical animal testing of drugs intended to be used to treat or prevent lung diseases.

The phrase "altered expression" as used herein, refers to either increased or decreased expression in an individual exposed to air pollutant, such as a smoker, with cancer when compared to an expression pattern of the lung cells from an individual exposed to similar air pollutant, such as smoker, who does not have cancer. Tables 1 and 2 show the preferred expression pattern changes of the invention. The terms "up" and "down" in the tables refer to the amount of expression in a smoker with cancer to the amount of expression in a smoker without cancer. Similar expression pattern changes are likely associated with development of cancer in individuals who have been exposed to other airway pollutants.

In one embodiment, the group of genes the expression of which is analyzed in diagnosis and/or prognosis of lung cancer are selected from the group of 80 genes as shown in Table 5. Any combination of genes can be selected from the 80 genes. In one embodiment, the combination of 20 genes shown in Table 7 is selected. In one embodiment, a combination of genes from Table 6 is selected.

TABLE 5

Group of 80 genes for prognostic and diagnostic testing of lung cancer.

| Affymetrix ID | Gene symbol (HUGO ID) | Number of runs* | Signal to noise in a cancer sample** |
|---|---|---|---|
| 200729_s_at | ACTR2 | 736 | −0.22284 |
| 200760_s_at | ARL6IP5 | 483 | −0.21221 |
| 201399_s_at | TRAM1 | 611 | −0.21328 |
| 201444_s_at | ATP6AP2 | 527 | −0.21487 |
| 201635_s_at | FXR1 | 458 | −0.2162 |
| 201689_s_at | TPD52 | 565 | −0.22292 |
| 201925_s_at | DAF | 717 | −0.25875 |
| 201926_s_at | DAF | 591 | −0.23228 |
| 201946_s_at | CCT2 | 954 | −0.24592 |
| 202118_s_at | CPNE3 | 334 | −0.21273 |
| 202704_at | TOB1 | 943 | −0.25724 |
| 202833_s_at | SERPINA1 | 576 | −0.20583 |
| 202935_s_at | SOX9 | 750 | −0.25574 |
| 203413_at | NELL2 | 629 | −0.23576 |
| 203881_s_at | DMD | 850 | −0.24341 |

TABLE 5-continued

Group of 80 genes for prognostic and diagnostic testing of lung cancer.

| Affymetrix ID | Gene symbol (HUGO ID) | Number of runs* | Signal to noise in a cancer sample** |
|---|---|---|---|
| 203908_at | SLC4A4 | 887 | −0.23167 |
| 204006_s_at | FCGR3A /// FCGR3B | 207 | −0.20071 |
| 204403_x_at | KIAA0738 | 923 | 0.167772 |
| 204427_s_at | RNP24 | 725 | −0.2366 |
| 206056_x_at | SPN | 976 | 0.196398 |
| 206169_x_at | RoXaN | 984 | 0.259637 |
| 207730_x_at | HDGF2 | 969 | 0.169108 |
| 207756_at | — | 855 | 0.161708 |
| 207791_s_at | RAB1A | 823 | −0.21704 |
| 207953_at | AD7C-NTP | 1000 | 0.218433 |
| 208137_x_at | — | 996 | 0.191938 |
| 208246_x_at | TK2 | 982 | 0.179058 |
| 208654_s_at | CD164 | 388 | −0.21228 |
| 208892_s_at | DUSP6 | 878 | −0.25023 |
| 209189_at | FOS | 935 | −0.27446 |
| 209204_at | LMO4 | 78 | 0.158674 |
| 209267_s_at | SLC39A8 | 228 | −0.24231 |
| 209369_at | ANXA3 | 384 | −0.19972 |
| 209656_s_at | TMEM47 | 456 | −0.23033 |
| 209774_x_at | CXCL2 | 404 | −0.2117 |
| 210145_at | PLA2G4A | 475 | −0.26146 |
| 210168_at | C6 | 458 | −0.24157 |
| 210317_s_at | YWHAE | 803 | −0.29542 |
| 210397_at | DEFB1 | 176 | −0.22512 |
| 210679_x_at | — | 970 | 0.181718 |
| 211506_s_at | IL8 | 270 | −0.3105 |
| 212006_at | UBXD2 | 802 | −0.22094 |
| 213089_at | LOC153561 | 649 | 0.164097 |
| 213736_at | COX5B | 505 | 0.155243 |
| 213813_x_at | — | 789 | 0.178643 |
| 214007_s_at | PTK9 | 480 | −0.21285 |
| 214146_s_at | PPBP | 593 | −0.24265 |
| 214594_x_at | ATP8B1 | 962 | 0.284039 |
| 214707_x_at | ALMS1 | 750 | 0.164047 |
| 214715_x_at | ZNF160 | 996 | 0.198532 |
| 215204_at | SENP6 | 211 | 0.169986 |
| 215208_x_at | RPL35A | 999 | 0.228485 |
| 215385_at | FTO | 164 | 0.187634 |
| 215600_x_at | FBXW12 | 960 | 0.17329 |
| 215604_x_at | UBE2D2 | 998 | 0.224878 |
| 215609_at | STARD7 | 940 | 0.191953 |
| 215628_x_at | PPP2CA | 829 | 0.16391 |
| 215800_at | DUOX1 | 412 | 0.160036 |
| 215907_at | BACH2 | 987 | 0.178338 |
| 215978_at | LOC152719 | 645 | 0.163399 |
| 216834_at | — | 633 | −0.25508 |
| 216858_x_at | — | 997 | 0.232969 |
| 217446_x_at | — | 942 | 0.182612 |
| 217653_x_at | — | 976 | 0.270552 |
| 217679_x_at | — | 987 | 0.265918 |
| 217715_x_at | ZNF354A | 995 | 0.223881 |
| 217826_s_at | UBE2J1 | 812 | −0.23003 |
| 218155_x_at | FLJ10534 | 998 | 0.186425 |
| 218976_at | DNAJC12 | 486 | −0.22866 |
| 219392_x_at | FLJ11029 | 867 | 0.169113 |
| 219678_x_at | DCLRE1C | 877 | 0.169975 |
| 220199_s_at | FLJ12806 | 378 | −0.20713 |
| 220389_at | FLJ23514 | 102 | 0.239341 |
| 220720_x_at | FLJ14346 | 989 | 0.17976 |
| 221191_at | DKFZP434A0131 | 616 | 0.185412 |
| 221310_at | FGF14 | 511 | −0.19965 |
| 221765_at | — | 319 | −0.25025 |
| 222027_at | NUCKS | 547 | 0.171954 |
| 222104_at | GTF2H3 | 981 | 0.186025 |
| 222358_x_at | — | 564 | 0.194048 |

TABLE 6

Group of 535 genes useful in prognosis or diagnosis of lung cancer.

| Affymetrix ID | Gene symbol (HUGO ID) | Number of runs* | Signal to noise in a cancer sample** |
|---|---|---|---|
| 200729_s_at | ACTR2 | 736 | −0.22284 |
| 200760_s_at | ARL6IP5 | 483 | −0.21221 |
| 201399_s_at | TRAM1 | 611 | −0.21328 |
| 201444_s_at | ATP6AP2 | 527 | −0.21487 |
| 201635_s_at | FXR1 | 458 | −0.2162 |
| 201689_s_at | TPD52 | 565 | −0.22292 |
| 201925_s_at | DAF | 717 | −0.25875 |
| 201926_s_at | DAF | 591 | −0.23228 |
| 201946_s_at | CCT2 | 954 | −0.24592 |
| 202118_s_at | CPNE3 | 334 | −0.21273 |
| 202704_at | TOB1 | 943 | −0.25724 |
| 202833_s_at | SERPINA1 | 576 | −0.20583 |
| 202935_s_at | SOX9 | 750 | −0.25574 |
| 203413_at | NELL2 | 629 | −0.23576 |
| 203881_s_at | DMD | 850 | −0.24341 |
| 203908_at | SLC4A4 | 887 | −0.23167 |
| 204006_s_at | FCGR3A /// FCGR3B | 207 | −0.20071 |
| 204403_x_at | KIAA0738 | 923 | 0.167772 |
| 204427_s_at | RNP24 | 725 | −0.2366 |
| 206056_x_at | SPN | 976 | 0.196398 |
| 206169_x_at | RoXaN | 984 | 0.259637 |
| 207730_x_at | HDGF2 | 969 | 0.169108 |
| 207756_at | — | 855 | 0.161708 |
| 207791_s_at | RAB1A | 823 | −0.21704 |
| 207953_at | AD7C-NTP | 1000 | 0.218433 |
| 208137_x_at | — | 996 | 0.191938 |
| 208246_x_at | TK2 | 982 | 0.179058 |
| 208654_s_at | CD164 | 388 | −0.21228 |
| 208892_s_at | DUSP6 | 878 | −0.25023 |
| 209189_at | FOS | 935 | −0.27446 |
| 209204_at | LMO4 | 78 | 0.158674 |
| 209267_s_at | SLC39A8 | 228 | −0.24231 |
| 209369_at | ANXA3 | 384 | −0.19972 |
| 209656_s_at | TMEM47 | 456 | −0.23033 |
| 209774_x_at | CXCL2 | 404 | −0.2117 |
| 210145_at | PLA2G4A | 475 | −0.26146 |
| 210168_at | C6 | 458 | −0.24157 |
| 210317_s_at | YWHAE | 803 | −0.29542 |
| 210397_at | DEFB1 | 176 | −0.22512 |
| 210679_x_at | — | 970 | 0.181718 |
| 211506_s_at | IL8 | 270 | −0.3105 |
| 212006_at | UBXD2 | 802 | −0.22094 |
| 213089_at | LOC153561 | 649 | 0.164097 |
| 213736_at | COX5B | 505 | 0.155243 |
| 213813_x_at | — | 789 | 0.178643 |
| 214007_s_at | PTK9 | 480 | −0.21285 |
| 214146_s_at | PPBP | 593 | −0.24265 |
| 214594_x_at | ATP8B1 | 962 | 0.284039 |
| 214707_x_at | ALMS1 | 750 | 0.164047 |
| 214715_x_at | ZNF160 | 996 | 0.198532 |
| 215204_at | SENP6 | 211 | 0.169986 |
| 215208_x_at | RPL35A | 999 | 0.228485 |
| 215385_at | FTO | 164 | 0.187634 |
| 215600_x_at | FBXW12 | 960 | 0.17329 |
| 215604_x_at | UBE2D2 | 998 | 0.224878 |
| 215609_at | STARD7 | 940 | 0.191953 |
| 215628_x_at | PPP2CA | 829 | 0.16391 |
| 215800_at | DUOX1 | 412 | 0.160036 |
| 215907_at | BACH2 | 987 | 0.178338 |
| 215978_at | LOC152719 | 645 | 0.163399 |
| 216834_at | — | 633 | −0.25508 |
| 216858_x_at | — | 997 | 0.232969 |
| 217446_x_at | — | 942 | 0.182612 |
| 217653_x_at | — | 976 | 0.270552 |
| 217679_x_at | — | 987 | 0.265918 |
| 217715_x_at | ZNF354A | 995 | 0.223881 |
| 217826_s_at | UBE2J1 | 812 | −0.23003 |
| 218155_x_at | FLJ10534 | 998 | 0.186425 |
| 218976_at | DNAJC12 | 486 | −0.22866 |
| 219392_x_at | FLJ11029 | 867 | 0.169113 |
| 219678_x_at | DCLRE1C | 877 | 0.169975 |
| 220199_s_at | FLJ12806 | 378 | −0.20713 |
| 220389_at | FLJ23514 | 102 | 0.239341 |

TABLE 6-continued

Group of 535 genes useful in prognosis or diagnosis of lung cancer.

| Affymetrix ID | Gene symbol (HUGO ID) | Number of runs* | Signal to noise in a cancer sample** |
|---|---|---|---|
| 220720_x_at | FLJ14346 | 989 | 0.17976 |
| 221191_at | DKFZP434A0131 | 616 | 0.185412 |
| 221310_at | FGF14 | 511 | −0.19965 |
| 221765_at | — | 319 | −0.25025 |
| 222027_at | NUCKS | 547 | 0.171954 |
| 222104_x_at | GTF2H3 | 981 | 0.186025 |
| 222358_x_at | — | 564 | 0.194048 |
| 202113_s_at | SNX2 | 841 | −0.20503 |
| 207133_x_at | ALPK1 | 781 | 0.155812 |
| 218989_at | SLC30A5 | 765 | −0.198 |
| 200751_s_at | HNRPC | 759 | −0.19243 |
| 220796_x_at | SLC35E1 | 691 | 0.158199 |
| 209362_at | SURB7 | 690 | −0.18777 |
| 216248_s_at | NR4A2 | 678 | −0.19796 |
| 203138_at | HAT1 | 669 | −0.18115 |
| 221428_s_at | TBL1XR1 | 665 | −0.19331 |
| 218172_s_at | DERL1 | 665 | −0.16341 |
| 215861_at | FLJ14031 | 651 | 0.156927 |
| 209288_s_at | CDC42EP3 | 638 | −0.20146 |
| 214001_x_at | RPS10 | 634 | 0.151006 |
| 209116_x_at | HBB | 626 | −0.12237 |
| 215595_at | GCNT2 | 625 | 0.136319 |
| 208891_at | DUSP6 | 617 | −0.17282 |
| 215067_x_at | PRDX2 | 616 | 0.160582 |
| 202918_s_at | PREI3 | 614 | −0.17003 |
| 211985_s_at | CALM1 | 614 | −0.20103 |
| 212019_at | RSL1D1 | 601 | 0.152717 |
| 216187_x_at | KNS2 | 591 | 0.14297 |
| 215066_at | PTPRF | 587 | 0.143323 |
| 212192_at | KCTD12 | 581 | −0.17535 |
| 217586_at | — | 577 | 0.147487 |
| 203582_s_at | RAB4A | 567 | −0.18289 |
| 220113_x_at | POLR1B | 563 | 0.15764 |
| 217232_x_at | HBB | 561 | −0.11398 |
| 201041_s_at | DUSP1 | 560 | −0.18661 |
| 211450_s_at | MSH6 | 544 | −0.15597 |
| 202648_at | RPS19 | 533 | 0.150087 |
| 202936_s_at | SOX9 | 533 | −0.17714 |
| 204426_at | RNP24 | 526 | −0.18959 |
| 206392_s_at | RARRES1 | 517 | −0.18328 |
| 208750_s_at | ARF1 | 515 | −0.19797 |
| 202089_s_at | SLC39A6 | 512 | −0.19904 |
| 211297_s_at | CDK7 | 510 | −0.15972 |
| 215373_x_at | FLJ12151 | 509 | 0.146742 |
| 213679_at | FLJ13946 | 492 | −0.10963 |
| 201694_s_at | EGR1 | 490 | −0.19478 |
| 209142_s_at | UBE2G1 | 487 | −0.18055 |
| 217706_at | LOC220074 | 483 | 0.11787 |
| 212991_at | FBXO9 | 476 | 0.148288 |
| 201289_at | CYR61 | 465 | −0.19925 |
| 206548_at | FLJ23556 | 465 | 0.141583 |
| 202593_s_at | MIR16 | 462 | −0.17042 |
| 202932_at | YES1 | 461 | −0.17637 |
| 220575_at | FLJ11800 | 461 | 0.116435 |
| 217713_x_at | DKFZP566N034 | 452 | 0.145994 |
| 211953_at | RANBP5 | 447 | −0.17838 |
| 203827_at | WIPI49 | 447 | −0.17767 |
| 221997_s_at | MRPL52 | 444 | 0.132649 |
| 217662_x_at | BCAP29 | 434 | 0.116886 |
| 218519_at | SLC35A5 | 428 | −0.15495 |
| 214833_at | KIAA0792 | 428 | 0.132943 |
| 201339_s_at | SCP2 | 426 | −0.18605 |
| 203799_at | CD302 | 422 | −0.16798 |
| 211090_s_at | PRPF4B | 421 | −0.1838 |
| 220071_x_at | C15orf25 | 420 | 0.138308 |
| 203946_s_at | ARG2 | 415 | −0.14964 |
| 213544_at | ING1L | 415 | 0.137052 |
| 209908_s_at | — | 414 | 0.131346 |
| 201688_s_at | TPD52 | 410 | −0.18965 |
| 215587_x_at | BTBD14B | 410 | 0.139952 |
| 201699_at | PSMC6 | 409 | −0.13784 |
| 214902_x_at | FLJ42393 | 409 | 0.140198 |
| 214041_x_at | RPL37A | 402 | 0.106746 |
| 203987_at | FZD6 | 392 | −0.19252 |
| 211696_x_at | HBB | 392 | −0.09508 |
| 218025_s_at | PECI | 389 | −0.18002 |
| 215852_x_at | KIAA0889 | 382 | 0.12243 |
| 209458_x_at | HBA1 /// HBA2 | 380 | −0.09796 |
| 219410_at | TMEM45A | 379 | −0.22387 |
| 215375_x_at | — | 379 | 0.148377 |
| 206302_s_at | NUDT4 | 376 | −0.18873 |
| 208783_s_at | MCP | 372 | −0.15076 |
| 211374_x_at | — | 364 | 0.131101 |
| 220352_x_at | MGC4278 | 364 | 0.152722 |
| 216609_at | TXN | 363 | 0.15162 |
| 201942_s_at | CPD | 363 | −0.1889 |
| 202672_s_at | ATF3 | 361 | −0.12935 |
| 204959_at | MNDA | 359 | −0.21676 |
| 211996_s_at | KIAA0220 | 358 | 0.144358 |
| 222035_s_at | PAPOLA | 353 | −0.14487 |
| 208808_s_at | HMGB2 | 349 | −0.15222 |
| 203711_s_at | HIBCH | 347 | −0.13214 |
| 215179_x_at | PGF | 347 | 0.146279 |
| 213562_s_at | SQLE | 345 | −0.14669 |
| 203765_at | GCA | 340 | −0.1798 |
| 214414_x_at | HBA2 | 336 | −0.08492 |
| 217497_at | ECGF1 | 336 | 0.123255 |
| 220924_s_at | SLC38A2 | 333 | −0.17315 |
| 218139_s_at | C14orf108 | 332 | −0.15021 |
| 201096_s_at | ARF4 | 330 | −0.18887 |
| 220361_at | FLJ12476 | 325 | −0.15452 |
| 202169_s_at | AASDHPPT | 323 | −0.15787 |
| 202527_s_at | SMAD4 | 322 | −0.18399 |
| 202166_s_at | PPP1R2 | 320 | −0.16402 |
| 204634_at | NEK4 | 319 | −0.15511 |
| 215504_x_at | — | 319 | 0.145981 |
| 202388_at | RGS2 | 315 | −0.14894 |
| 215553_x_at | WDR45 | 315 | 0.137586 |
| 200598_s_at | TRA1 | 314 | −0.19349 |
| 202435_s_at | CYP1B1 | 313 | 0.056937 |
| 216206_x_at | MAP2K7 | 313 | 0.10383 |
| 212582_at | OSBPL8 | 313 | −0.17843 |
| 216509_x_at | MLLT10 | 312 | 0.123961 |
| 200908_s_at | RPLP2 | 308 | 0.136645 |
| 215108_x_at | TNRC9 | 306 | −0.1439 |
| 213872_at | C6orf62 | 302 | −0.19548 |
| 214395_x_at | EEF1D | 302 | 0.128234 |
| 222156_x_at | CCPG1 | 301 | −0.14725 |
| 201426_s_at | VIM | 301 | −0.17461 |
| 221972_s_at | Cab45 | 299 | −0.1511 |
| 219957_at | — | 298 | 0.130796 |
| 215123_at | — | 295 | 0.125434 |
| 212515_s_at | DDX3X | 295 | −0.14634 |
| 203357_s_at | CAPN7 | 295 | −0.17109 |
| 211711_s_at | PTEN | 295 | −0.12636 |
| 206165_s_at | CLCA2 | 293 | −0.17699 |
| 213959_s_at | KIAA1005 | 289 | −0.16592 |
| 215083_at | PSPC1 | 289 | 0.147348 |
| 219630_at | PDZK1IP1 | 287 | −0.15086 |
| 204018_x_at | HBA1 /// HBA2 | 286 | −0.08689 |
| 208671_at | TDE2 | 286 | −0.17839 |
| 203427_at | ASF1A | 286 | −0.14737 |
| 215281_x_at | POGZ | 286 | 0.142825 |
| 205749_at | CYP1A1 | 285 | 0.107118 |
| 212585_at | OSBPL8 | 282 | −0.13924 |
| 211745_x_at | HBA1 /// HBA2 | 281 | −0.08437 |
| 208078_s_at | SNF1LK | 278 | −0.14395 |
| 218041_x_at | SLC38A2 | 276 | −0.17003 |
| 212588_at | PTPRC | 270 | −0.1725 |
| 212397_at | RDX | 270 | −0.15613 |
| 208268_at | ADAM28 | 269 | 0.114996 |
| 207194_s_at | ICAM4 | 269 | 0.127304 |
| 222252_x_at | — | 269 | 0.132241 |
| 217414_x_at | HBA2 | 266 | −0.08974 |
| 207078_at | MED6 | 261 | 0.1232 |
| 215268_at | KIAA0754 | 261 | 0.13669 |

TABLE 6-continued

Group of 535 genes useful in prognosis or diagnosis of lung cancer.

| Affymetrix ID | Gene symbol (HUGO ID) | Number of runs* | Signal to noise in a cancer sample** |
|---|---|---|---|
| 221387_at | GPR147 | 261 | 0.128737 |
| 201337_s_at | VAMP3 | 259 | −0.17284 |
| 220218_at | C9orf68 | 259 | 0.125851 |
| 222356_at | TBL1Y | 259 | 0.126765 |
| 208579_x_at | H2BFS | 258 | −0.16608 |
| 219161_s_at | CKLF | 257 | −0.12288 |
| 202917_s_at | S100A8 | 256 | −0.19869 |
| 204455_at | DST | 255 | −0.13072 |
| 211672_s_at | ARPC4 | 254 | −0.17791 |
| 201132_at | HNRPH2 | 254 | −0.12817 |
| 218313_s_at | GALNT7 | 253 | −0.179 |
| 218930_s_at | FLJ11273 | 251 | −0.15878 |
| 219166_at | C14orf104 | 250 | −0.14237 |
| 212805_at | KIAA0367 | 248 | −0.16649 |
| 201551_s_at | LAMP1 | 247 | −0.18035 |
| 202599_s_at | NRIP1 | 247 | −0.16226 |
| 203403_s_at | RNF6 | 247 | −0.14976 |
| 214261_at | ADH6 | 242 | −0.1414 |
| 202033_s_at | RB1CC1 | 240 | −0.18105 |
| 203896_s_at | PLCB4 | 237 | −0.20318 |
| 209703_x_at | DKFZP586A0522 | 234 | 0.140153 |
| 211699_x_at | HBA1 /// HBA2 | 232 | −0.08369 |
| 210764_s_at | CYR61 | 231 | −0.13139 |
| 206391_at | RARRES1 | 230 | −0.16931 |
| 201312_s_at | SH3BGRL | 225 | −0.12265 |
| 200798_x_at | MCL1 | 221 | −0.13113 |
| 214912_at | — | 221 | 0.116262 |
| 204621_at | NR4A2 | 217 | −0.10896 |
| 217761_at | MTCBP-1 | 217 | −0.17558 |
| 205830_at | CLGN | 216 | −0.14737 |
| 218438_s_at | MED28 | 214 | −0.14649 |
| 207475_at | FABP2 | 214 | 0.097003 |
| 208621_s_at | VIL2 | 213 | −0.19678 |
| 202436_s_at | CYP1B1 | 212 | 0.042216 |
| 202539_s_at | HMGCR | 210 | −0.15429 |
| 210830_s_at | PON2 | 209 | −0.17184 |
| 211906_s_at | SERPINB4 | 207 | −0.14728 |
| 202241_at | TRIB1 | 207 | −0.10706 |
| 203594_at | RTCD1 | 207 | −0.13823 |
| 215863_at | TFR2 | 207 | 0.095157 |
| 221992_at | LOC283970 | 206 | 0.126744 |
| 221872_at | RARRES1 | 205 | −0.11496 |
| 219564_at | KCNJ16 | 205 | −0.13908 |
| 201329_s_at | ETS2 | 205 | −0.14994 |
| 214188_at | HIS1 | 203 | 0.1257 |
| 201667_at | GJA1 | 199 | −0.13848 |
| 201464_x_at | JUN | 199 | −0.09858 |
| 215409_at | LOC254531 | 197 | 0.094182 |
| 202583_s_at | RANBP9 | 197 | −0.13902 |
| 215594_at | — | 197 | 0.101007 |
| 214326_x_at | JUND | 196 | −0.1702 |
| 217140_s_at | VDAC1 | 196 | −0.14682 |
| 215599_at | SMA4 | 195 | 0.133438 |
| 209896_s_at | PTPN11 | 195 | −0.16258 |
| 204846_at | CP | 195 | −0.14378 |
| 222303_at | — | 193 | −0.10841 |
| 218218_at | DIP13B | 193 | −0.12136 |
| 211015_s_at | HSPA4 | 192 | −0.13489 |
| 208666_s_at | ST13 | 191 | −0.13361 |
| 203191_at | ABCB6 | 190 | 0.096808 |
| 202731_at | PDCD4 | 190 | −0.1545 |
| 209027_s_at | ABI1 | 190 | −0.15472 |
| 205979_at | SCGB2A1 | 189 | −0.15091 |
| 216351_x_at | DAZ1 /// DAZ2 /// DAZ3 /// DAZ4 | 189 | 0.106368 |
| 220240_s_at | C13orf11 | 188 | −0.16959 |
| 204482_at | CLDN5 | 187 | 0.094134 |
| 217234_s_at | VIL2 | 186 | −0.16035 |
| 214350_at | SNTB2 | 186 | 0.095723 |
| 201693_s_at | EGR1 | 184 | −0.10732 |
| 212328_at | KIAA1102 | 182 | −0.12113 |
| 220168_at | CASC1 | 181 | −0.1105 |
| 203628_at | IGF1R | 180 | 0.067575 |
| 204622_x_at | NR4A2 | 180 | −0.11482 |
| 213246_at | C14orf109 | 180 | −0.16143 |
| 218728_s_at | HSPC163 | 180 | −0.13248 |
| 214753_at | PFAAP5 | 179 | 0.130184 |
| 206336_at | CXCL6 | 178 | −0.05634 |
| 201445_at | CNN3 | 178 | −0.12375 |
| 209886_s_at | SMAD6 | 176 | 0.079296 |
| 213376_at | ZBTB1 | 176 | −0.17777 |
| 213887_s_at | POLR2E | 175 | −0.16392 |
| 204783_at | MLF1 | 174 | −0.13409 |
| 218824_at | FLJ10781 | 173 | 0.1394 |
| 212417_at | SCAMP1 | 173 | −0.17052 |
| 202437_s_at | CYP1B1 | 171 | 0.033438 |
| 217528_at | CLCA2 | 169 | −0.14179 |
| 218170_at | ISOC1 | 169 | −0.14064 |
| 206278_at | PTAFR | 167 | 0.087096 |
| 201939_at | PLK2 | 167 | −0.11049 |
| 200907_s_at | KIAA0992 | 166 | −0.18323 |
| 207480_s_at | MEIS2 | 166 | −0.15232 |
| 201417_at | SOX4 | 162 | −0.09617 |
| 213826_s_at | — | 160 | 0.097313 |
| 214953_s_at | APP | 159 | −0.1645 |
| 204897_at | PTGER4 | 159 | −0.08152 |
| 201711_x_at | RANBP2 | 158 | −0.17192 |
| 202457_s_at | PPP3CA | 158 | −0.18821 |
| 206683_at | ZNF165 | 158 | −0.08848 |
| 214581_x_at | TNFRSF21 | 156 | −0.14624 |
| 203392_s_at | CTBP1 | 155 | −0.16161 |
| 212720_at | PAPOLA | 155 | −0.14809 |
| 207758_at | PPM1F | 155 | 0.090007 |
| 220995_at | STXBP6 | 155 | 0.106749 |
| 213831_at | HLA-DQA1 | 154 | 0.193368 |
| 212044_s_at | — | 153 | 0.098889 |
| 202434_s_at | CYP1B1 | 153 | 0.049744 |
| 206166_s_at | CLCA2 | 153 | −0.1343 |
| 218343_s_at | GTF3C3 | 153 | −0.13066 |
| 202557_at | STCH | 152 | −0.14894 |
| 201133_s_at | PJA2 | 152 | −0.18481 |
| 213605_s_at | MGC22265 | 151 | 0.130895 |
| 210947_s_at | MSH3 | 151 | −0.12595 |
| 208310_s_at | C7orf28A /// C7orf28B | 151 | −0.15523 |
| 209307_at | — | 150 | −0.1667 |
| 215387_x_at | GPC6 | 148 | 0.114691 |
| 213705_at | MAT2A | 147 | 0.104855 |
| 213979_s_at | — | 146 | 0.121562 |
| 212731_at | LOC157567 | 146 | −0.1214 |
| 210117_at | SPAG1 | 146 | −0.11236 |
| 200641_s_at | YWHAZ | 145 | −0.14071 |
| 210701_at | CFDP1 | 145 | 0.151664 |
| 217152_at | NCOR1 | 145 | 0.130891 |
| 204224_s_at | GCH1 | 144 | −0.14574 |
| 202028_s_at | — | 144 | 0.094276 |
| 201735_s_at | CLCN3 | 144 | −0.1434 |
| 208447_s_at | PRPS1 | 143 | −0.14933 |
| 220926_s_at | C1orf22 | 142 | −0.17477 |
| 211505_s_at | STAU | 142 | −0.11618 |
| 221684_s_at | NYX | 142 | 0.102298 |
| 206906_at | ICAM5 | 141 | 0.076813 |
| 213228_at | PDE8B | 140 | −0.13728 |
| 217202_s_at | GLUL | 139 | −0.15489 |
| 211713_x_at | KIAA0101 | 138 | 0.108672 |
| 215012_at | ZNF451 | 138 | 0.13269 |
| 200806_s_at | HSPD1 | 137 | −0.14811 |
| 201466_s_at | JUN | 135 | −0.0667 |
| 211564_s_at | PDLIM4 | 134 | −0.12756 |
| 207850_at | CXCL3 | 133 | −0.17973 |
| 221841_s_at | KLF4 | 133 | −0.1415 |
| 200605_s_at | PRKAR1A | 132 | −0.15642 |
| 221198_at | SCT | 132 | 0.08221 |
| 201772_at | AZIN1 | 131 | −0.16639 |
| 205009_at | TFF1 | 130 | −0.17578 |
| 205542_at | STEAP1 | 129 | −0.08498 |
| 218195_at | C6orf211 | 129 | −0.14497 |

TABLE 6-continued

Group of 535 genes useful in prognosis or diagnosis of lung cancer.

| Affymetrix ID | Gene symbol (HUGO ID) | Number of runs* | Signal to noise in a cancer sample** |
|---|---|---|---|
| 213642_at | — | 128 | 0.079657 |
| 212891_s_at | GADD45GIP1 | 128 | −0.09272 |
| 202798_at | SEC24B | 127 | −0.12621 |
| 222207_x_at | — | 127 | 0.10783 |
| 202638_s_at | ICAM1 | 126 | 0.070364 |
| 200730_s_at | PTP4A1 | 126 | −0.15289 |
| 219355_at | FLJ10178 | 126 | −0.13407 |
| 220266_s_at | KLF4 | 126 | −0.15324 |
| 201259_s_at | SYPL | 124 | −0.16643 |
| 209649_at | STAM2 | 124 | −0.1696 |
| 220094_s_at | C6orf79 | 123 | −0.12214 |
| 221751_at | PANK3 | 123 | −0.1723 |
| 200008_s_at | GDI2 | 123 | −0.15852 |
| 205078_at | PIGF | 121 | −0.13747 |
| 218842_at | FLJ21908 | 121 | −0.08903 |
| 202536_at | CHMP2B | 121 | −0.14745 |
| 220184_at | NANOG | 119 | 0.098142 |
| 201117_at | CPE | 118 | −0.20025 |
| 219787_s_at | ECT2 | 117 | −0.14278 |
| 206628_at | SLC5A1 | 117 | −0.12838 |
| 204007_at | FCGR3B | 116 | −0.15337 |
| 209446_s_at | — | 116 | 0.100508 |
| 211612_s_at | IL13RA1 | 115 | −0.17266 |
| 220992_s_at | C1orf25 | 115 | −0.11026 |
| 221899_at | PFAAP5 | 115 | 0.11698 |
| 221719_s_at | LZTS1 | 115 | 0.093494 |
| 201473_at | JUNB | 114 | −0.10249 |
| 221193_s_at | ZCCHC10 | 112 | −0.08003 |
| 215659_at | GSDML | 112 | 0.118288 |
| 205157_s_at | KRT17 | 111 | −0.14232 |
| 201001_s_at | UBE2V1 /// Kua-UEV | 111 | −0.16786 |
| 216789_at | — | 111 | 0.105386 |
| 205506_at | VIL1 | 111 | 0.097452 |
| 204875_s_at | GMDS | 110 | −0.12995 |
| 207191_s_at | ISLR | 110 | 0.100627 |
| 202779_s_at | UBE2S | 109 | −0.11364 |
| 210370_s_at | LY9 | 109 | 0.096323 |
| 202842_s_at | DNAJB9 | 108 | −0.15326 |
| 201082_s_at | DCTN1 | 107 | −0.10104 |
| 215588_x_at | RIOK3 | 107 | 0.135837 |
| 211076_x_at | DRPLA | 107 | 0.102743 |
| 210230_at | — | 106 | 0.115001 |
| 206544_s_at | SMARCA2 | 106 | −0.12099 |
| 208852_s_at | CANX | 105 | −0.14776 |
| 215405_at | MYO1E | 105 | 0.086393 |
| 208653_s_at | CD164 | 104 | −0.09185 |
| 206355_at | GNAL | 103 | 0.1027 |
| 210793_s_at | NUP98 | 103 | −0.13244 |
| 215070_x_at | RABGAP1 | 103 | 0.125029 |
| 203007_x_at | LYPLA1 | 102 | −0.17961 |
| 203841_x_at | MAPRE3 | 102 | −0.13389 |
| 206759_at | FCER2 | 102 | 0.081733 |
| 202232_s_at | GA17 | 102 | −0.11373 |
| 215892_at | — | 102 | 0.13866 |
| 214359_s_at | HSPCB | 101 | −0.12276 |
| 215810_x_at | DST | 101 | 0.098963 |
| 208937_s_at | ID1 | 100 | −0.06552 |
| 213664_at | SLC1A1 | 100 | −0.12654 |
| 219338_s_at | FLJ20156 | 100 | −0.10332 |
| 206595_at | CST6 | 99 | −0.10059 |
| 207300_s_at | F7 | 99 | 0.082445 |
| 213792_s_at | INSR | 98 | 0.137962 |
| 209674_at | CRY1 | 98 | −0.13818 |
| 40665_at | FMO3 | 97 | −0.05976 |
| 217975_at | WBP5 | 97 | −0.12698 |
| 210296_s_at | PXMP3 | 97 | −0.13537 |
| 215483_at | AKAP9 | 95 | 0.125966 |
| 212633_at | KIAA0776 | 95 | −0.16793 |
| 206164_at | CLCA2 | 94 | −0.13117 |
| 216813_at | — | 94 | 0.089023 |
| 208925_at | C3orf4 | 94 | −0.1721 |
| 219469_at | DNCH2 | 94 | −0.12003 |
| 206016_at | CXorf37 | 93 | −0.11569 |
| 216745_x_at | LRCH1 | 93 | 0.117149 |
| 212999_x_at | HLA-DQB1 | 92 | 0.110258 |
| 216859_x_at | — | 92 | 0.116351 |
| 201636_at | — | 92 | −0.13501 |
| 204272_at | LGALS4 | 92 | 0.110391 |
| 215454_x_at | SFTPC | 91 | 0.064918 |
| 215972_at | — | 91 | 0.097654 |
| 220593_s_at | FLJ20753 | 91 | 0.095702 |
| 222009_at | CGI-14 | 91 | 0.070949 |
| 207115_x_at | MBTD1 | 91 | 0.107883 |
| 216922_x_at | DAZ1 /// DAZ3 /// DAZ2 /// DAZ4 | 91 | 0.086888 |
| 217626_at | AKR1C1 /// AKR1C2 | 90 | 0.036545 |
| 211429_s_at | SERPINA1 | 90 | −0.11406 |
| 209662_at | CETN3 | 90 | −0.10879 |
| 201629_s_at | ACP1 | 90 | −0.14441 |
| 201236_s_at | BTG2 | 89 | −0.09435 |
| 217137_x_at | — | 89 | 0.070954 |
| 212476_at | CENTB2 | 89 | −0.1077 |
| 218545_at | FLJ11088 | 89 | −0.12452 |
| 208857_s_at | PCMT1 | 89 | −0.14704 |
| 221931_s_at | SEH1L | 88 | −0.11491 |
| 215046_at | FLJ23861 | 88 | −0.14667 |
| 220222_at | PRO1905 | 88 | 0.081524 |
| 209737_at | AIP1 | 87 | −0.07696 |
| 203904_at | MPO | 87 | 0.113275 |
| 219290_x_at | DAPP1 | 87 | 0.111366 |
| 205116_at | LAMA2 | 86 | 0.05845 |
| 222316_at | VDP | 86 | 0.091505 |
| 203574_at | NFIL3 | 86 | −0.14335 |
| 207820_at | ADH1A | 86 | 0.104444 |
| 203751_x_at | JUND | 85 | −0.14118 |
| 202930_s_at | SUCLA2 | 85 | −0.14884 |
| 215404_x_at | FGFR1 | 85 | 0.119684 |
| 216266_s_at | ARFGEF1 | 85 | −0.12432 |
| 212806_at | KIAA0367 | 85 | −0.13259 |
| 219253_at | — | 83 | −0.14094 |
| 214605_x_at | GPR1 | 83 | 0.114443 |
| 205403_at | IL1R2 | 82 | −0.19721 |
| 222282_at | PAPD4 | 82 | 0.128004 |
| 214129_at | PDE4DIP | 82 | −0.13913 |
| 209259_s_at | CSPG6 | 82 | −0.12618 |
| 216900_s_at | CHRNA4 | 82 | 0.105518 |
| 221943_x_at | RPL38 | 80 | 0.086719 |
| 215386_at | AUTS2 | 80 | 0.129921 |
| 201990_s_at | CREBL2 | 80 | −0.13645 |
| 220145_at | FLJ21159 | 79 | −0.16097 |
| 221173_at | USH1C | 79 | 0.109348 |
| 214900_at | ZKSCAN1 | 79 | 0.075517 |
| 203290_at | HLA-DQA1 | 78 | −0.20756 |
| 215382_x_at | TPSAB1 | 78 | −0.09041 |
| 201631_s_at | IER3 | 78 | −0.12038 |
| 212188_at | KCTD12 | 77 | −0.14672 |
| 220428_at | CD207 | 77 | 0.101238 |
| 215349_at | — | 77 | 0.10172 |
| 213928_s_at | HRB | 77 | 0.092136 |
| 221228_s_at | — | 77 | 0.0859 |
| 202069_s_at | IDH3A | 76 | −0.14747 |
| 208554_at | POU4F3 | 76 | 0.107529 |
| 209504_s_at | PLEKHB1 | 76 | −0.13125 |
| 212989_at | TMEM23 | 75 | −0.11012 |
| 216197_at | ATF7IP | 75 | 0.115016 |
| 204748_at | PTGS2 | 74 | −0.15194 |
| 205221_at | HGD | 74 | 0.096171 |
| 214705_at | INADL | 74 | 0.102919 |
| 213939_s_at | RIPX | 74 | 0.091175 |
| 203691_at | PI3 | 73 | −0.14375 |
| 220532_s_at | LR8 | 73 | −0.11432 |
| 209829_at | C6orf32 | 73 | −0.08982 |
| 206515_at | CYP4F3 | 72 | 0.104171 |
| 218541_s_at | C8orf4 | 72 | −0.09551 |
| 210732_s_at | LGALS8 | 72 | −0.13683 |
| 202643_s_at | TNFAIP3 | 72 | −0.16699 |

TABLE 6-continued

Group of 535 genes useful in prognosis or diagnosis of lung cancer.

| Affymetrix ID | Gene symbol (HUGO ID) | Number of runs* | Signal to noise in a cancer sample** |
|---|---|---|---|
| 218963_s_at | KRT23 | 72 | −0.10915 |
| 213304_at | KIAA0423 | 72 | −0.12256 |
| 202768_at | FOSB | 71 | −0.06289 |
| 205623_at | ALDH3A1 | 71 | 0.045457 |
| 206488_s_at | CD36 | 71 | −0.15899 |
| 204319_s_at | RGS10 | 71 | −0.10107 |
| 217811_at | SELT | 71 | −0.16162 |
| 202746_at | ITM2A | 70 | −0.06424 |
| 221127_s_at | RIG | 70 | 0.110593 |
| 209821_at | C9orf26 | 70 | −0.07383 |
| 220957_at | CTAGE1 | 70 | 0.092986 |
| 215577_at | UBE2E1 | 70 | 0.10305 |
| 214731_at | DKFZp547A023 | 70 | 0.102821 |
| 210512_s_at | VEGF | 69 | −0.11804 |
| 205267_at | POU2AF1 | 69 | 0.101353 |
| 216202_s_at | SPTLC2 | 69 | −0.11908 |
| 220477_s_at | C20orf30 | 69 | −0.16221 |
| 205863_at | S100A12 | 68 | −0.10353 |
| 215780_s_at | SET /// LOC389168 | 68 | −0.10381 |
| 218197_s_at | OXR1 | 68 | −0.14424 |
| 203077_s_at | SMAD2 | 68 | −0.11242 |
| 222339_x_at | — | 68 | 0.121585 |
| 200698_at | KDELR2 | 68 | −0.15907 |
| 210540_s_at | B4GALT4 | 67 | −0.13556 |
| 217725_x_at | PAI-RBP1 | 67 | −0.14956 |
| 217082_at | — | 67 | 0.086098 |

TABLE 7

Group of 20 genes useful in prognosis and/or diagnosis of lung cancer.

| Affymetrix ID | Gene symbol HUGO ID | Number of runs* | Signal to noise in a cancer sample* |
|---|---|---|---|
| 207953_at | AD7C-NTP | 1000 | 0.218433 |
| 215208_x_at | RPL35A | 999 | 0.228485 |
| 215604_x_at | UBE2D2 | 998 | 0.224878 |
| 218155_x_at | FLJ10534 | 998 | 0.186425 |
| 216858_x_at | — | 997 | 0.232969 |
| 208137_x_at | — | 996 | 0.191938 |
| 214715_x_at | ZNF160 | 996 | 0.198532 |
| 217715_x_at | ZNF354A | 995 | 0.223881 |
| 220720_x_at | FLJ14346 | 989 | 0.17976 |
| 215907_at | BACH2 | 987 | 0.178338 |
| 217679_x_at | — | 987 | 0.265918 |
| 206169_x_at | RoXaN | 984 | 0.259637 |
| 208246_x_at | TK2 | 982 | 0.179058 |
| 222104_x_at | GTF2H3 | 981 | 0.186025 |
| 206056_x_at | SPN | 976 | 0.196398 |
| 217653_x_at | — | 976 | 0.270552 |
| 210679_x_at | — | 970 | 0.181718 |
| 207730_x_at | HDGF2 | 969 | 0.169108 |
| 214594_x_at | ATP8B1 | 962 | 0.284039 |

*The number of runs when the gene is indicated in cancer samples as differentially expressed out of 1000 test runs.
** Negative values indicate increase of expression in lung cancer, positive values indicate decrease of expression in lung cancer.

One can use the above tables to correlate or compare the expression of the transcript to the expression of the gene product, i.e. protein. Increased expression of the transcript as shown in the table corresponds to increased expression of the gene product. Similarly, decreased expression of the transcript as shown in the table corresponds to decreased expression of the gene product.

In one preferred embodiment, one uses at least one, preferably at least 2, 3, 4, 5, 6, 7, 8, 9, 10 or more, of the genes as listed in Tables 8, 9 and/or 10. In one embodiment, one uses maximum of 500, 400, 300, 200, 100, or 50 of the gene that include at least 5, 6, 7, 8, 9, 10-20, 20-30, 30-40, 40-50, 50-60, 60-70, 1-70, of the genes listed in Tables 8-10.

TABLE 8

361 Airway t-test gene list

| AffyID | GeneName (HUGO ID) |
|---|---|
| 202437_s_at | CYP1B1 |
| 206561_s_at | AKR1B10 |
| 202436_s_at | CYP1B1 |
| 205749_at | CYP1A1 |
| 202435_s_at | CYP1B1 |
| 201884_at | CEACAM5 |
| 205623_at | ALDH3A1 |
| 217626_at | — |
| 209921_at | SLC7A11 |
| 209699_x_at | AKR1C2 |
| 201467_s_at | NQO1 |
| 201468_s_at | NQO1 |
| 202831_at | GPX2 |
| 214303_x_at | MUC5AC |
| 211653_x_at | AKR1C2 |
| 214385_s_at | MUC5AC |
| 216594_x_at | AKR1C1 |
| 205328_at | CLDN10 |
| 209160_at | AKR1C3 |
| 210519_s_at | NQO1 |
| 217678_at | SLC7A11 |
| 205221_at | HGD /// LOC642252 |
| 204151_x_at | AKR1C1 |
| 207469_s_at | PIR |
| 206153_at | CYP4F11 |
| 205513_at | TCN1 |
| 209386_at | TM4SF1 |
| 209351_at | KRT14 |
| 204059_s_at | ME1 |
| 209213_at | CBR1 |
| 210505_at | ADH7 |
| 214404_x_at | SPDEF |
| 204058_at | ME1 |
| 218002_s_at | CXCL14 |
| 205499_at | SRPX2 |
| 210065_s_at | UPK1B |
| 204341_at | TRIM16 /// TRIM16L /// LOC653524 |
| 221841_s_at | KLF4 |
| 208864_s_at | TXN |
| 208699_x_at | TKT |
| 210397_at | DEFB1 |
| 204971_at | CSTA |
| 211657_at | CEACAM6 |
| 201463_s_at | TALDO1 |
| 214164_x_at | CA12 |
| 203925_at | GCLM |
| 201118_at | PGD |
| 201266_at | TXNRD1 |
| 203757_s_at | CEACAM6 |
| 202923_s_at | GCLC |
| 214858_at | GPC1 |
| 205009_at | TFF1 |
| 219928_s_at | CABYR |
| 203963_at | CA12 |
| 210064_s_at | UPK1B |
| 219956_at | GALNT6 |
| 208700_s_at | TKT |
| 203824_at | TSPAN8 |
| 207126_x_at | UGT1A10 /// UGT1A8 /// UGT1A7 /// UGT1A6 /// UGT1A |
| 213441_x_at | SPDEF |
| 207430_s_at | MSMB |
| 209369_at | ANXA3 |
| 217187_at | MUC5AC |
| 209101_at | CTGF |
| 212221_x_at | IDS |
| 215867_x_at | CA12 |
| 214211_at | FTH1 |
| 217755_at | HN1 |
| 201431_s_at | DPYSL3 |
| 204875_s_at | GMDS |
| 215125_s_at | UGT1A10 /// UGT1A8 /// UGT1A7 /// UGT1A6 /// |

TABLE 8-continued

361 Airway t-test gene list

| AffyID | GeneName (HUGO ID) |
|---|---|
| | UGT1A |
| 63825_at | ABHD2 |
| 202922_at | GCLC |
| 218313_s_at | GALNT7 |
| 210297_s_at | MSMB |
| 209448_at | HTATIP2 |
| 204532_x_at | UGT1A10 /// UGT1A8 /// UGT1A7 /// UGT1A6 /// UGT1A |
| 200872_at | S100A10 |
| 216351_x_at | DAZ1 /// DAZ3 /// DAZ2 /// DAZ4 |
| 212223_at | IDS |
| 208680_at | PRDX1 |
| 206515_at | CYP4F3 |
| 208596_s_at | UGT1A10 /// UGT1A8 /// UGT1A7 /// UGT1A6 /// UGT1A |
| 209173_at | AGR2 |
| 204351_at | S100P |
| 202785_at | NDUFA7 |
| 204970_s_at | MAFG |
| 222016_s_at | ZNF323 |
| 200615_s_at | AP2B1 |
| 206094_x_at | UGT1A6 |
| 209706_at | NKX3-1 |
| 217977_at | SEPX1 |
| 201487_at | CTSC |
| 219508_at | GCNT3 |
| 204237_at | GULP1 |
| 213455_at | LOC283677 |
| 213624_at | SMPDL3A |
| 206770_s_at | SLC35A3 |
| 217975_at | WBP5 |
| 201263_at | TARS |
| 218696_at | EIF2AK3 |
| 212560_at | C11orf32 |
| 218885_s_at | GALNT12 |
| 212326_at | VPS13D |
| 217955_at | BCL2L13 |
| 203126_at | IMPA2 |
| 214106_s_at | GMDS |
| 209309_at | AZGP1 |
| 205112_at | PLCE1 |
| 215363_x_at | FOLH1 |
| 206302_s_at | NUDT4 /// NUDT4P1 |
| 200916_at | TAGLN2 |
| 205042_at | GNE |
| 217979_at | TSPAN13 |
| 203397_s_at | GALNT3 |
| 209786_at | HMGN4 |
| 211733_x_at | SCP2 |
| 207222_at | PLA2G10 |
| 204235_s_at | GULP1 |
| 205726_at | DIAPH2 |
| 203911_at | RAP1GAP |
| 200748_s_at | FTH1 |
| 212449_at | LYPLA1 |
| 213059_at | CREB3L1 |
| 201272_at | AKR1B1 |
| 208731_at | RAB2 |
| 205979_at | SCGB2A1 |
| 212805_at | KIAA0367 |
| 202804_at | ABCC1 |
| 218095_s_at | TPARL |
| 205566_at | ABHD2 |
| 209114_at | TSPAN1 |
| 202481_at | DHRS3 |
| 202805_s_at | ABCC1 |
| 219117_s_at | FKBP11 |
| 213172_at | TTC9 |
| 202554_s_at | GSTM3 |
| 218677_at | S100A14 |
| 203306_s_at | SLC35A1 |
| 204076_at | ENTPD4 |
| 200654_at | P4HB |
| 204500_s_at | AGTPBP1 |
| 208918_s_at | NADK |
| 221485_at | B4GALT5 |

TABLE 8-continued

361 Airway t-test gene list

| AffyID | GeneName (HUGO ID) |
|---|---|
| 221511_x_at | CCPG1 |
| 200733_s_at | PTP4A1 |
| 217901_at | DSG2 |
| 202769_at | CCNG2 |
| 202119_s_at | CPNE3 |
| 200945_s_at | SEC31L1 |
| 200924_s_at | SLC3A2 |
| 208736_at | ARPC3 |
| 221556_at | CDC14B |
| 221041_s_at | SLC17A5 |
| 215071_s_at | HIST1H2AC |
| 209682_at | CBLB |
| 209806_at | HIST1H2BK |
| 204485_s_at | TOM1L1 |
| 201666_at | TIMP1 |
| 203192_at | ABCB6 |
| 202722_s_at | GFPT1 |
| 213135_at | TIAM1 |
| 203509_at | SORL1 |
| 214620_x_at | PAM |
| 208919_s_at | NADK |
| 212724_at | RND3 |
| 212160_at | XPOT |
| 212812_at | SERINC5 |
| 200696_s_at | GSN |
| 217845_x_at | HIGD1A |
| 208612_at | PDIA3 |
| 219288_at | C3orf14 |
| 201923_at | PRDX4 |
| 211960_s_at | RAB7 |
| 64942_at | GPR153 |
| 201659_s_at | ARL1 |
| 202439_s_at | IDS |
| 209249_s_at | GHITM |
| 218723_s_at | RGC32 |
| 200087_s_at | TMED2 |
| 209694_at | PTS |
| 202320_at | GTF3C1 |
| 201193_at | IDH1 |
| 212233_at | — |
| 213891_s_at | — |
| 203041_s_at | LAMP2 |
| 202666_s_at | ACTL6A |
| 200863_s_at | RAB11A |
| 203663_s_at | COX5A |
| 211404_s_at | APLP2 |
| 201745_at | PTK9 |
| 217823_s_at | UBE2J1 |
| 202286_s_at | TACSTD2 |
| 212296_at | PSMD14 |
| 211048_s_at | PDIA4 |
| 214429_at | MTMR6 |
| 219429_at | FA2H |
| 212181_s_at | NUDT4 |
| 222116_s_at | TBC1D16 |
| 221689_s_at | PIGP |
| 209479_at | CCDC28A |
| 218434_s_at | AACS |
| 214665_s_at | CHP |
| 202085_at | TJP2 |
| 217992_s_at | EFHD2 |
| 203162_s_at | KATNB1 |
| 205406_s_at | SPA17 |
| 203476_at | TPBG |
| 201724_s_at | GALNT1 |
| 200599_s_at | HSP90B1 |
| 200929_at | TMED10 |
| 200642_at | SOD1 |
| 208946_s_at | BECN1 |
| 202562_s_at | C14orf1 |
| 201098_at | COPB2 |
| 221253_s_at | TXNDC5 |
| 201004_at | SSR4 |
| 203221_at | TLE1 |
| 201588_at | TXNL1 |
| 218684_at | LRRC8D |

TABLE 8-continued

361 Airway t-test gene list

| AffyID | GeneName (HUGO ID) |
|---|---|
| 208799_at | PSMB5 |
| 201471_s_at | SQSTM1 |
| 204034_at | ETHE1 |
| 208689_s_at | RPN2 |
| 212665_at | TIPARP |
| 200625_s_at | CAP1 |
| 213220_at | LOC92482 |
| 200709_at | FKBP1A |
| 203279_at | EDEM1 |
| 200068_s_at | CANX |
| 200620_at | TMEM59 |
| 200075_s_at | GUK1 |
| 209679_s_at | LOC57228 |
| 210715_s_at | SPINT2 |
| 209020_at | C20orf11 |
| 208091_s_at | ECOP |
| 200048_s_at | JTB |
| 218194_at | REXO2 |
| 209103_s_at | UFD1L |
| 208718_at | DDX17 |
| 219241_x_at | SSH3 |
| 216210_x_at | TRIOBP |
| 50277_at | GGA1 |
| 218023_s_at | FAM53C |
| 32540_at | PPP3CC |
| 43511_s_at | — |
| 212001_at | SFRS14 |
| 208637_x_at | ACTN1 |
| 201997_s_at | SPEN |
| 205073_at | CYP2J2 |
| 40837_at | TLE2 |
| 204447_at | ProSAPiP1 |
| 204604_at | PFTK1 |
| 210273_at | PCDH7 |
| 208614_s_at | FLNB |
| 206510_at | SIX2 |
| 200675_at | CD81 |
| 219228_at | ZNF331 |
| 209426_s_at | AMACR |
| 204000_at | GNB5 |
| 221742_at | CUGBP1 |
| 208883_at | EDD1 |
| 210166_at | TLR5 |
| 211026_s_at | MGLL |
| 220446_s_at | CHST4 |
| 207636_at | SERPINI2 |
| 212226_s_at | PPAP2B |
| 210347_s_at | BCL11A |
| 218424_s_at | STEAP3 |
| 204287_at | SYNGR1 |
| 205489_at | CRYM |
| 36129_at | RUTBC1 |
| 215418_at | PARVA |
| 213029_at | NFIB |
| 221016_s_at | TCF7L1 |
| 209737_at | MAGI2 |
| 220389_at | CCDC81 |
| 213622_at | COL9A2 |
| 204740_at | CNKSR1 |
| 212126_at | — |
| 207760_s_at | NCOR2 |
| 205258_at | INHBB |
| 213169_at | — |
| 33760_at | PEX14 |
| 220968_s_at | TSPAN9 |
| 221792_at | RAB6B |
| 205752_s_at | GSTM5 |
| 218974_at | FLJ10159 |
| 221748_s_at | TNS1 |
| 212185_x_at | MT2A |
| 209500_x_at | TNFSF13 /// TNFSF12-TNFSF13 |
| 215445_x_at | 1-Mar |
| 220625_s_at | ELF5 |
| 32137_at | JAG2 |
| 219747_at | FLJ23191 |
| 201397_at | PHGDH |
| 207913_at | CYP2F1 |
| 217853_at | TNS3 |
| 1598_g_at | GAS6 |
| 203799_at | CD302 |
| 203329_at | PTPRM |
| 208712_at | CCND1 |
| 210314_x_at | TNFSF13 /// TNFSF12-TNFSF13 |
| 213217_at | ADCY2 |
| 200953_s_at | CCND2 |
| 204326_x_at | MT1X |
| 213488_at | SNED1 |
| 213505_s_at | SFRS14 |
| 200982_s_at | ANXA6 |
| 211732_x_at | HNMT |
| 202587_s_at | AK1 |
| 396_f_at | EPOR |
| 200878_at | EPAS1 |
| 213228_at | PDE8B |
| 215785_s_at | CYFIP2 |
| 213601_at | SLIT1 |
| 37953_s_at | ACCN2 |
| 205206_at | KAL1 |
| 212859_x_at | MT1E |
| 217165_x_at | MT1F |
| 204754_at | HLF |
| 218225_at | SITPEC |
| 209784_s_at | JAG2 |
| 211538_s_at | HSPA2 |
| 211456_x_at | LOC650610 |
| 204734_at | KRT15 |
| 201563_at | SORD |
| 202746_at | ITM2A |
| 218025_s_at | PECI |
| 203914_x_at | HPGD |
| 200884_at | CKB |
| 204753_s_at | HLF |
| 207718_x_at | CYP2A6 /// CYP2A7 /// CYP2A7P1 /// CYP2A13 |
| 218820_at | C14orf132 |
| 204745_x_at | MT1G |
| 204379_s_at | FGFR3 |
| 207808_s_at | PROS1 |
| 207547_s_at | FAM107A |
| 208581_x_at | MT1X |
| 205384_at | FXYD1 |
| 213629_x_at | MT1F |
| 823_at | CX3CL1 |
| 203687_at | CX3CL1 |
| 211295_x_at | CYP2A6 |
| 204755_x_at | HLF |
| 209897_s_at | SLIT2 |
| 40093_at | BCAM |
| 211726_s_at | FMO2 |
| 206461_x_at | MT1H |
| 219250_s_at | FLRT3 |
| 210524_x_at | — |
| 220798_x_at | PRG2 |
| 219410_at | TMEM45A |
| 205680_at | MMP10 |
| 217767_at | C3 /// LOC653879 |
| 220562_at | CYP2W1 |
| 210445_at | FABP6 |
| 205725_at | SCGB1A1 |
| 213432_at | MUC5B /// LOC649768 |
| 209074_s_at | FAM107A |
| 216346_at | SEC14L3 |

TABLE 9

107 Nose Leading Edge Genes

| AffxID | Hugo ID |
|---|---|
| 203369_x_at | — |
| 218434_s_at | AACS |
| 205566_at | ABHD2 |
| 217687_at | ADCY2 |
| 210505_at | ADH7 |
| 205623_at | ALDH3A1 |
| 200615_s_at | AP2B1 |
| 214875_x_at | APLP2 |
| 212724_at | ARHE |
| 201659_s_at | ARL1 |
| 208736_at | ARPC3 |
| 213624_at | ASM3A |
| 209309_at | AZGP1 |
| 217188_s_at | C14orf1 |
| 200620_at | C1orf8 |
| 200068_s_at | CANX |
| 213798_s_at | CAP1 |
| 200951_s_at | CCND2 |
| 202769_at | CCNG2 |
| 201884_at | CEACAM5 |
| 203757_s_at | CEACAM6 |
| 214665_s_at | CHP |
| 205328_at | CLDN10 |
| 203663_at | COX5A |
| 202119_s_at | CPNE3 |
| 221156_x_at | CPR8 |
| 201487_at | CTSC |
| 205749_at | CYP1A1 |
| 207913_at | CYP2F1 |
| 206153_at | CYP4F11 |
| 206514_s_at | CYP4F3 |
| 216351_x_at | DAZ4 |
| 203799_at | DCL-1 |
| 212665_at | DKFZP434J214 |
| 201430_s_at | DPYSL3 |
| 211048_s_at | ERP70 |
| 219118_at | FKBP11 |
| 214119_at | FKBP1A |
| 208918_s_at | FLJ13052 |
| 217487_x_at | FOLH1 |
| 200748_s_at | FTH1 |
| 201723_s_at | GALNT1 |
| 218885_s_at | GALNT12 |
| 203397_s_at | GALNT3 |
| 218313_s_at | GALNT7 |
| 203925_at | GCLM |
| 219508_at | GCNT3 |
| 202722_s_at | GFPT1 |
| 204875_s_at | GMDS |
| 205042_at | GNE |
| 208612_at | GRP58 |
| 214040_s_at | GSN |
| 214307_at | HGD |
| 209806_at | HIST1H2BK |
| 202579_x_at | HMGN4 |
| 207180_s_at | HTATIP2 |
| 206342_x_at | IDS |
| 203126_at | IMPA2 |
| 210927_x_at | JTB |
| 203163_at | KATNB1 |
| 204017_at | KDELR3 |
| 213174_at | KIAA0227 |
| 212806_at | KIAA0367 |
| 210616_s_at | KIAA0905 |
| 221841_s_at | KLF4 |
| 203041_s_at | LAMP2 |
| 213455_at | LOC92689 |
| 218684_at | LRRC5 |
| 204059_s_at | ME1 |
| 207430_s_at | MSMB |
| 210472_at | MT1G |
| 213432_at | MUC5B |
| 211498_s_at | NKX3-1 |
| 201467_s_at | NQO1 |
| 206303_s_at | NUDT4 |
| 213498_at | OASIS |
| 200656_s_at | P4HB |
| 213441_x_at | PDEF |
| 207469_s_at | PIR |
| 207222_at | PLA2G10 |
| 209697_at | PPP3CC |
| 201923_at | PRDX4 |
| 200863_s_at | RAB11A |
| 208734_x_at | RAB2 |
| 203911_at | RAP1GA1 |
| 218723_s_at | RGC32 |
| 200087_s_at | RNP24 |
| 200872_at | S100A10 |
| 205979_at | SCGB2A1 |
| 202481_at | SDR1 |
| 217977_at | SEPX1 |
| 221041_s_at | SLC17A5 |
| 203306_s_at | SLC35A1 |
| 207528_s_at | SLC7A11 |
| 202287_s_at | TACSTD2 |
| 210978_s_at | TAGLN2 |
| 205513_at | TCN1 |
| 201666_at | TIMP1 |
| 208699_x_at | TKT |
| 217979_at | TM4SF13 |
| 203824_at | TM4SF3 |
| 200929_at | TMP21 |
| 221253_s_at | TXNDC5 |
| 217825_s_at | UBE2J1 |
| 215125_s_at | UGT1A10 |
| 210064_s_at | UPK1B |
| 202437_s_at | CYP1B1 |

TABLE 10

70 gene list

| AFFYID | Gene Name (HUGO ID) |
|---|---|
| 213693_s_at | MUC1 |
| 211695_x_at | MUC1 |
| 207847_s_at | MUC1 |
| 208405_s_at | CD164 |
| 220196_at | MUC16 |
| 217109_at | MUC4 |
| 217110_s_at | MUC4 |
| 204895_x_at | MUC4 |
| 214385_s_at | MUC5AC |
| 1494_f_at | CYP2A6 |
| 210272_at | CYP2B7P1 |
| 206754_s_at | CYP2B7P1 |
| 210096_at | CYP4B1 |
| 208928_at | POR |
| 207913_at | CYP2F1 |
| 220636_at | DNAI2 |
| 201999_s_at | DYNLT1 |
| 205186_at | DNALI1 |
| 220125_at | DNAI1 |
| 210345_s_at | DNAH9 |
| 214222_at | DNAH7 |
| 211684_s_at | DYNC1I2 |
| 211928_at | DYNC1H1 |
| 200703_at | DYNLL1 |
| 217918_at | DYNLRB1 |
| 217917_s_at | DYNLRB1 |
| 209009_at | ESD |
| 204418_x_at | GSTM2 |
| 215333_x_at | GSTM1 |
| 217751_at | GSTK1 |
| 203924_at | GSTA1 |
| 201106_at | GPX4 |
| 200736_s_at | GPX1 |
| 204168_at | MGST2 |
| 200824_at | GSTP1 |

TABLE 10-continued

70 gene list

| AFFYID | Gene Name (HUGO ID) |
|---|---|
| 211630_s_at | GSS |
| 201470_at | GSTO1 |
| 201650_at | KRT19 |
| 209016_s_at | KRT7 |
| 209008_x_at | KRT8 |
| 201596_x_at | KRT18 |
| 210633_x_at | KRT10 |
| 207023_x_at | KRT10 |
| 212236_x_at | KRT17 |
| 201820_at | KRT5 |
| 204734_at | KRT15 |
| 203151_at | MAP1A |
| 200713_s_at | MAPRE1 |
| 204398_s_at | EML2 |
| 40016_g_at | MAST4 |
| 208634_s_at | MACF1 |
| 205623_at | ALDH3A1 |
| 212224_at | ALDH1A1 |
| 205640_at | ALDH3B1 |
| 211004_s_at | ALDH3B1 |
| 202054_s_at | ALDH3A2 |
| 205208_at | ALDH1L1 |
| 201612_at | ALDH9A1 |
| 201425_at | ALDH2 |
| 201090_x_at | K-ALPHA-1 |
| 202154_x_at | TUBB3 |
| 202477_s_at | TUBGCP2 |
| 203667_at | TBCA |
| 204141_at | TUBB2A |
| 207490_at | TUBA4 |
| 208977_x_at | TUBB2C |
| 209118_s_at | TUBA3 |
| 209251_x_at | TUBA6 |
| 211058_x_at | K-ALPHA-1 |
| 211072_x_at | K-ALPHA-1 |
| 211714_x_at | TUBB |
| 211750_x_at | TUBA6 |
| 212242_at | TUBA1 |
| 212320_at | TUBB |
| 212639_x_at | K-ALPHA-1 |
| 213266_at | 76P |
| 213476_x_at | TUBB3 |
| 213646_x_at | K-ALPHA-1 |
| 213726_x_at | TUBB2C |

Additionally, one can use any one or a combination of the genes listed in Table 9.

The analysis of the gene expression of one or more genes and/or transcripts of the groups or their subgroups of the present invention can be performed using any gene expression method known to one skilled in the art. Such methods include, but are not limited to expression analysis using nucleic acid chips (e.g. Affymetrix chips) and quantitative RT-PCR based methods using, for example real-time detection of the transcripts. Analysis of transcript levels according to the present invention can be made using total or messenger RNA or proteins encoded by the genes identified in the diagnostic gene groups of the present invention as a starting material. In the preferred embodiment the analysis is an immunohistochemical analysis with an antibody directed against proteins comprising at least about 10-20, 20-30, preferably at least 36, at least 36-50, 50, about 50-60, 60-70, 70-80, 80-90, 96, 100-180, 180-200, 200-250, 250-300, 300-350, 350400, 400450, 450-500, 500-535 proteins encoded by the genes and/or transcripts as shown in Tables 1-7.

The methods of analyzing transcript levels of the gene groups in an individual include Northern-blot hybridization, ribonuclease protection assay, and reverse transcriptase polymerase chain reaction (RT-PCR) based methods. The different RT-PCR based techniques are the most suitable quantification method for diagnostic purposes of the present invention, because they are very sensitive and thus require only a small sample size which is desirable for a diagnostic test. A number of quantitative RT-PCR based methods have been described and are useful in measuring the amount of transcripts according to the present invention. These methods include RNA quantification using PCR and complementary DNA (cDNA) arrays (Shalon et al., Genome Research 6(7):639-45, 1996; Bernard et al., Nucleic Acids Research 24(8):143542, 1996), real competitive PCR using a MALDI-TOF Mass spectrometry based approach (Ding et al, PNAS, 100: 3059-64, 2003), solid-phase mini-sequencing technique, which is based upon a primer extension reaction (U.S. Pat. No. 6,013,431, Suomalainen et al. Mol. Biotechnol. June; 15(2):123-31, 2000), ion-pair high-performance liquid chromatography (Doris et al. J. Chromatogr. A May 8; 806(1):47-60, 1998), and 5' nuclease assay or real-time RT-PCR (Holland et al. Proc Natl Acad Sci USA 88: 7276-7280, 1991).

Methods using RT-PCR and internal standards differing by length or restriction endonuclease site from the desired target sequence allowing comparison of the standard with the target using gel electrophoretic separation methods followed by densitometric quantification of the target have also been developed and can be used to detect the amount of the transcripts according to the present invention (see, e.g., U.S. Pat. Nos. 5,876,978; 5,643,765; and 5,639,606.

The samples are preferably obtained from bronchial airways using, for example, endoscopic cytobrush in connection with a fiber optic bronchoscopy. In one embodiment, the cells are obtained from the individual's mouth buccal cells, using, for example, a scraping of the buccal mucosa.

In one preferred embodiment, the invention provides a prognostic and/or diagnostic immunohistochemical approach, such as a dip-stick analysis, to determine risk of developing lung disease. Antibodies against proteins, or antigenic epitopes thereof, that are encoded by the group of genes of the present invention, are either commercially available or can be produced using methods well know to one skilled in the art.

The invention contemplates either one dipstick capable of detecting all the diagnostically important gene products or alternatively, a series of dipsticks capable of detecting the amount proteins of a smaller sub-group of diagnostic proteins of the present invention.

Antibodies can be prepared by means well known in the art. The term "antibodies" is meant to include monoclonal antibodies, polyclonal antibodies and antibodies prepared by recombinant nucleic acid techniques that are selectively reactive with a desired antigen. Antibodies against the proteins encoded by any of the genes in the diagnostic gene groups of the present invention are either known or can be easily produced using the methods well known in the art. Internet sites such as Biocompare through the World Wide Web at biocompare.com at abmatrix to provide a useful tool to anyone skilled in the art to locate existing antibodies against any of the proteins provided according to the present invention.

Antibodies against the diagnostic proteins according to the present invention can be used in standard techniques such as Western blotting or immunohistochemistry to quantify the level of expression of the proteins of the diagnostic airway proteome. This is quantified according to the expression of the gene transcript, i.e. the increased expression of transcript corresponds to increased expression of the gene product, i.e. protein. Similarly decreased expression of the transcript corresponds to decreased expression of the gene product or protein. Detailed guidance of the increase or decrease of expression of preferred transcripts in lung disease, particularly lung dancer, is set forth in the tables. For example, Tables 5 and 6 describe a group of genes the expression of which is altered in lung cancer.

Immunohistochemical applications include assays, wherein increased presence of the protein can be assessed, for example, from a saliva or sputum sample.

The immunohistochemical assays according to the present invention can be performed using methods utilizing solid supports. The solid support can be a any phase used in performing immunoassays, including dipsticks, membranes, absorptive pads, beads, microtiter wells, test tubes, and the like. Preferred are test devices which may be conveniently used by the testing personnel or the patient for self-testing, having minimal or no previous training. Such preferred test devices include dipsticks, membrane assay systems as described in U.S. Pat. No. 4,632,901. The preparation and use of such conventional test systems is well described in the patent, medical, and scientific literature. If a stick is used, the anti-protein antibody is bound to one end of the stick such that the end with the antibody can be dipped into the solutions as described below for the detection of the protein. Alternatively, the samples can be applied onto the antibody-coated dipstick or membrane by pipette or dropper or the like.

The antibody against proteins encoded by the diagnostic airway transcriptome (the "protein") can be of any isotype, such as IgA, IgG or IgM, Fab fragments, or the like. The antibody may be a monoclonal or polyclonal and produced by methods as generally described, for example, in Harlow and Lane, Antibodies, A Laboratory Manual, Cold Spring Harbor Laboratory, 1988, incorporated herein by reference. The antibody can be applied to the solid support by direct or indirect means. Indirect bonding allows maximum exposure of the protein binding sites to the assay solutions since the sites are not themselves used for binding to the support. Preferably, polyclonal antibodies are used since polyclonal antibodies can recognize different epitopes of the protein thereby enhancing the sensitivity of the assay.

The solid support is preferably non-specifically blocked after binding the protein antibodies to the solid support. Non-specific blocking of surrounding areas can be with whole or derivatized bovine serum albumin, or albumin from other animals, whole animal serum, casein, non-fat milk, and the like.

The sample is applied onto the solid support with bound protein-specific antibody such that the protein will be bound to the solid support through said antibodies. Excess and unbound components of the sample are removed and the solid support is preferably washed so the antibody-antigen complexes are retained on the solid support. The solid support may be washed with a washing solution which may contain a detergent such as Tween-20, Tween-80 or sodium dodecyl sulfate.

After the protein has been allowed to bind to the solid support, a second antibody which reacts with protein is applied. The second antibody may be labeled, preferably with a visible label. The labels may be soluble or particulate and may include dyed immunoglobulin binding substances, simple dyes or dye polymers, dyed latex beads; dye-containing liposomes, dyed cells or organisms, or metallic, organic, inorganic, or dye solids. The labels may be bound to the protein antibodies by a variety of means that are well known in the art. In some embodiments of the present invention, the labels may be enzymes that can be coupled to a signal producing system. Examples of visible labels include alkaline phosphatase, beta-galactosidase, horseradish peroxides; and biotin. Many enzyme-chromogen or enzyme-substrate-chromogen combinations are known and used for enzyme-linked assays. Dye labels also encompass radioactive labels and fluorescent dyes.

Simultaneously with the sample, corresponding steps may be carried out with a known amount or amounts of the protein and such a step can be the standard for the assay. A sample from a healthy individual exposed to a similar air pollutant such as cigarette smoke, can be used to create a standard for any and all of the diagnostic gene group encoded proteins.

The solid support is washed again to remove unbound labeled antibody and the labeled antibody is visualized and quantified. The accumulation of label will generally be assessed visually. This visual detection may allow for detection of different colors, for example, red color, yellow color, brown color, or green color, depending on label used. Accumulated label may also be detected by optical detection devices such as reflectance analyzers, video image analyzers and the like. The visible intensity of accumulated label could correlate with the concentration of protein in the sample. The correlation between the visible intensity of accumulated label and the amount of the protein may be made by comparison of the visible intensity to a set of reference standards. Preferably, the standards have been assayed in the same way as the unknown sample, and more preferably alongside the sample, either on the same or on a different solid support.

The concentration of standards to be used can range from about 1 mg of protein per liter of solution, up to about 50 mg of protein per liter of solution. Preferably, two or more different concentrations of an airway gene group encoded proteins are used so that quantification of the unknown by comparison of intensity of color is more accurate.

For example, the present invention provides a method for detecting risk of developing lung cancer in a subject exposed to cigarette smoke comprising measuring the transcription profile in a nasal epithelial cell sample of the proteins encoded by one or more groups of genes of the invention in a biological sample of the subject. Preferably at least about 30, still more preferably at least about 36, 40, 50, 60, 70, 80, 90, 100, 110, 120, 130, 140, 150, 160, 170, or about 180 of the proteins encoded by the airway transcriptome in a biological sample of the subject are analyzed. The method comprises binding an antibody against each protein encoded by the gene in the gene group (the "protein") to a solid support chosen from the group consisting of dip-stick and membrane; incubating the solid support in the presence of the sample to be analyzed under conditions where antibody-antigen complexes form; incubating the support with an anti-protein antibody conjugated to a detectable moiety which produces a signal; visually detecting said signal, wherein said signal is proportional to the amount of protein in said sample; and comparing the signal in said sample to a standard, wherein a difference in the amount of the protein in the sample compared to said standard of the same group of proteins, is indicative of diagnosis of or an increased risk of developing lung cancer. The standard levels are measured to indicate expression levels in an airway exposed to cigarette smoke where no cancer has been detected.

The assay reagents, pipettes/dropper, and test tubes may be provided in the form of a kit. Accordingly, the invention further provides a test kit for visual detection of the proteins encoded by the airway gene groups, wherein detection of a level that differs from a pattern in a control individual is considered indicative of an increased risk of developing lung disease in the subject. The test kit comprises one or more solutions containing a known concentration of one or more proteins encoded by the airway transcriptome (the "protein") to serve as a standard; a solution of a anti-protein antibody bound to an enzyme; a chromogen which changes color or shade by the action of the enzyme; a solid support chosen from the group consisting of dip-stick and membrane carrying on the surface thereof an antibody to the protein. Instructions including the up or down regulation of the each of the genes in the groups as provided by the Tables 1 and 2 are included with the kit.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genuine Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* 3$^{rd}$ Ed., W.H. Freeman Pub., New York, NY and Berg et al. (2002) *Biochemistry*, 5$^{th}$ Ed., W.H. Freeman Pub., New York, NY, all of which are herein incorporated in their entirety by reference for all purposes.

The methods of the present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242, 974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide and protein arrays.

Nucleic acid arrays that are useful in the present invention include, but are not limited to those that are commercially available from Affymetrix (Santa Clara, CA) under the brand name GeneChip7. Example arrays are shown on the website at affymetrix.com.

Examples of gene expression monitoring, and profiling methods that are useful in the methods of the present invention are shown in U.S. Pat. Nos. 5,800,992, 6,013,449, 6,020,135, 6,033,860, 6,040,138, 6,177,248 and 6,309,822.

Other examples of uses are embodied in U.S. Pat. Nos. 5,871,928, 5,902,723, 6,045,996, 5,541,061, and 6,197,506:

The present invention also contemplates sample preparation methods in certain preferred embodiments. Prior to or concurrent with expression analysis, the nucleic acid sample may be amplified by a variety of mechanisms, some of which may employ PCR. See, e.g., *PCR Technology: Principles and Applications for DNA Amplification* (Ed. H. A. Erlich, Freeman Press, NY, NY, 1992); *PCR Protocols: A Guide to Methods and Applications* (Eds. Innis, et al., Academic Press, San Diego, CA, 1990); Mattila et al., *Nucleic Acids Res.* 19, 4967 (1991); Eckert et al., *PCR Methods and Applications* 1, 17 (1991); *PCR* (Eds. McPherson et al, IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (U.S. Pat. Nos. 5,409,818, 5,554,517, and 6,063, 603). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described, for example, in Dong et al., Genome Research 11, 1418 (2001), in U.S. Pat. Nos. 6,361,947, 6,391,592 and U.S. patent application Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, CA, 1987); Young and Davism, *P.N.A.S,* 80: 1194 (1983). Methods and apparatus for carrying out repeated and controlled hybridization reactions have been described, for example, in U.S. Pat. Nos. 5,871,928, 5,874,219, 6,045,996 and 6,386,749, 6,391,623 each of which are incorporated herein by reference The present invention also contemplates signal detection of hybridization between the sample and the probe in certain embodiments. See, for example, U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in provisional U.S. Patent application 60/364,731 and in PCT Application PCT/US99/06097 (published as WO99/47964).

Examples of methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964).

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The present invention also makes use of various computer program products and software for a variety of purposes, such as probe design, management of data, analysis, and instrument operation. See, for example, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have embodiments that include methods for providing gene expression profile information over networks such as the Internet as shown in, for example, U.S. patent application Ser. Nos. 10/063,559, 60/349,546, 60/376,003, 60/394,574, 60/403,381.

Throughout this specification, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 10-20 should be considered to have specifically disclosed sub-ranges such as from 10-13, from 10-14, from 10-15, from 11-14, from 11-16, etc., as well as individual numbers within that range, for example, 10, 11, 12, 13, 14, 15, 16, 17, 18, 19, and 20. This applies regardless of the breadth of the range. In addition, the fractional ranges are also included in the exemplified amounts that are described. Therefore, for example, a range of 1-3 includes fractions such as 1.1, 1.2, 1.3, 1.4, 1.5, 1.6, etc. This applies particularly to the amount of increase or decrease of expression of any particular gene or transcript.

The present invention has many preferred embodiments and relies on many patents, applications and other references for details known to those of the art. Therefore, when a reference, for example a patent application is cited in the specification, it should be understood that it is incorporated by reference in its entirety for all purposes as well as for the proposition that is recited.

EXAMPLES

Example 1

In this study, we obtained nucleic acid samples (RNA/DNA) from nose epithelial cells. We also obtained nucleic acids from blood to provide one control. We used our findings in the PCT/US2006/014132 to compare the gene expression profile in the bronchial epithelial cells as disclosed in the PCT/US2006/014132 to the gene expression pattern discovered in this example from the nasal epithelial cells.

We have explored the concept that inhaled toxic substances create a epithelial cell "field of injury" that extends throughout the respiratory tract. We have developed the hypothesis that this "field of injury", measured most recently in our laboratory with high density gene expression arrays, provides information about the degree of airway exposure to a toxin and the way in which an individual has responded to that toxin. Our studies have been focused on cigarette smoke, the major cause of lung cancer and of COPD, although it is likely that most inhaled toxins result in a change in gene expression of airway epithelial cells.

We began our studies by examining allelic loss in bronchial epithelial cells brushed from airways during diagnostic bronchcoscopy. We showed, as have others, that allelic loss occurs throughout the intra-pulmonary airways in smokers with lung cancer, on the side of the cancer as well as the opposite side from the cancer. Allelic loss also occurs, but to a lesser extent, in airway epithelial cells of smokers without cancer (Clinical Cancer Research 5:2025, 1999). We expended these studies to adenocarcinomas from smokers and non-smokers and showed that there was a "field of injury" in non-cancerous lung tissue of smokers, but not in non-smokers (Lung Cancer. 39:23, 2003, Am. J. Respir. Cell. Mol. Biol. 29:157, 2003).

We have progressed to using high density arrays to explore patterns of gene expression that occur in large airway epithelial cells of smokers and non-smokers. We have defined the types of genes that are induced by cigarette smoke, the relation to the amount smoked, racial differences (ATS) in how individuals respond to cigarette smoke, the changes that are reversible and not reversible in individuals who stop smoking (PNAS. 101:10143-10148, 2004). In addition, we have recently documented changes that occur in smokers who develop lung cancer (submitted and AACR), and changes that occur in smokers who develop COPD (Am. J. Respir. Cell Mol. Biol. 31: 601, 2004). All of these studies are ongoing in our laboratory and all depend on obtaining large airway epithelial cells at bronchoscopy, a process that does not lend itself to surveying large populations in epidemiologic studies.

In order to develop a tool that could assay airway epithelial gene expression without bronchoscopy in large numbers of smokers, we begun to explore the potential of using epithelial cells obtained from the oral mucosa. We developed a method of obtaining RNA from mouth epithelial cells and could measure expression levels of a few genes that changed in the bronchial epithelium of smokers, but problems with the quality and quantity of RNA obtained from the mouth has limited widespread application of this method (Biotechniques 36:484-87, 2004).

We have now shown that epithelial cells obtained by brushing the nasal mucosa could be used as a diagnostic and prognostic toot for lung disorders. Preliminary results show that we can obtain abundant amounts of high quality RNA and DNA from the nose with ease (see protocol below), that we can measure gene expression using this RNA and high density microarrays and that many of the genes that change with smoking in the bronchial epithelium also change in the nose (see FIG. 1). We have further shown that gene expression in nasal epithelium can be used to define a potentially diagnostic and clinical stage-specific pattern of gene expression in subjects with sarcoidosis, even when the sarcoidosis does not clinically involve the lung (see FIG. 2). We can also obtain DNA from these same specimens allowing us to assess gene methylation patterns and genetic polymorphisms that explain changes in gene expression.

These studies show that gene expression in nasal epithelial cells, obtained in a non-invasive fashion, can indicate individual responses to a variety of inhaled toxins such as cigarette smoke, and can provide diagnostic, and possibly prognostic and pathogenetic information about a variety of diseases that involve the lung.

Accordingly, based on our studies we have now developed the method of analyzing nasal epithelial cells as a technique and as a screeching tool that can be used to evaluate individual and population responses to a variety of environmental toxins and as a diagnostic/prognostic tool for a variety of lung diseases, including lung cancer. While our initial studies utilize "discovery-based" genome-wide expression profiling, it is likely that initial studies will ultimately lead to a simpler "defined-gene" platform that will be less complicated and costly and might be used in the field.

Protocol for Noninvasive Nasal Epithelium RNA and DNA Isolation:

Following local anesthesia with 2% lidocaine solution, a Cytosoft brush is inserted into the right nare and under the inferior turbinate using a nasal speculum for visualization. The brush is turned 3 times to collect epithelial cells and immediately placed into RNA Later. Repeat brushing is performed and the 2nd brush is placed in PBS for DNA isolation, Extending the Airway 'Field of Injury' to the Mouth and Nose While we have demonstrated gene expression differences in bronchial epithelium associated with current, cumulative and past tobacco exposure, the relatively invasive nature of bronchoscopy makes the collection of these tissue samples challenging for large scale population studies and for studies of low-disease-risk individuals. Given our hypothesis that the field of tobacco injury extends to epithelial cells lining the entire respiratory tract, we performed a pilot study to explore the relationship between bronchial, mouth and nasal gene expression in response to tobacco exposure as nasal and oral buccal epithelium are exposed to cigarette smoke and can be obtained using noninvasive methods. In our pilot study, we collected 15 nasal epithelial samples (8 never smokers, 7 current smokers) via brushing the right inferior turbinate as described in our Research Methods and Design section. In addition, we collected buccal mucosa epithelial samples from 10 subjects (5 never smokers, 5 current smokers) using a scraping device that we have described previously [38] (see Appendix). All samples were run on Affymetrix HG-UL33A arrays. Due to the small amounts (1-2 ug) of partially degraded RNA obtained from the mouth, samples were collected serially on each subject monthly and pooled to yield sufficient RNA (6-8 ug), Low transcript detection rates were observed for mouth samples, likely as a result of lower levels of intact full-length mRNA in the mouth samples A relationship between the tobacco-smoke induced pattern of gene expression in all three tissues was first identified by Gene Set Enrichment Analysis (GSEA; [39]) which demonstrates that genes differentially expressed in the bronchus are similarly changed in both the mouth and nose (GSEA $p<0.01$). We next performed a 2 way ANOVA to identify 365 genes are differentially expressed with smoking across all three tissues at $p<0.001$. PCA of all samples normalized within each tissue for these 365 genes is shown in FIG. 5.

Finally, while this pilot study in the nose and mouth was not well powered for class prediction, we explored the possibility of using these tissues to identify biomarkers for smoke exposure. The genes with the 20 highest and 20 lowest signal-to-noise ratios between smokers and never-smokers were identified in both the nose and mouth. A classifier was then trained using these genes in bronchial epithelial samples (15 current and 15 never smokers), and tested on an independent test set of 41 samples. Genes selected from mouth and nose classify bronchial epithelium of current vs. never-smokers with high accuracy:

| | Genes selected from Nose | Genes selected from Mouth | Genes selected from Bronch | Random sselected Genes |
|---|---|---|---|---|
| Bronchus Classification Accuracy | 82.8% | 79.2% | 93.2% | 64.2 ± 8.1 |

The pilot study established the feasibility of obtaining significant quantities of good quality RNA from brushings of the nasal mucosa suitable for DNA microarray studies and has demonstrated a relationship between previously defined smoking-related changes in the bronchial airway and those occurring in the nasal epithelium. While the quality and quantity of RNA obtained from buccal mucosa complicates analysis on the U133A platform, pooled studies suggest a gene-expression relationship to the bronchial airway in the setting of tobacco exposure. These results support the central hypothesis that gene expression profiles in the upper airway reflect host response to exposure. By using a novel array platform with the potential to measure gene expression in setting of partially degraded RNA, we propose to more fully explore the ability to create biomarkers of tobacco exposure with samples from nose and mouth epithelium.

Example 2

A Comparison of the Genomic Response to Smoking in Buccal, Nasal and Airway Epithelium Approximately 1.3 billion people smoke cigarettes worldwide which accounts for almost 5 million preventable deaths per year (1). Smoking is a significant risk factor for lung cancer, the leading cause of cancer-related death in the United States, and chronic obstructive pulmonary disease (COPD), the fourth leading cause of death overall. Approximately 90% of lung cancer can be attributed to cigarette smoking, yet only 10-15% of smokers actually develop this disease (2). Despite the well-established causal role of cigarette smoke in lung cancer and COPD, the molecular epidemiology explaining why only a minority of smokers develop them is still poorly understood.

Cigarette smoking has been found to induce a number of changes in both the upper and lower respiratory tract epithelia including cellular atypia (3, 4), aberrant gene expression, loss of heterozygosity (3, 5) and promoter hypermethylation. Several authors have reported molecular and genetic changes such as LOH or microsatellite alterations dispersed throughout the airway epithelium of smokers including areas that are histologically normal (4, 6). We previously have characterized the effect of smoking on the normal human airway epithelial transcriptome and found that smoking induces expression of airway genes involved in regulation of oxidant stress, xenobiotic metabolism, and oncogenesis while suppressing those involved in regulation of inflammation and tumor suppression (7). While this bronchoscopy-based study elucidated some potential candidates for biomarkers of smoking related lung damage, there is currently a significant impetus to develop less invasive clinical specimens to serve as surrogates for smoking related lung damage.

Oral and nasal mucosa are attractive candidates for a biomarkers since they are exposed to high concentrations of inhaled carcinogens and are definitively linked to smoking-related diseases (8). We have previously shown that it is feasible to obtain sufficient RNA from both nasal (9) and buccal mucosa for gene expression analysis (10) despite the high level of RNAses in saliva and nasal secretions (11, 12). Few studies have characterized global gene expression in either of these tissues, and none has attempted to establish a link between upper and lower airway gene expression changes that occur with smoking. A pilot study by Smith et. al. used brush biopsies of buccal mucosa from smokers and nonsmokers to obtain RNA for cDNA microarrays and found approximately 100 genes that could distinguish the two groups in training and test sets. While the study provided encouraging evidence that buccal gene expression changes with smoking, many of these genes were undefined ESTs, and the study did not address any potential relationship between genetic responses in the upper and lower airways. Spivak et. al. found a qualitative relationship via PCR (i.e. detected or not detected) between patient matched buccal mucosa and laser-dissected lung epithelial cells across nine carcinogen or oxidant-metabolizing genes (13) in 11 subjects being evaluated for lung cancer. However, quantitative real-time PCR of these genes in buccal mucosa was not able to reliably predict lung cancer vs. control cases. While global gene expression profiling on nasal brushing has been done recently on children with asthma (14), and cystic fibrosis 15), we are unaware of any studies addressing the effects of smoking on nasal epithelial gene expression.

In the current study, we report for the first time, a genome wide expression assay of buccal and nasal mucosa on normal healthy individuals, which herein are referred to as the "normal buccal and nasal transcriptomes". We then evaluate the effects of smoking on these transcriptomes and compare them to a previous bronchial epithelial gene expression dataset. By comparing these smoking-induced changes in the mouth, nose, and bronchus we establish a relationship between the lower and upper airway genetic responses to cigarette smoke and further advance the concept of a smoking-induced "field defect" one global gene expression level. Lastly, we validate the use of mass spectrometry as a feasible method for multiplexed gene expression studies using small amounts of degraded RNA from buccal mucosa scrapings.

Study Population

Microarrays were performed on total of 25 subjects and mass spectrometry validation on 14 additional subjects. Demographic data for the microarray and mass spectrometry validation groups are presented in Table 11:

Microarray analysis of normal tissue samples was performed on previously published datasets collected from the Gene Expression Omnibus (GEO). Ninety two samples spanning 10 different tissues types were analyzed altogether, including 12 nasal and buccal epithelial samples of non-smokers collected for this study. Additional microarray data from normal nasal epithelial samples were also collected to determine the reproducibility of gene expression patterns in nasal tissue collected from a different study. A detailed breakdown of the different tissues analyzed and number of samples within each tissue type are shown in Table 12.

The Relationship between Normal Airway Epithelial Cells

Principal component analysis (PCA) of the normal tissue samples spanning 10 tissue types (n=92 total samples) was performed across the 2382 genes comprising the normal airway transcriptome, which has been previously characterized (Spira et. al, 2004, PNAS). FIG. 7 shows bronchial and nasal epithelial samples clearly grouped together based on the expression of these 2382 genes.

Over represented sets of functional gene categories ("functional sets") among the 2382 normal airway transcriptome were determined by EASE analysis. Table 13 lists the 16 functional sets that were significantly overrepresented among the normal airway transcriptome. On average there were approximately 109 probe sets per functional cluster. A variability metric was used to determine those functional sets that were most different across the 10 tissue types. Ahdehyde dehydrogenase, antigen processing and presentation, and microtubule and cytoskeletal complex were the most variable functional sets. The least variable sets included ribosomal subunits, and nuclear and protein transport. Two dimensional hierarchical clustering was also performed on each of these 16 functional sets to determine which tissues showed similar expression patterns across all the genes in each set. Among the top three most variable functional sets listed above, bronchial and nasal epithelial samples always grouped together (data not shown).

To further examine the relationship between bronchial epithial tissues and other tissues, genes from functional groups commonly expressed in airway epithelium were selected from among the normal airway transcriptome. Genes from the mucin, dynein, microtubule, keratin, glutathione, cytochrome P450, and aldehyde dehydrogenase functional groups were selected from among the 2382 genes in the normal airway transcriptome, based on their gene annotations. Fifty-nine genes from these functional groups were present among the normal airway transcriptome and analyzed using supervised hierarchical clustering, as shown in FIG. 8. Bronchial and nasal epithelial samples clustered together based on the expression of these 59 genes, with many being expressed at higher levels in these two tissues. Genes highly expressed in bronchial and nasal epithelium were generally evenly distributed among the five functional groups. Several dynein, cytochrome P450, and aldehyde dehydrogenase genes were expressed highly in bronchial and nasal epithelium compared to other tissues. Buccal mucosa samples clustered mainly with lung tissue, with specific keratin genes being highly expressed. While some keratins were expressed specifically in skin and esophageal epithelium, other keratins, such as KRT7, KRT8, KRT18, and KRT19 were expressed primarily in bronchial and nasal epithelium. The same pattern was seen with mucin genes, with MUC4, MUC5AC, and MUC16 being expressed primarily in bronchial and nasal epithelium, while MUC1 was expressed in other epithelial tissues. Glutathione genes were expressed highly in bronchial and nasal epithelium as well as other tissues. Microtubule expression was fairly even across all tissues.

To explore the similar expression pattern between bronchial and nasal epithelium, a metagene was created by selected a subset of the 59 functionally relevant normal transcriptome genes with highly correlated expression in between bronchial and nasal samples. All genes which were highly correlated to the metagene (R>.6, p<.001) were selected and analyzed using EASE to determine sets functionally overrepresented categories. The microtubule and cytoskeletal complex functional set was significantly enriched among the genes most highly correlated with the expression pattern of the metagene.

A separate set of normal nasal epithelial samples run on the same microarray platform (16) was used in place of our nasal epithelial dataset to determine the reproducibility of the relationships in gene expression between bronchial and nasal epithelium. This separate nasal epithelial dataset consisted of 11 normal epithelial samples run on Affymetrix HG133A microarrays. These samples were first examined with the 92 normal tissue samples from previous analysis. A correlation matrix was created to determine the average pearson correlation of each set of samples within a tissue type with samples from other tissue types. The two nasal epithelial datasets had the highest correlation with each other, with the next highest correlation being between nasal and bronchial epithelial samples. These 11 nasal epithelial samples also clustered together with bronchial epithelial samples across the entire normal transcriptome and the subset of 59 functionally relevant genes from the transcriptome when used in place of our original 8 nasal epithelial samples.

Effect of Cigarette Smoking on the Airway Epithelial

To examine the effect of cigarette smoke on airway epithelial cells, current and never smokers samples from buccal and nasal epithelial cell samples were analyzed together with current and never smokers from bronchial epithelial samples published previously (Spira et. al, 2004, PNAS). In total there were 82 samples across these three tissue types (57 bronch, 10 buccal, 15 nasal). To determine the relationship in the response to cigarette smoke between these three tissues, expression of 361 genes previously reported to distinguish smokers from non-smokers in bronchial epithelial cells (Spire et. al, 2004, PNAS) was examined across all 82 samples from bronchial, nasal, and buccal epithelium.

The 361 genes as shown in Table 8 most differently expressed in the airway epithelial cells of current and never smokers were generally able to distinguish bronchial, nasal, and buccal epithelial samples based on smoking status using principal component analysis, with few exceptions among buccal mucosa samples (FIG. 3). This finding suggests a relationship between gene expression profiles in epithelial cells in the bronchus and upper airway epithelium in response to cigarette smoke. To further establish this connection across airway epithelial cells, gene set enrichment analysis (GSEA) was performed to determine if genes most differentially expressed in bronchial epithelium based on smoking status were overrepresented among the genes that change with smoking in both nasal and buccal epithelium. We showed that smoking-induced airway genes are significantly enriched among the genes most affected by smoking in buccal mucosa with 101 genes composing the "leading edge subset" (p<.001). The leading edge subset consists of the genes that contribute most to the enrichment of airway genes in buccal mucosa samples. FIG. 6 similarly shows that the genes differing most across the bronchial epithelium of smokers were also significantly enriched among the genes most affected by smoking in nasal epithelial cell samples, with 107 genes comprising the leading edge subset (p<.001). PCA of the leading edge genes show that they are able to separate buccal mucosa samples and nasal epithelial samples (FIG. 7) based on smoking status, suggesting a global relationship in gene expression across airway epithelial cells in response to smoking. EASE analysis of the leading edge subsets from FIG. 5 reveals that overrepresented functional categories from these gene lists include oxidoreductase activity, metal-ion binding, and electron transport activity (see Table 13).

Study Population

We recruited current and never smoker volunteers from Boston Medical Center for a buccal microarray study (n=11), nasal microarray study (n=15) and subsequent prospective buccal epithelial cell mass spectrometry validation (n=14). Current smokers in each group had smoked at least 10 cigarettes per day in the past month, with at least a cumulative 10 pack-year history. Non-smoking volunteers with significant environmental cigarette exposure and subjects with respiratory symptoms, known respiratory, nasal or oral diseases or regular use of inhaled medications were excluded. For each subject, a detailed smoking history was obtained including number of pack-years, number of packs per day, age started, and environmental tobacco exposure. Current and never smokers were matched for age, race and sex. The study was approved by the Institutional Review Board of Boston Medical Center and all subjects provided written informed consent.

Buccal Epithelial Cell Collection

Buccal epithelial cells were collected on 25 subjects (11 for the buccal microarray, study, 14 for the mass spectrometry validation) as previously reported (Spira et. al. 2004, Biotechniques). Briefly, we developed a non-invasive method for obtaining small amounts of RNA from the mouth using a concave plastic tool with serrated edges. Using gentle pressure, the serrated edge was scraped 5 times against the buccal mucosa on the inside left cheek and placed immediately into 1 mL of RNALATER (Qiagen, Valencia, CA). The procedure was repeated for the inside right cheek and the cellular material was combined into one tube. After storage at room temperature for up to 24 hours, total RNA was isolated from the cell pellet using TRIZOL® reagent (Invitrogen, Carlsbad, CA) according to the manufacturer's protocol. The integrity of the RNA was confirmed on an RNA denaturing gel. Epithelial cell content was quantified by cytocentrifugation at 700×g (Cytospin, ThermoShandon, Pittsburgh, PA) of the cell pellet and staining with a cytokeratin antibody (Signet, Dedham, MA). Using this protocol, we were able to obtain an average of 1823 ng+/− 1243 ng of total RNA per collection. Buccal epithelial cells were collected serially over 6 weeks in order to obtain a minimum of 8 ug of RNA per subject. For the 14 subjects included in the mass spectrometry validation, a single collection was sufficient.

Nasal Epithelial Cell Collection

Nasal epithelial cells were collected by first anesthesizing the right nare with 1 cc of 1% lidocaine. A nasal speculum (Bionix, Toledo OH) was use to spread the nare while a standard cytology brush (Cytosoft Brush, Medical Packaging Corporation, Camarillo CA) was inserted underneath the inferior nasal turbinate. The brush was rotated in place once, removed, and immediately placed in 1 mL RNA Later (Qiagen, Valencia, CA). After storage at 4 overnight, RNA was isolated via Qiagen RNEASY® Mini Kits per manufacturer's protocol. As above, the integrity of RNA was confirmed with an RNA denaturing gel and epithelial cell content was quantified by cytocentrifugation.

Bronchial Epithelial Cell Collection

Bronchial epithelial cells were also obtained on a subset of patients in the mass spectrometry study (N=6 of the 14) from brushings of the right mainstem during fibertoptic bronchoscopy with three endoscopic cytobrushes (Cellebrity Endoscopic Cytobrush, Boston Scientific, Boston). After removal of the brush, it was immediately placed in TRIZOL® reagent (Invitrogen), and kept at −80° C. until RNA isolation was performed. RNA was extracted from the brush using the TRIZOL® reagent (Invitrogen, Carlsbad, CA) according to the manufacturer's protocol with an average yield of 8-15 ug of RNA per patient. Integrity of RNA was confirmed by running an RNA-denaturing gel and epithelial cell content was quantified by cyrocentrifugation and cytokeratin staining.

Microarray Data Acquisition and Preprocessing

Eight micrograms of total RNA from buccal epithelial cells (N=11) and nasal epithelial cells (N=15) was processed, labelled, and hybridized to Affymetrix HG-U133A GeneChips containing 22,215 probe sets as previously described (Spire et. al, 2004, PNAS). A single weighted mean expression level for each gene was derived using MICROARRAY SUITE 5.0 (MAS 5.0) software (Affymetrix, Santa Clara, CA). The MAS 5.0 software also generated a detection P value [P(detection)] using a one-sided Wilcoxon sign-ranked test, which indicated whether the transcript was reliably detected. One buccal mucosa microarray sample was excluded from further analysis based on the percentage of genes detected being lower than two standard deviations from the median percentage detected across all buccal mucosa microarray samples, leaving 10 samples for further analysis. All 15 nasal epithelial cell microarray samples contained sufficiently high percentages of genes detected based on the same criteria, and were all included for further analysis. Microarray data from 57 bronchial epithelial cell samples was obtained from previously published data (Spire et. al. 2004, PNAS).

Microarray data from 7 additional normal human tissues was obtained from datasets in the Gene Expression Omnibus (GEO). The samples were selected from normal, non-diseased tissue, where there were at least 5 samples per tissue type. All samples were run on either Affymetrix HGU133A or HGU133 Plus 2.0 microarrays. Array data from normal tissue samples from the following 7 tissues were used (GEO accession number included): lung (GSE1650), skin (GSE5667), esophagus (GSE1420), kidney (GSE3526), bone marrow (GSE3526), heart (GSE2240), and brain (GSE5389). A detailed breakdown of the array data obtained for these tissues can be seen in Table 12.

Microarray data from buccal mucosa, nasal epithelium and bronchial epithelial cell samples, as well at normal tissue samples from the 8 datasets listed above were each normalized using MAS 5.0, where the mean intensity for each array (excluding the top and bottom 2% of genes) was corrected using a scaling factor to set the average target intensity of all probes on the chip to 100. For tissue samples run on the HGU133 Plus 2.0 arrays, only those probe sets in common with the HGU133A array were selected and normalized using MATLAB Student Version 7.1 (The Mathworks, Inc.), where the mean intensity of the selected probes (excluding the top and bottom 2% of genes) was corrected using a scaling factor to set the average target intensity of the remaining probes to 100.

Microarray Data Analysis

Clinical information, array data, and gene annotations are stored in an interactive MYSQL database coded in PERL (37). All statistical analyses described below and within the database were performed using the R v. 2.2.0 software (38). The gene annotations used for each probe set were from the December 2004 NetAffx HG-U133A annotation files.

Principal component analysis (PCA) was performed using the Spotfire DecisionSite software package (39) on the following normal non-smoker tissue samples from 10 different tissue types: bronchial (n=23), nasal (n=8), buccal mucosa (n=5), lung (n=14), skin (n=5), esophagus (n=8), kidney (n=8), bone marrow (n=5), heart (n=5), and brain (n=11). PCA analysis was used to determine relationships in the gene expression of these tissue types across the normal airway transcriptome, which has been previously characterized (Spire et. al, 2004, PNAS).

Functional annotation clustering was performed using the EASE software package (40) to determine overrepresented sets of functional groups ("functional sets") among the normal airway transcriptome. Each functional group within a cluster was given a p-value, determined by a Fisher-Exact test. The significance of the functional cluster was then determined by taking the geometric mean of the p-values of each functional group in the cluster. To limit the number of functional sets returned by EASE, only functional groups from the Gene Ontology (GO) database below the 5th hierarchical node were used.

To determine the variability of the functional sets across the 10 different tissue types, the following formula was used:

$$V = X^-(1 \ldots i)[COV(X^-G1 \ldots X^-Gk)]$$

Where Gk is the expression of gene G across all the samples in tissue type k, i is the total number of genes in a functional cluster, and COV is the coefficient of variation (standard deviation divided by mean) of the average expression of gene G across all tissue types. This produced one variability metric (V) for each functional cluster. All the genes in each functional cluster were then analyzed using 2D hierarchical clustering performed by using log-transformed z-score normalized data with a Pearson con-elation (uncentered) similarity metric and average linkage clustering with CLUSTER and TREEVIEW software (41).

To further analyze the relationship between airway epithelium and other tissue types, genes from the normal airway transcriptome included in functional categories commonly expressed in airway epithelial cells were examined. The functional categories explored were mucin, dynein, microtubule, cytochrome p450, glutathione, aldehyde dehydrogenase, and keratin. Genes from these categories were determined by selecting all those genes from the normal airway transcriptome that were also included in any of these functional groups based on their gene annotation. Fifty-nine genes from the normal airway transcriptome which also spanned the functional categories of interest were further analyzed across the 10 tissues types using supervised hierarchical clustering.

To assess whether genes outside of the normal airway transcriptome were expressed at similar levels in bronchial and nasal epithelium, we created a metagene by taking a subset of the 59 genes from the normal airway transcriptome spanning the specified functional categories which were highly expressed in bronchial and nasal epithelial samples, based on the Pearson correlation similarity metric for these genes. A correlation matrix was then generated between the average expression of the metagene across all 10 tissues and each probe set on the HGU133A array (22215 total probe sets) across all 10 tissues, to determine genes with a similar expression pattern to bronchial and nasal epithelium (a detailed protocol for this analysis can be found in the supplement).

A second nasal epithelial dataset (Wright et. al, 2006. Am J Respir Cell Mol Biol.) was included for further analysis to determine the reproducibility of the expression patterns observed in nasal epithelium compared to other tissues. In all there were 11 nasal epithelial samples from this second dataset (GSE2395) which were used in place of our original 8 nasal samples to determine the reproducibility of gene expression patterns and relationships between nasal epithelium and other tissues.

To determine the relationship in the response to cigarette smoke by bronchial, buccal, and nasal epithelial cells, PCA was performed across 82 smoker and non-smoker samples (57 bronchial, 10 buccal, 15 nasal) using 361 genes differentially expressed between smokers and non-smokers in bronchial epithelial cells (p<.001), as determined from a prior study (Spira et. al, 2004, PNAS). Gene set, enrichment analysis (GSEA) (42) was then used to further establish a global relationship between gene expression profiles from these three tissue types in response to cigarette smoke. Our goal was to determine if the genes most differentially expressed with smoking in bronchial epithelial cells were significantly enriched among the top smoking-induced buccal and nasal epithelial genes based on signal-to-noise ratios. P-values were generated in GSEA by permuting ranked gene labels and generating empirical p-values to determine significant enrichment. The airway genes most significantly enriched among ranked lists of nasal epithelial and buccal mucosa samples (leading edge subsets), were further analyzed using PCA to determine the ability of the leading edge subsets to distinguish samples in the nasal and buccal epithelial datasets based on smoking status.

Table 11 below shows Patient demographic data. Demographic data for patient samples used for microarray analysis (n=10) and mass spectrometry analysis (n=14). P-values calculated by Fisher Extact test Table 13 below shows Significantly overrepresented "functional sets" among the normal airway transcriptome. Sixteen functional sets significantly overrepresented among the normal airway transcriptome, ranked by the variability of each cluster across 10 tissue types.

| Functional Category | Average COV | P-value |
|---|---|---|
| Aldehyde Dehydrogenase | 108.7083218 | 0.052807847 |
| Antigen processing and presentation | 83.83536768 | 0.003259035 |
| Microtubule and Cytoskeletal complex | 74.77767675 | 0.018526945 |
| Carbohydrate and Alcohol catabolism/metabolism | 67.69528886 | 0.025158044 |
| Oxidative phosphorylation, protein/ion transport, metabolism | 66.99814067 | 4.53E−07 |
| ATPase Activity | 62.97844577 | 7.96E−08 |
| Apoptosis | 61.75272195 | 0.005467272 |
| Mitochondrial components and activity | 61.34998026 | 3.65E−09 |
| NADH Dehydrogenase | 58.28368171 | 4.77E−11 |
| Regulation of protein synthesis and metabolism | 55.93424773 | 0.002257705 |
| NF-kB | 55.70796256 | 0.011130609 |
| Protein/macromolecule catabolism | 55.62842326 | 6.74E−05 |
| Intracellular and protein transport | 53.51411018 | 8.10E−09 |
| Protein/Macromolecule Biosynthesis | 52.28818306 | 1.62E−25 |
| Vesicular Transport | 49.6560062 | 0.019136042 |
| Nuclear Transport | 44.88736037 | 0.003807797 |
| Ribosomal Subunits | 42.57469554 | 5.42E−15 |

Table 14 below shows Common overrepresented functional categories among "leading edge subsets" from GSEA analysis. Common EASE molecular functions of leading edge genes from GSEA analysis. P-values were calculated using EASE software.

| | Buccal Microarray (N = 10) | | | Nasal Microarray (N = 15) | | | MS Validation (N = 14) | | |
|---|---|---|---|---|---|---|---|---|---|
| | Smokers | Never | P-Value | Smokers | Never | P-Value | Smokers | Never | P-Value |
| Sex | 1M, 4F | 2M, 3F | (p = 0.42*) | 6 M, 1 F | 5 M, 2 F, 1 U | (p = .58) | 6 M, 1 F | 4 M, 3 F | (p = .24*) |
| Age | 36 (+/−8) | 31 (+/−9) | (p = 0.36) | 47 +/− 12 | 43 +/− 18 | | 59 (+/−15) | 41 (+/−17) | (p = 0.06) |
| Race | 3 CAU, 2 AFA | 2 CAU, 3 AFA | (p = 0.40*) | 3 CAU, 3 AFA, 1 HIS | 5 CAU, 2 AFA, 1 HIS | | 5 CAU, 2 AFA | 4 CAU, 3AFA | (p = .37*) |

Table 12 below shows breakdown of all microarray datasets analyzed in this study.

| Category | Tissue | # Samples | Platform | GEO reference | Sample Description |
|---|---|---|---|---|---|
| epithelial | Mouth | 5 | U133A | n/a | 5 never smokers |
| epithelial | Bronch | 23 | U133A | GSE994 | 23 never smokers |
| epithelial | Nose | 8 | U133A | n/a | 8 never smokers |
| epithelial | Nose | 11 | U133A | GSE2395 | normal nasal epithelium, from cystic fibrosis study |
| epithelial | Lung | 14 | U133A | GSE1650 | from COPD study, no/mild emphezyma patients |
| epithelial | Skin | 5 | U133A | GSE5667 | normal skin tissue |
| Epithelial | Esophagus | 8 | U133A | GSE1420 | normal esophageal epithelium |
| mostly epithelial | Kidney | 8 | U133 + 2.0 | GSE3526 | 4 kidney cortex, 4 kidney medulla (post-mortem) |
| non epithelial | Bone marrow | 5 | U133 + 2.0 | GSE3526 | 5 bone marrow (post-mortem) |
| non epithelial | Heart | 5 | U133A | GSE2240 | left ventricular myocardium, non-failing |
| non epithelial | Brain | 11 | U133A | GSE5389 | postmortem orbitofrontal cortex |

| Molecular Function | P-value (calculated in EASE) |
|---|---|
| Oxidoreductase activity | $p < 1.36 \times 10^{-6}$ |
| Electron transporter activity | $p < 4.67 \times 10^{-5}$ |
| Metal ion binding | $p < .02$ |
| Monooxygenase activity | $p < .02$ |

REFERENCES

All references cited herein and throughout the specification are herein incorporated by reference in their entirety.

1. WHO: The Facts About Smoking and Health, 30 May 2006 [http://www.wpro.who.int/media_centre/fact_sheets/fs_20060530.htm]
. Shields, P. G.: Molecular Epidemiology of lung cancer. Ann. Oncol, 1999, Suppl. 5:7-11.
2. Franklin W A, Gazdar A F, Haney J, Wistuba I I, LaRosa F G, Kennedy T, Ritchey D M, and Miller Y E.: Widely Dispersed p53 mutation in respiratory epithelium. A Novel mechanism for field carcinogenesis. Journal of Clinical Investigation, 1997, 100:2133-2137.
3. Wistuba I I, Lam S, Behrens C, Virmani A K, Fong K M, LeRiche J, Samet J M, Srivastava S, Minna J D, and Gazdar A F: Molecular damage in the bronchial epithelium of current and former smokers. Journal of the National Cancer Institute, 1997, 89:1366-1373.
4. Powell C A, Klares S, O'Connor G, Brody J S: Loss of Heterozygosity in Epithelial Cells Obtained by Bronchial Brushing: Clinical Utility in Lung Cancer. Clinical Cancer Research, 1999, 5: 2025-2034.
5. Thiberville L, Payne P, Vielkinds J, LeRiche 5, Horsman D, Nouvet G, Palcic B, Lam S: Evidence of cumulative gene losses with progression of premalignant epithelial lesions to carcinoma of the bronchus. Cancer Res, 1995, 55: 5133-9.
6. Spira A S, Beane J, Shah V, Schembri F, Yang X, Palma I and Brody J S: Effects of cigarette Smoke on the human airway epithelial transcriptome. PNAS, 2004, 101:10143-10148.
7. Phillips D E, Hill L, Weller M, Willett M, and Bakewell R. R Tobacco smoke and the upper airway. Clin. Otoloaryngol. 2003, 28, 492-496.
8. 7.5 Immunophenotype of the Nasal Mucosa in Sarcoidosis, [Publication Page: A795]
9. D. M. Serlin. MD, X. F. Li, PhD, J. Spiegel, MD, K. Steiling, MD, C J. O'Hara, MD, A. Spire, MD, A. W. O'Regan, MD, J. S. Berman, MD, Boston, Mass, Galway, Ireland. Abstract, ATS 2006
10. Spira A, Beane J, Schembri F, Liu G, Ding C, Gilman S, Yang X, Cantor C and Brody J S: Noninvasive method for obtaining RNA from buccal mucosa epithelial cells for gene expression profiling. Biotechniques, 2004, 36:484-497.
11. Kharchenko S V, Shpakov A A: Regulation of the RNase activity of saliva in healthy subjects and in stomach cancer. Inz Akad Nauk SSSR Biol, 1989, 1:58-63.
12. Ceder O, van Dijken J, Ericson T, Kollberg J: Ribonuclease in different types of saliva from cystic fibrosis patients. Acta Paediatr. Scand, 1985, 74:102-104.
13. Spivak S, Hurteau G, Jain R, Kumar S, Aldous K, Gierthy J, Kaminsky L S: Gene-Environment Interaction Signatures by Quantitative mRNA Profiling of Exfoliated Buccal Mucosal Cells. Cancer Research, 2004, 64:6805-6813.
14. Guajardo J R, Schleifer K W, Daines M O, Ruddy R M, Aronow B J, Wills-Karp M, Hershey G K, Altered gene expression profiles in nasal respiratory epithelium reflext stable versus acute childhood asthma. J. Allergy Clin Immunol. 2005,
15. Wright J M, Merlo C A. Reynolds J B, Zeldin P L. Garcia J N, Guggino W B, Boyle M P. Respiratory epithelial gene expression in patients with mild and severe cystic fibrosis lung disease. Am. J. Resp. Cell Biology, 2006, 35: 327-336.
16. Wright J M, Merlo C A, Reynolds J B, Zeitlin P L, Garcia J G N, Guggino W B, Boyle M P. Respiratory Epithelial Gene Expression in Patients with Mild and Severe Cystic Fibrosis Lung Disease. Am J Respir Cell Mol Biol, 2006, 35(3):327-336.
17. Slaughter D P, Southwick H W, Smejkal W: Field cancerization in oral stratified squamous epithelium; clinical implications of multicentric origin. Cancer, 1953, 6:963-968.
18. Wistuba I, Lam S, Behrens C, Virmani A, Fong K W, LeRiche J, Samet J, Srivastava S, Minna J, Gazdar A. Molecular damage in the bronchial epithelium of current and former smokers. JNCI. 89: 18. 1366-1373.
19. Partridge M, Emilion G, Pateromichelakis S, Phillips E, Langdon J: Field cancerisation of the oral cavity: Comparison of the spectrum of molecular alterations in cases presenting with both dysplastic and malignant lesions. Oral Oncol, 1997, 33:332-337.
20. Bosatra A, Bussani R, Silvestri F: From epithelial dysplasia to squamous carcinoma in the head and neck region: an epidemiological assessment. Acta Otolaryngol Suppl, 1997, 527:49-51.
21. Sudbo J, Kildal W, Risberg B, Koppang H S, Danielsen H E, Reith A: DNA content as a prognostic marker in patients with oral leukoplakia. N Engl J Med, 2001, 344(17):1270-1278.
22. Demedts I K, Demoor T, Bracke K R, Joos G F, Brusselle G G: Role of apoptosis in the pathogenesis of COPD and pulmonary emphysema. Respir Res., 2006, 7:53.
23. Loro L, Johannessen A C, Vintermyr O K: Decreased expression of bcl-2 in moderate and severe oral epithelia dysplasias. Oral Oncol., 2002, 38(7):691-698.
24. Yang S R, Chida A S, Bauter M R, Shafiq N, Seweryniak K. Maggirwar S B, Kilty I, Rahman I: Cigarette smoke induces proinflammatory cytokine release by activation of NF-kappaB and posttranslational modifications of histone deacetylase in macrophages. Am J Physiol Lung Cell Mol Physiol., 2006, 291(1):L46-57.
25. Sasaki H, Moriyama S, Nakashima Y, Kobayashi. Y. Kiriyama M, Fukai I, Yamakawa Y. Fujii Y: Histone deacetylase 1 mRNA expression in lung cancer. Lung Cancer, 2004, 46(2):171-178.
26. Balciunaite E, Spektor A, Lents N H, Cam H, Te Riele H, Scime A, Rudnicki M A, Young R, Dynlacht B D: Pocket protein complexes are recruited to distinct targets in quiescent and proliferating cells. Mol Cell Biol, 2005, 25(18):81664178.
27. Soni S, Kaur J, Kumar A, Chakravarti N, Mathur M, Bahadur S, Shukla N K, Deo S V, Ralhan R: Alterations of rb pathway components are frequent events in patients with oral epithelial dysplasia and predict clinical outcome in patients with squamous cell carcinoma. Oncology, 2005, 68(4-6):314-325.
28. Xue Jun H, Gemma A, Hosoya Y, Matsuda K, Nara M, Hosomi Y, Okano T, Kurimoto F, Seike M, Takenaka K, Yoshimura A, Toyota M, Kudoh S. Reduced transcription of the RB2/p130 gene in human lung cancer. Mol Carcinog, 2003, 38(3):124-129.
29. Mishina T, Dosaka-Akita H, Hommura F, Nishi M, Kojima T, Ogura S, Shimizu M, Katoh H, Kawakami Y: Cyclin E expression, a potential prognostic marker for non-small cell lung cancers. Clin Cancer Res, 2000, 6(1):11-16.
30. Shintani S, Mihara M, Nakahara Y, Kiyota A, Ueyama Y, Matsumura T, Wong D T. Expression of cell cycle control proteins in normal epithelium, premalignant and malignant lesions of oral cavity. Oral Oncol, 2002, 38(3): 235-243.
31. Kim J H, Sherman M E, Curriero F C, Guengerich F P, Strickland P T, Sutter T R: Expression of cytochromes P450 1A1 and 1B1 in human lung from smokers, non-smokers, and ex-smokers. Toxicol Appl Pharmacol, 2004, 299:210-219
32. Rusznak C, Mills P, Devalia J, Sapsford R, Davies R Lozewicz S: Effect of cigarette smoke on the permeability and IL-1beta and sICAM-1 release from cultured human bronchial epithelial cells of never-smokers, smokers, and patients with chronic obstructive pulmonary disease. American Journal of Respiratory and Molecular Cell Biology. 2000, 23:530-536.
33. Katsuragi H, Hasegawa A, Saito K: Distribution of metallothionein in cigarette smokers and nonsmokers in advanced periodontitis patients. Journal of Periodontology, 1997, 68(10):1005-9
34. Cardosa S V, Barbosa H M, Candellori E M, Loyola A M, Aguiar M C: Prognostic impact of metallothionein on oral squamous cell cancer. Virchows Archive, 2002, 441 (2):174-178.
35. Li Y, Maic A, Zhou X, Kim Y, Sinha U, Jordan R, Eisele D, Abemayor E, Elashoff D, Park N, Wong D: Salivary Transcriptome Diagnostics for Oral Cancer Detection. Clinical Cancer Research, 2004, 10:8442-8450.
36. Li Y, Zhou X, St. John M A R, Wong D T W: RNA profiling of cell-free saliva using microarray technology. J Dent Res, 2004, 83(3):199-203.
37. The Mouth Database at the World Wide Web address pulm.bumc.bu.edu/MouthDB/index.
38. The R-project for Statistical Computing at the World Wide Web address r-project.org.
39. Spotfire at the World Wide Web address spotfire.com.
40. EASE at the World Wide Web address david.abcc.nciferf.gov/tools.jsp.
41. CLUSTER, TREVIEW at the World Wide Web address rana.lbl.gov/EisenSoftware.
43. Subramanian A, Tamayo P, Mootha V K, Mukherjee S, Ebert B L, Gillette M A, Paulovich A, Pomeroy S L, Golub T R, Lander E S, Mesirov J P: Gene set enrichment analysis: A knowledge-based approach for interpreting genome-wide expression profiles. PNAS, 2005, 102(43): 15545-15550.
44. Ding, C, Cantor, C R: A high-throughput gene expression analysis technique using competitive PCR and matrix-assisted laser desorption ionization time-of-flight MS. PNAS, 2003, 100(6):3059-3064.
45. Vandesompele J, De Preter K, Pattyn F, Poppe B, Van Roy N, De Paepe A, Speleman F: Accurate normalization of real-time quantitative RT-PCR data by geometric averaging of multiple internal control genes. Genome Biol, 2002, 3(7).

We claim:

1. A method of processing or analyzing a biological sample of a human subject, comprising:
   a) obtaining a biological sample comprising nasal epithelial cells from the nasal passage of the human subject; and
   b) measuring an expression level of a plurality of genes, wherein the plurality of genes consists of AMACR, BCAP29, CPE, FLCN, PTGER4, USH1C, UBE1L, CCT4, EIF4A1, DUSP3, SDHC, CSNK1G2, TUSC4, DMTF1, MPV17, TFDP2, RREB1, ADK, FLJ11806, CDK5, RAD1, FLJ10613, CXorf34, APS, NFIC, HSF2BP, AOC2, FLJ14107, USP34, KIAA0894, MPP2, ATP6V1E1, DNAJB6, NCOA3, KPNA4, COQ7, BTN3A1, ATM, HFE, ATRN, ATP8A1, ELOVL5, IVL, N2N, THEA, PRDX2, AKAP11, NKX3-1, PRPS1 and GPC6.

2. The method of claim 1, wherein the expression levels of gene transcripts are measured by reverse-transcription polymerase chain reaction (RT-PCR) analysis, nucleic acid chip analysis, or messenger RNA analysis.

3. The method of claim 1, wherein the human subject is a smoker or former smoker.

4. The method of claim 1, wherein the human subject has been exposed to an airway pollutant.

5. The method of claim 4, wherein the airway pollutant is cigarette or cigar smoke.

6. The method of claim 4, wherein the airway pollutant is smog or asbestos.

7. The method of claim 1, wherein the human subject is suspected of having eosinophilic pneumonia, hypersensitivity pneumonitis, pulmonary alveolar proteinosis, systemic sclerosis, idiopathic pulmonary hemosiderosis, or pulmonary fibrosis.

8. The method of claim 1, further comprising obtaining an additional biological sample from the human subject.

9. The method of claim 8, wherein the additional biological sample is obtained from the subject at least one week after obtaining the biological sample.

10. The method of claim 1, further comprising confirming an integrity of ribonucleic acids of the biological sample.

11. The method of claim 1, wherein the human subject is asymptomatic for a lung cancer.

12. The method of claim 1, wherein the human subject has not been previously diagnosed with a lung cancer.

* * * * *